United States Patent [19]

Cho et al.

[11] Patent Number: 5,670,499
[45] Date of Patent: Sep. 23, 1997

[54] NON-PEPTIDE TACHYKININ RECEPTOR ANTAGONISTS

[75] Inventors: Sung Y. Cho; Thomas A. Crowell, both of Indianapolis; Bruce D. Gitter, Carmel; Philip A. Hipskind, New Palestine, all of Ind.; J. Jeffry Howbert, Bellevue, Wash.; Joseph H. Krushinski, Jr., Indianapolis, Ind.; Karen L. Lobb, Indianapolis, Ind.; Brian S. Muehl, Indianapolis, Ind.; James A. Nixon, Indianapolis, Ind.

[73] Assignee: Eli Lilly and Company, Indianapolis, Ind.

[21] Appl. No.: 462,415

[22] Filed: Jun. 5, 1995

Related U.S. Application Data

[62] Division of Ser. No. 153,847, Nov. 17, 1993, abandoned.

[51] Int. Cl.$^6$ .................. A61K 31/40; C07D 295/108
[52] U.S. Cl. .................. 514/231.5; 514/307; 514/339; 514/314; 514/414; 544/143; 546/146; 546/175; 546/277.5; 548/454; 548/455; 548/467
[58] Field of Search .................. 544/143; 546/146, 546/277.4, 175; 548/454, 455, 467; 514/231.5, 414, 314, 339, 307

[56] References Cited

U.S. PATENT DOCUMENTS

| | | |
|---|---|---|
| 4,757,151 | 7/1988 | Horwell . |
| 5,102,667 | 4/1992 | Dubroeucq et al. . |
| 5,137,873 | 8/1992 | Yankner . |
| 5,164,372 | 11/1992 | Matsuo et al. . |
| 5,187,156 | 2/1993 | Matsuo et al. . |

FOREIGN PATENT DOCUMENTS

| | | |
|---|---|---|
| 0 224151 A2 | 6/1987 | European Pat. Off. . |
| 0 230151 A2 | 7/1987 | European Pat. Off. . |
| 0 336356 A2 | 10/1989 | European Pat. Off. . |
| WO92/04038 | 3/1992 | WIPO . |
| WO93/01169 | 1/1993 | WIPO . |
| WO93/01170 | 1/1993 | WIPO . |
| WO93/10073 | 5/1993 | WIPO . |
| WO93/18023 | 9/1993 | WIPO . |
| WO94/01402 | 1/1994 | WIPO . |

OTHER PUBLICATIONS

B.D. Gitter, et al., "Species Differences in Affinities of Non-Peptide Antagonists for Substance P Receptors", *European Journal of Pharmacology*, 197:237–238 (1991).

D. Jukic, et al., "Neurokinin Receptors Antagonists: Old and New", *Life Sciences*, 49:1463–1469 (19910.

C.A. Maggi, et al., "Tachykinin Receptors and Tachykinin Receptor Antagonists", *Journal of Autonomic Pharmacology*, 13:23–93 (1993).

*Primary Examiner*—Jacqueline Haley
*Attorney, Agent, or Firm*—Paul J. Gaylo; David E. Boone

[57] ABSTRACT

This invention provides a novel series of non-peptidyl compounds which are useful in the treatment or prevention of a physiological disorder associated with an excess of tachykinins. This invention also provides methods for the treatment of such physiological disorders as well as pharmaceutical formulations which employ these novel compounds.

9 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Phe  Xaa  Gly  Leu  Met
    1                        5

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Arg  Pro  Lys  Pro  Gln  Gln  Phe  Phe  Gly  Leu  Met
    1                    5                                  10

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
His Lys Thr Asp Ser Phe Val Gly Leu Met
1               5                   10
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Asp Met His Asp Phe Phe Val Gly Leu Met
1               5                   10
```

NON-PEPTIDE TACHYKININ RECEPTOR ANTAGONISTS

This application is a division of application Ser. No. 08/153,847 filed Nov. 17, 1993.

BACKGROUND OF THE INVENTION

Tachykinins are a family of peptides which share the common amidated carboxy terminal sequence, Phe—Xaa—Gly—Leu—Met—NH$_2$ hereinafter referred to as SEQ ID NO:1. Substance P was the first peptide of this family to be isolated, although its purification and the determination of its primary sequence did not occur until the early 1970's. Substance P has the following amino acid sequence, Arg—Pro—Lys—Pro—Gln—Gln—Phe—Phe—Gly—Leu—Met—NH$_2$ hereinafter referred to as SEQ ID NO:2.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3):237–243 (1985) for a review of these discoveries. Neurokinin A has the following amino acid sequence, His—Lys—Thr—Asp—Ser—Phe—Val—Gly—Leu—Met—NH$_2$ hereinafter referred to as SEQ ID NO:3. The structure of neurokinin B is the amino acid sequence, Asp—Met—His—Asp—Phe—Phe—Val—Gly—Leu—Met—NH$_2$ hereinafter referred to as SEQ ID NO:4.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

In essence, this invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

SUMMARY OF THE INVENTION

This invention encompasses methods for the treatment or prevention of a physiological disorder associated with an excess of tachykinins, which method comprises administering to a mammal in need of said treatment an effective amount of a compound of Formula I

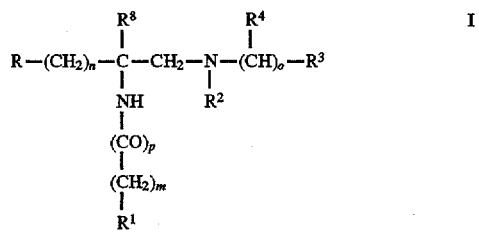

wherein
m is 0, 1, 2, or 3;
n is 0 or 1;
o is 0, 1, or 2;
p is 0 or 1;
R is phenyl, 2- or 3-indolyl, 2- or 3-indolinyl, benzothienyl, benzofuranyl, or naphthyl;
which groups may be substituted with one or two halo, $C_1$–$C_3$ alkoxy, trifluoromethyl, $C_1$–$C_4$ alkyl, phenyl-$C_1$–$C_3$ alkoxy, or $C_1$–$C_4$ alkanoyl groups;
$R^1$ is trityl, phenyl, diphenylmethyl, phenoxy, phenylthio, piperazinyl, piperidinyl, pyrrolidinyl, morpholinyl, indolinyl, indolyl, benzothienyl, hexamethyleneiminyl, benzofuranyl, tetrahydropyridinyl, quinolinyl, isoquinolinyl, reduced quinolinyl, reduced isoquinolinyl, phenyl-($C_1$–$C_4$ alkyl)-, phenyl-($C_1$–$C_4$ alkoxy)-, quinolinyl-($C_1$–$C_4$ alkyl)-, isoquinolinyl-($C_1$–$C_4$ alkyl)-, reduced quinolinyl-($C_1$–$C_4$ alkyl)-, reduced isoquinolinyl-($C_1$–$C_4$ alkyl)-, benzoyl-($C_1$–$C_3$ alkyl)-, $C_1$–$C_4$ alkyl, or —NH—CH$_2$—R$^5$;
any one of which $R^1$ groups may be substituted with halo, $C_1$–$C_4$ alkyl, $C_1$–$C_4$ alkoxy, trifluoromethyl, amino, $C_1$–$C_4$ alkylamino, di($C_1$–$C_4$ alkyl)amino, or $C_2$–$C_4$ alkanoylamino;
or any one of which $R^1$ groups may be substituted with phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl;
any one of which groups may be substituted with halo, $C_1$–$C_4$ alkyl, $C_1$–$C_4$ alkoxy, trifluoromethyl, amino, $C_1$–$C_4$ alkylamino, di($C_1$–$C_4$ alkyl)amino, or $C_2$–$C_4$ alkanoylamino;
or $R^1$ is amino, a leaving group, hydrogen, $C_1$–$C_4$ alkylamino, or di($C_1$–$C_4$ alkyl)amino;
$R^5$ is pyridyl, anilino-($C_1$–$C_3$ alkyl)-, or anilinocarbonyl;
$R^2$ is hydrogen, $C_1$–$C_4$ alkyl, $C_1$–$C_4$ alkylsulfonyl, carboxy-($C_1$–$C_3$ alkyl)-, $C_1$–$C_3$ alkoxycarbonyl-($C_1$–$C_3$ alkyl)-, or —CO—$R^6$;
$R^6$ is hydrogen, $C_1$–$C_4$ alkyl, $C_1$–$C_3$ haloalkyl, phenyl, $C_1$–$C_3$ alkoxy, $C_1$–$C_3$ hydroxyalkyl, amino, $C_1$–$C_4$ alkylamino, di($C_1$–$C_4$ alkyl)amino, or —(CH$_2$)$_q$—$R^7$;
q is 0 to 3;
$R^7$ is carboxy, $C_1$–$C_4$ alkoxycarbonyl, $C_1$–$C_4$ alkylcarbonyloxy, amino, $C_1$–$C_4$ alkylamino, di($C_1$–$C_4$ alkyl)amino, $C_1$–$C_6$ alkoxycarbonylamino, or
phenoxy, phenylthio, piperazinyl, piperidinyl, pyrrolidinyl, morpholinyl, indolinyl, indolyl, benzothienyl, benzofuranyl, quinolinyl, isoquinolinyl, reduced quinolinyl, reduced isoquinolinyl, phenyl-($C_1$–$C_4$ alkyl)-, quinolinyl-($C_1$–$C_4$ alkyl)-, isoquinolinyl-($C_1$–$C_4$ alkyl)-, reduced quinolinyl-($C_1$–$C_4$ alkyl)-, reduced isoquinolinyl-($C_1$–$C_4$ alkyl)-, benzoyl-$C_1$–$C_3$ alkyl;

any one of which $R^7$ groups may be substituted with halo, trifluoromethyl, $C_1$–$C_4$ alkoxy, $C_1$–$C_4$ alkyl, amino, $C_1$–$C_4$ alkylamino, di($C_1$–$C_4$ alkyl)amino, or $C_2$–$C_4$ alkanoylamino;

or any one of which $R^7$ groups may be substituted with phenyl, piperazinyl, $C_3$–$C_8$ cycloalkyl, benzyl, piperidinyl, pyridinyl, pyrimidinyl, pyrrolidinyl, $C_2$–$C_6$ alkanoyl, or $C_1$–$C_4$ alkoxycarbonyl;

any of which groups may be substituted with halo, trifluoromethyl, amino, $C_1$–$C_4$ alkoxy, $C_1$–$C_4$ alkyl, $C_1$–$C_4$ alkylamino, di($C_1$–$C_4$ alkyl)amino, or $C_2$–$C_4$ alkanoylamino;

$R^8$ is hydrogen or $C_1$–$C_6$ alkyl;

$R^3$ is phenyl, phenyl-($C_1$–$C_6$ alkyl)-, $C_3$–$C_8$ cycloalkyl, $C_5$–$C_8$ cycloalkenyl, $C_1$–$C_8$ alkyl, naphthyl, $C_2$–$C_8$ alkenyl, or hydrogen;

any one of which groups except hydrogen may be substituted with one or two halo, $C_1$–$C_3$ alkoxy, $C_1$–$C_3$alkylthio, nitro, trifluoromethyl, or $C_1$–$C_3$ alkyl groups; and $R^4$ is hydrogen or $C_1$–$C_3$ alkyl;

with the proviso that if $R^1$ is hydrogen or halo, $R^3$ is phenyl, phenyl-($C_1$–$C_6$ alkyl)-, $C_3$–$C_8$ cycloalkyl, $C_5$–$C_8$ cycloalkenyl, or naphthyl; with the proviso that if $R^1$ is hydrogen or halo, $R^3$ is phenyl, phenyl-($C_1$–$C_6$ alkyl)-, $C_3$–$C_8$ cycloalkyl, $C_5$–$C_8$ cycloalkenyl, or naphthyl;

or a pharmaceutically acceptable salt thereof.

In another embodiment, this invention encompasses the novel compounds of Formula I and the pharmaceutically acceptable salts, solvates, and prodrugs thereof, as well as pharmaceutical formulations comprising, as an active ingredient, a compound of Formula I in combination with a pharmaceutically acceptable carrier, diluent or excipient. This invention also encompasses novel processes for the synthesis of the compounds of Formula I.

DETAILED DESCRIPTION AND PREFERRED EMBODIMENTS

All temperatures stated herein are in degrees Celsius (°C.). All units of measurement employed herein are in weight units except for liquids which are in volume units.

As used herein, the term "$C_1$–$C_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "$C_1$–$C_6$ alkyl" includes within its definition the term "$C_1$–$C_4$ alkyl".

"Divalent($C_1$–$C_4$)alkyl" represents a straight or branched divalent saturated aliphatic chain having from one to four carbon atoms. Typical divalent($C_1$–$C_4$)alkyl groups include methylene, ethylene, propylene, 2-methylpropylene, butylene and the like.

"Halo" represents chloro, fluoro, bromo or iodo.

"Halo($C_1$–$C_4$)alkyl" represents a straight or branched alkyl chain having from one to four carbon atoms with 1, 2 or 3 halogen atoms attached to it. Typical halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

"Hydroxy($C_1$–$C_4$)alkyl" represents a straight or branched alkyl chain having from one to four carbon atoms with hydroxy group attached to it. Typical hydroxy($C_1$–$C_4$)alkyl groups include hydroxymethyl, 2-hydroxyethyl, 1-hydroxyisopropyl, 2-hydroxypropyl, 2-hydroxybutyl, 3-hydroxyisobutyl, hydroxy-t-butyl and the like.

"$C_1$–$C_6$ alkylthio" represents a straight or branched alkyl chain having from one to six carbon atoms attached to a sulfur atom. Typical $C_1$–$C_6$ alkylthio groups include methylthio, ethylthio, propylthio, isopropylthio, butylthio and the like. The term "$C_1$–$C_6$ alkylthio" includes within its definition the term "$C_1$–$C_4$ alkylthio".

The term "$C_2$–$C_8$ alkenyl" as used herein represents a straight or branched, monovalent, unsaturated aliphatic chain having from two to eight carbon atoms. Typical $C_2$–$C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

"$C_5$–$C_8$ cycloalkenyl" represents a hydrocarbon ring structure containing from five to eight carbon atoms and having at least one double bond within that ring, which is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$ alkylamino, di($C_1$–$C_4$)alkylamino or —$(CH_2)_a$—$R^c$ where a is 1, 2, 3 or 4 and $R^c$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

"$C_1$–$C_4$ alkylamino" represents a straight or branched alkylamino chain having from one to four carbon atoms attached to an amino group. Typical $C_1$–$C_4$ alkylamino groups include methylamino, ethylamino, propylamino, isopropylamino, butylamino, sec-butylamino and the like.

"Di($C_1$–$C_4$ alkyl)amino" represents a straight or branched dialkylamino chain having two alkyl chains, each having independently from one to four carbon atoms attached to a common amino group. Typical di($C_1$–$C_4$)alkylamino groups include dimethylamino, ethylmethylamino, methylisopropylamino, t-butylisopropylamino, di-t-butylamino and the like.

"Arylsulfonyl" represents an aryl moiety attached to a sulfonyl group. "Aryl" as used in this term represents a phenyl, naphthyl, heterocycle, or unsaturated heterocycle moiety which is optionally substituted with 1, 2 or 3 substituents independently selected from halo, halo($C_1$–$C_4$) alkyl, $C_1$–$C_4$ alkyl, $C_1$–$C_4$ alkoxy, carboxy, $C_1$–$C_4$ alkoxycarbonyl, carbamoyl, N—($C_1$–$C_4$)alkylcarbamoyl, amino, $C_1$–$C_4$ alkylamino, di($C_1$–$C_4$)alkylamino or —$(CH_2)_a$—$R^b$ where a is 1, 2, 3 or 4; and $R^b$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N-($C_1$–$C_4$)-alkylcarbamoyl, amino, $C_1$–$C_4$ alkylamino, di($C_1$–$C_4$) alkylamino or —$(CH_2)_a$—$R^d$ where a is 1, 2, 3 or 4; and $R^d$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N—($C_1$–$C_4$) alkylcarbamoyl, amino, $C_1$–$C_4$ alkylamino, di($C_1$–$C_4$) alkylamino or —$(CH_2)_a$—$R^e$ where a is 1, 2, 3 or 4; and $R^e$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$) alkylamino.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, tetrahydrisoquinolinyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

"$C_2$–$C_6$ alkanoyl" represents a straight or branched alkyl chain having from one to five carbon atoms attached to a carbonyl moiety. Typical $C_2$–$C_6$ alkanoyl groups include ethanoyl, propanoyl, isopropanoyl, butanoyl, t-butanoyl, pentanoyl, hexanoyl, 3-methylpentanoyl and the like.

"$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

"$C_3$–$C_8$ cycloalkyl" represents a saturated hydrocarbon ring structure containing from three to eight carbon atoms which is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, N—($C_1$–$C_4$)alkylcarbamoyl, amino, $C_1$–$C_4$ alkylamino, di($C_1$–$C_4$)alkylamino or —$(CH_2)_a$—$R^f$ where a is 1, 2, 3 or 4 and $R^f$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Typical $C_3$–$C_8$ cycloalkyl groups include cyclopropyl, cyclopentyl, cyclohexyl, cycloheptyl, 3-methyl-cyclopentyl, 4-ethoxycyclohexyl, 4-carboxycycloheptyl, 2-chlorocyclohexyl, cyclobutyl, cyclooctyl, and the like.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (t-BOC), allyloxycarbonyl and benzyloxycarbonyl. Further examples of groups referred to by the above terms are described by E. Haslam, "Protective Groups in Organic Chemistry", (J. G. W. McOmie, ed., 1973), at Chapter 2; and T. W. Greene and P. G. M. Wuts, "Protective Groups in Organic Synthesis" (1991), at Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4, 4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra, at Chapter 5, and T. W. Greene, et al., supra, at Chapter 5.

The term "leaving group" as used herein refers to a group of atoms that is displaced from a carbon atom by the attack of a nucleophile in a nucleophilic substitution reaction. The term "leaving group" as used in this document encompasses, but is not limited to, activating groups.

The term "activating group" as used herein refers a leaving group which, when taken with the carbonyl (—C=O) group to which it is attached, is more likely to take part in an acylation reaction than would be the case if the group were not present, as in the free acid. Such activating groups are well-known to those skilled in the art and may be, for example, succinimidoxy, phthalimidoxy, benzotriazolyloxy, benzenesulfonyloxy, methanesulfonyloxy, toluenesulfonyloxy, azido, or —O—CO—($C_4$–$C_7$ alkyl).

The compounds used in the method of the present invention have multiple asymmetric centers. As a consequence of these chiral centers, the compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

As noted supra, this invention includes the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses the pharmaceutically acceptable solvates of the compounds of Formulas I. Many of the Formula I compounds can combine with solvents such as water, methanol, ethanol and acetonitrile to form pharmaceutically acceptable solvates such as the corresponding hydrate, methanolate, ethanolate and acetonitrilate.

The especially preferred compounds used in the methods of this invention are those of Formula I wherein a) R is substituted or unsubstituted 2- or 3-indolyl, phenyl, or naphthyl;

b) n is 1;

c) $R^1$ is phenyl, substituted phenyl, piperidinyl, substituted piperidinyl, piperazinyl, substituted piperazinyl, pyrrolidinyl, pyridyl, benzoyl, or morpholinyl;

d) $R^2$ is —CO—$R^6$, $C_1$–$C_4$ alkylsulfonyl, or $C_1$–$C_3$ alkoxycarbonyl-($C_1$–$C_3$ alkyl)-;

e) $R^3$ is phenyl, substituted phenyl, $C_3$–$C_8$ cycloalkyl, substituted $C_3$–$C_8$ cycloalkyl, naphthyl or substituted naphthyl; and f) $R^8$ is hydrogen or methyl.

A most preferred group of compounds used in the methods of this invention are those of Formula I wherein R is optionally substituted indolyl, $R^1$ is substituted piperidinyl or substituted piperazinyl, $R^8$ is hydrogen, and $R^2$ is acetyl or methylsulfonyl. Another preferred group of compounds used in the methods of this invention are those of Formula I wherein R is naphthyl, $R^1$ is optionally substituted phenyl, substituted piperidinyl or substituted piperazinyl, $R^2$ is acetyl or methylsulfonyl, and $R^3$ is phenyl or substituted phenyl.

The especially preferred compounds of this invention are those of Formula I wherein a) R is substituted or unsubstituted 2- or 3-indolyl, phenyl, or naphthyl;

b) n is 1;

c) $R^1$ is trityl, phenyl, substituted phenyl, piperidinyl, substituted piperidinyl, piperazinyl, substituted piperazinyl, pyrrolidinyl, pyridyl, benzoyl, or morpholinyl;

d) $R^2$ is —CO—$R^6$, $C_1$-$C_4$ alkylsulfonyl, or $C_1$-$C_3$ alkoxycarbonyl-($C_1$-$C_3$ alkyl)-;

e) $R^3$ is phenyl, substituted phenyl, $C_3$-$C_8$ cycloalkyl, substituted $C_3$-$C_8$ cycloalkyl, naphthyl or substituted naphthyl; and f) $R^8$ is hydrogen or methyl.

The compounds of the present invention can be prepared by a variety of procedures well known to those of ordinary skill in the art. The particular order of steps required to produce the compounds of Formula I is dependent upon the particular compound being synthesized, the starting compound, and the relative lability of the substituted moieties.

Examples of such protocols are depicted in Schemes I through IV. The coupling of the substituted amine to the compound of Formula II (Method A) can be performed by many means known in the art, the particular methods employed being dependent upon the particular compound of Formula II which is used as the starting material and the type of substituted amine used in the coupling reaction. These coupling reactions frequently employ commonly used coupling reagents such as 1,1-carbonyl diimidazole, dicyclohexylcarbodiimide, diethyl azodicarboxylate, 1-hydroxybenzotriazole, alkyl chloroformate and triethylamine, phenyldichlorophosphate, and chlorosulfonyl isocyanate. Examples of these methods are described infra. After deprotection of the amino group, the compounds of Formula III are obtained.

The compound of Formula III is then reduced, converting the amide into an amine (Method B). Amides can be reduced to amines using procedures well known in the art. These reductions can be performed using lithium aluminum hydride as well as by use of many other different aluminum-based hydrides. Alternatively, the amides can be reduced by catalytic hydrogenation, though high temperatures and pressures are usually required for this. Sodium borohydride in combination with other reagents may be used to reduce the amide. Borane complexes, such as a borane dimethylsulfide complex, are especially useful in this reduction reaction.

The next step in Scheme I (Method C) is the selective acylation of the primary amine using standard methods, as typified by Method C. Because of the higher steric demand of the secondary amine, the primary amine is readily available for selective substitution.

This acylation can be done using any of a large number of techniques regularly employed by those skilled in organic chemistry. One such reaction scheme is a substitution using an anhydride such as acetic anhydride. Another reaction scheme often employed to acylate a primary amine employs a carboxylic acid preferably with an activating agent as described for Method A, supra. An amino-de-alkoxylation type of reaction uses esters as a means of acylating the primary amine. Activated esters which are attenuated to provide enhanced selectivity are very efficient acylating agents.

Scheme I

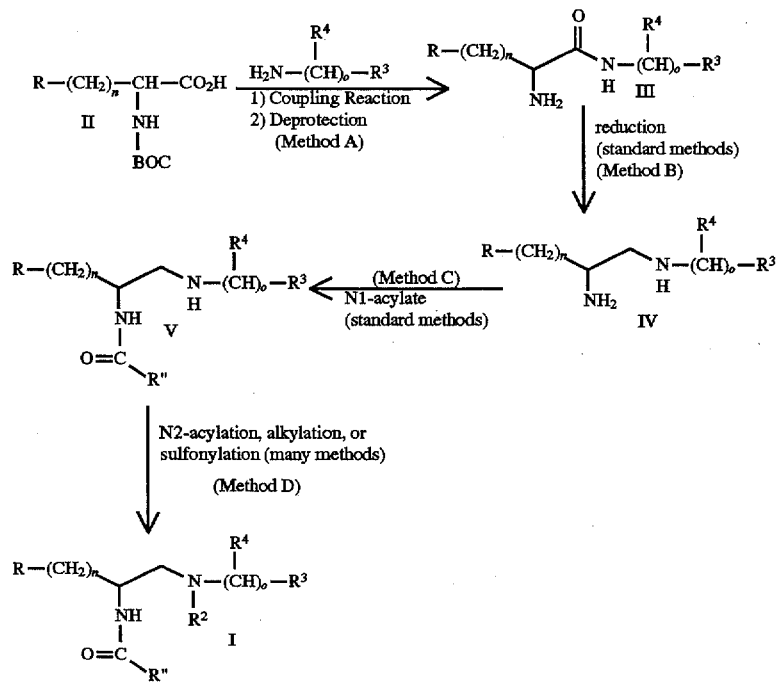

wherein:

R" is equal to —$(CH_2)_m$—$R^1$; and $R^2$ is not hydrogen.

Scheme II

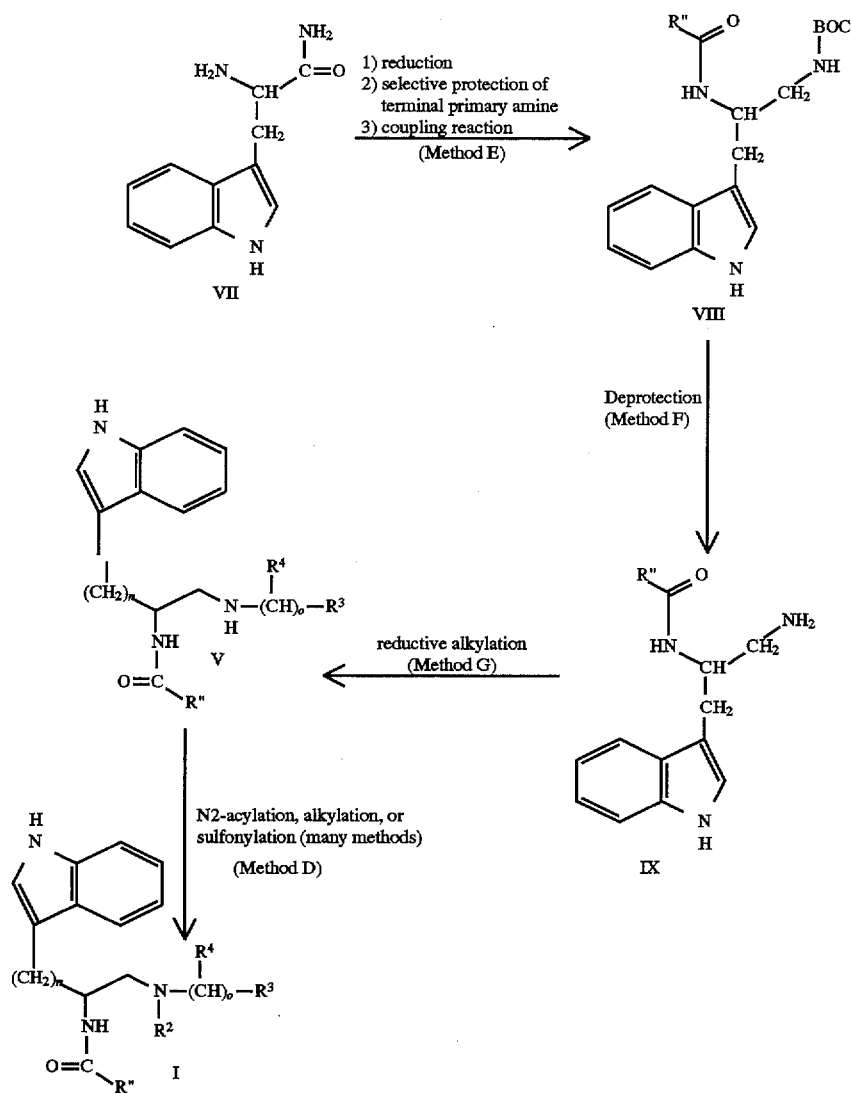

Primary amines can also be acylated using amides to perform what is essentially an exchange reaction. This reaction is usually carried out with the salt of the amine. Boron trifluoride, usually in the form of a boron trifluoride diethyl ether complex, is frequently added to this reaction to complex with the leaving ammonia.

The next procedure is one of substitution of the secondary amine (Method D). For most of the compounds of Formula I this substitution is one of alkylation, acylation, or sulfonation. This substitution is usually accomplished using well recognized means. Typically, alkylations can be achieved using alkyl halides and the like as well as the well-known reductive alkylation methods as seen in Method G, Scheme II, supra, employing aldehydes or ketones. Many of the acylating reaction protocols discussed supra efficiently acylate the secondary amine as well. Alkyl- and aryl-sulfonyl chlorides can be employed to sulfonate the secondary amine.

In many instances one of the later steps in the synthesis of the compounds of Formula I is the removal of an amino- or carboxy-protecting group. Such procedures, which vary, depending upon the type of protecting group employed as well as the relative lability of other moieties on the compound, are described in detail in many standard references works such as T. W. Greene, et al., Protective Groups in Organic Synthesis (1991).

Schemes II and III depict alternative protocols and strategies for the synthesis of the compounds of Formula I. Many of the individual reactions are similar to those described in Scheme I but the reactions of Schemes II and III are done in a different, but yet well known to those skilled in the art, series of steps.

Scheme III

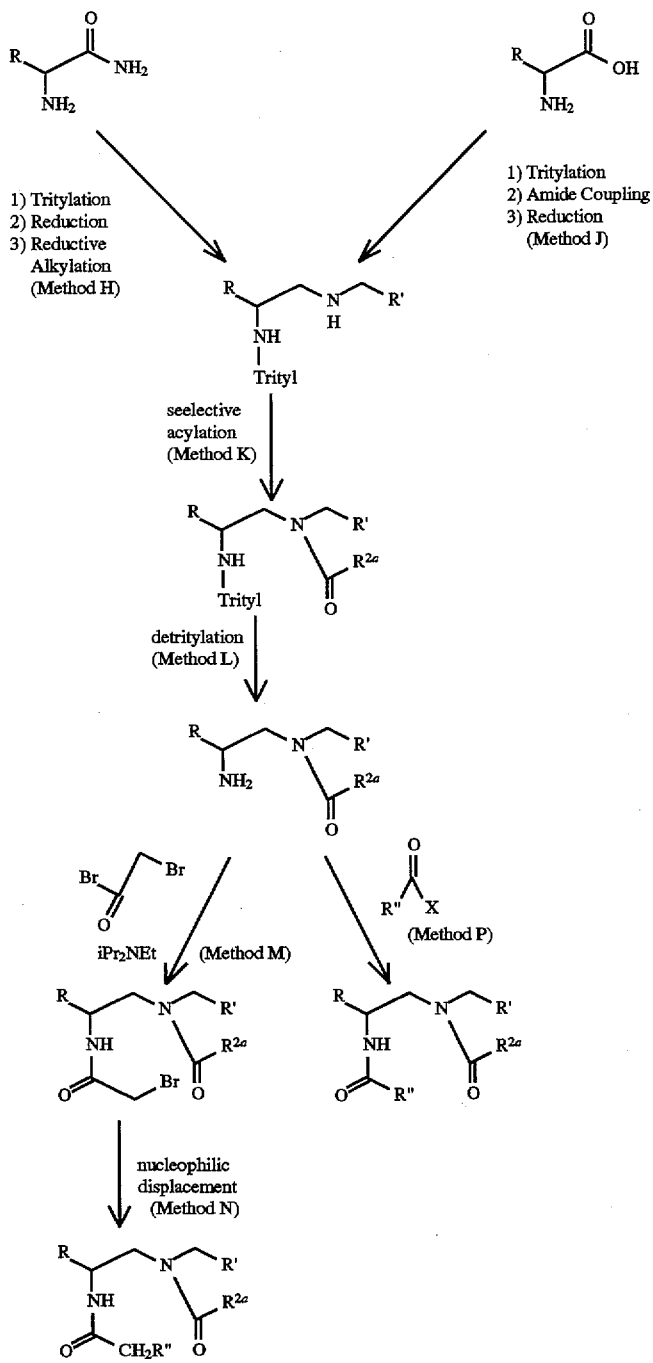

wherein $R^{2a}$ coupled with the carbonyl group to which it is attached is equal to $R^2$.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active salt or base. These diastereomers can then be separated using differential solubility, fractional crystallization, chromatography, or like methods. Further details regarding resolution of enantiomeric mixtures can be found in J. Jacques, et al., "Enantiomers, Racemates, and Resolutions", (1991).

In addition to the schemes described above, the practitioner of this invention may also choose an enantiospecific protocol for the preparation of the compounds of Formula I. Scheme IV, infra, depicts a typical such synthetic reaction design which maintains the chiral center present in the starting material in a desired orientation, in this case in the "R" configuration. These reaction schemes usually produce compounds in which greater than 95 percent of the title product is the desired enantiomer.

Many of the synthetic steps employed in Scheme IV are the same as used in other schemes, especially Scheme III.

The dioxane was removed under reduced pressure. The product was partitioned between ethyl acetate and water and was washed successively with 1 N hydrochloric acid, saturated sodium bicarbonate solution, water, and brine, fol-

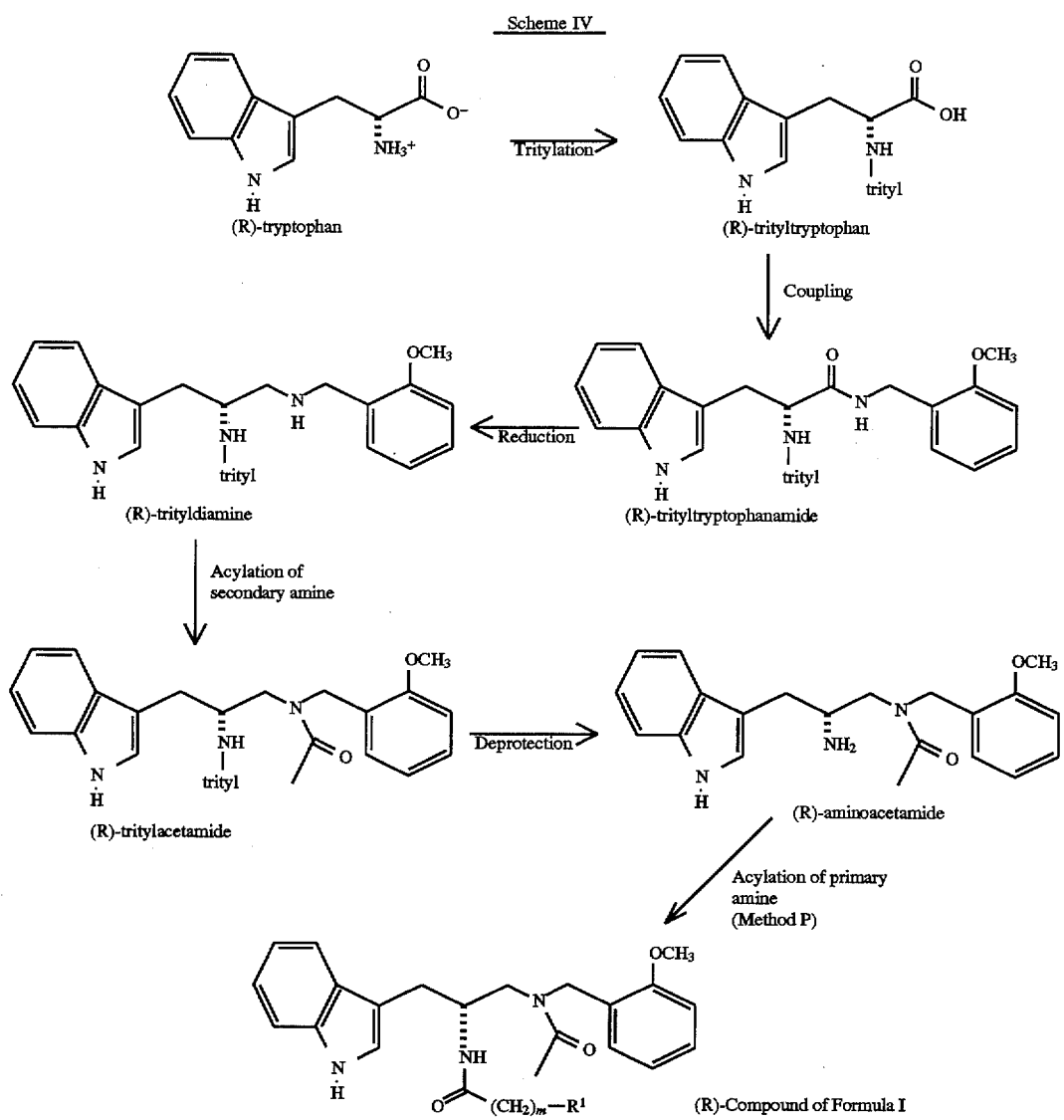

Scheme IV

The following depicts representative examples of reaction conditions employed in the preparation of the compounds of Formula I.

Method A

Coupling of carboxylic acid and primary amine to form amide

Preparation of 2-t-butoxycarbonylamino-3-(1H-indol-3-yl)-N-(2-methoxybenzyl)propanamide To a solution of N-(t-butoxycarbonyl)tryptophan (46.4 g, 152.6 mmoles) in 500 ml of dioxane was added carbonyl diimidazole (25.4 g, 156 mmoles) in a portionwise manner. The resulting mixture was stirred for about 2.5 hours at room temperature and then stirred at 45° C. for 30 minutes. Next, 2-methoxybenzylamine (20.7 ml, 158.7 mmoles) was added and the reaction mixture was then stirred for 16 hours at room temperature.

lowed by drying over sodium sulfate and removal of the solvent. Final crystallization from methanol yielded 52.2 g of homogeneous product as yellow crystals. Yield 80.8%. m.p. 157°–160° C.

Deprotection of primary amine

Synthesis of 2-amino-3-(1H-indol-3-yl)-N-(2-methoxybenzyl)propanamide

To a mixture of the 2-t-butoxycarbonylamino-3-(1H-indol-3-yl)-N-(2-methoxybenzyl)propanamide prepared supra (25.1 g, 59.2 mmoles) and anisole (12 ml, 110.4 mmoles) at 0° C. was added dropwise an aqueous solution of trifluoroacetic acid (118 ml, 1.53 moles) in 50 ml of water. This mixture was stirred for one hour at 0° C., followed by stirring for about 2.5 hours at ambient temperature. The mixture was then refrigerated for about 16 hours.

The volatiles were removed under reduced pressure. The product was partitioned between ethyl acetate and saturated sodium bicarbonate solution and was then washed with water followed by brine and then dried over sodium sulfate. The solvents were removed in vacuo. Recrystallization from a 1:1 diethyl ether/cyclohexane solution yielded 18.0 g (94.2%) of homogeneous product as an off-white powder. m.p. 104°–108° C.

Method B

Reduction of amide carbonyl

Synthesis of 2-amino-3-(1H-indol-3-yl)-1-[N-(2-methoxybenzyl)amino]propane

To a refluxing solution of 2-amino-3-(1H-indol-3-yl)-N-(2-methoxybenzyl)propanamide (9.81 g, 30.3 moles), prepared as described supra, in 100 ml of anhydrous tetrahydrofuran was added dropwise a 10M borane-methyl sulfide complex (9.1 ml, 91.0 moles). The resulting mixture was refluxed for about 2 hours. The mixture was cooled to room temperature and the excess borane was quenched by the dropwise addition of 160 ml of methanol. The resulting mixture was refluxed for 15 minutes and the methanol was removed under reduced pressure.

The residue was dissolved in a saturated methanol solution of hydrochloric acid (250 ml) and the solution refluxed for about 1 hour. The methanol was removed in vacuo and the product was isolated the addition of 5N sodium hydroxide followed by extraction with diethyl ether. The product was then dried over sodium sulfate. The solvents were removed in vacuo. Flash chromatography (silica gel, eluting with methanol:methylene chloride:ammonium hydroxide, 10:100:0.5) provided 7.1 g of a mixture of the title compound (75%) and the indoline derivative of the title product (25%) as an amber oil.

Method C

Acylation of primary amine

Preparation of 3-(1H-indol-3-yl)-1-[N-(2-methoxybenzyl) amino]-2-[N-(2-((4-phenyl)piperazin-1-yl)acetyl amino] propane

[Compound of Example 17]

A mixture of 2-((4-phenyl)piperazin-1-yl)acetic acid, sodium salt (1.64 g, 6.8 mmoles) and triethylamine hydrobromide (1.24 g, 6.8 mmoles) in 35 ml of anhydrous dimethylformamide was heated to 50° C. and remained at that temperature for about 35 minutes. The mixture was allowed to cool to room temperature. 1,1-Carbonyl diimidazole (1.05 g, 6.5 mmoles) and 10 ml of anhydrous dimethylformamide were added to the mixture. The resulting mixture was stirred for about 3 hours at room temperature.

A solution of the 2-amino-3-(1H-indol-3-yl)-1-[N-(2-methoxybenzyl)amino]propane (75%) and the indoline derivative (25%) prepared supra, dissolved in 10 ml of anhydrous dimethylformamide was added to the previous reaction mixture. The resulting mixture was stirred for about 16 hours at room temperature. The dimethylformamide was removed under reduced pressure.

The title product and its indoline derivative were partitioned between ethyl acetate and water and then washed with brine, and dried over sodium sulfate. The solvents were removed in vacuo. This process yielded 3.2 g of a mixture of the title compound and its indoline derivative as a yellow oil. These two compounds were then separated using high performance liquid chromatography using a reverse phase column followed by a silica gel column to give the title product (5.2 % yield) as a yellow foam.

Method D

Techniques of Acylation of Secondary Amine

Preparation of 1-[N-ethoxycarbonyl-N-(2-methoxybenzyl) amino]-3-(1H-indol-3-yl)-2-[N-(2-((4-phenyl)piperazin-1-yl)acetyl)amino]propane

[Compound of Example 28]

To a solution of the 3-(1H-indol-3-yl)-1-[N-(2-methoxybenzyl)amino]-2-[N-(2-((4-phenyl)piperazin-1-yl) acetyl)amino]propane (0.43 g, 0.85 mmole) and triethylamine (130 µl, 0.93 mmole) in 5 ml of anhydrous tetrahydrofuran, was added dropwise ethylchloroformate (89 µl, 0.93 mmole). The resulting mixture was stirred for about 16 hours at room temperature. The tetrahydrofuran was removed under reduced pressure.

The acylated product was partitioned between ethyl acetate and 0.2N sodium hydroxide, and was then washed with water and brine successively, then dried over sodium sulfate. Flash chromatography (silica gel, methanol:methylene chloride, 2.5:97.5) provided 390 mg of homogeneous title product as a white foam.

Preparation of 3-(1H-indol-3-yl)-1-[N-(2-methoxybenzyl)-N-(methylaminocarbonyl)amino]-2-[N-(2-(4-phenyl) piperazin-1-yl)acetyl)amino]propane

[Compound of Example 29]

To a room temperature solution of 3-(1H-indol-3-yl)-1-[N-(2-methoxybenzyl)amino]-2-[N-(2-((4-phenyl) piperazin-1-yl)acetyl)amino]propane (0.40 g, 0.78 mmole) in 10 ml of anhydrous tetrahydrofuran was added dropwise methyl isocyanate (140 µl, 2.3 mmoles). The resulting mixture was then stirred for 16 hours at room temperature. The tetrahydrofuran was removed in vacuo. The title product was isolated by consecutive washes with ethyl acetate, water, and brine, and then dried over sodium sulfate. Flash chromatography using silica gel and a methanol/methylene chloride (5/95) eluant provided 396 mg of the homogeneous product as a yellow oil.

Alkylation of Secondary Amine

Preparation of 1-[N-ethyl-N-(2-methoxybenzyl)amino]-3-(1H-indol-3-yl)-2-[N-(2-((4-phenyl)piperazin-1-yl) acetyl)amino]propane

[Compound of Example 9]

To a room temperature solution of 3-(1H-indol-3-yl)-1-[N-(2-methoxybenzyl)amino]-2-[N-(2-((4-phenyl) piperazin-1-yl)acetyl)amino]propane (0.41 g, 0.80 mmole) in 5 ml of anhydrous N,N-dimethylformamide were added ethyl iodide (120 µl, 1.5 mmoles) and potassium carbonate (120 mg, 0.87 mmole). This mixture was then heated to 50° C. and maintained at that temperature for about 4 hours after which it was stirred at room temperature for about 16 hours. The N,N-dimethylformamide was then removed under reduced pressure. The product was partitioned between ethyl acetate and water, and then washed with brine, before drying over sodium sulfate. The solvents were removed in vacuo. Preparative thin layer chromatography provided 360 mg of the title product as a yellow foam.

Method E

Reduction of the carbonyl of an amide

Preparation of 1,2-diamino-3-(1H-indol-3-yl)propane

Boron trifluoride etherate (12.3 ml, 0.1 mmole) was added to a tetrahydrofuran (24.4 ml) solution of tryptophan amide (20.3 g, 0.1 mole) at room temperature with stirring. At reflux with constant stirring, borane methylsulfide (32.25 ml, 0.34 mole) was added dropwise. The reaction was heated at reflux with stirring for five hours. A tetrahydrofuran:water mixture (26 ml, 1:1) was carefully added dropwise. A sodium hydroxide solution (160 ml, 5N) was added and the mixture heated at reflux with stirring for sixteen hours.

The layers of the cooled mixture were separated and the aqueous was extracted twice with 40 ml each of tetrahydrofuran. These combined tetrahydrofuran extracts were evaporated. Ethyl acetate (800 ml) was added and this solution was washed three times with 80 ml saturated sodium chloride solution. The ethyl acetate extract was dried over sodium sulfate, filtered and evaporated to yield 18.4 g (97%) of the title compound.

Protection of primary amine

Preparation of the 2-amino-1-t-butoxycarbonylamino-3-(1H-indol-3-yl)propane.

Di-t-butyldicarbonate (0.90 ml, 3.9 mmoles) in 10 ml of tetrahydrofuran was added dropwise at room temperature to the 1,2-diamino-3-(1H-indol-3-yl)propane (1.06 g, 5.6 mmoles) produced supra, which was dissolved in 28 ml of tetrahydrofuran. This dropwise addition occurred over a 5 hour period. The solvent was evaporated. Flash chromatography using ethanol/ammonium hydroxide/ethylacetate yielded 0.51 g (1.76 mmoles, 31%) of the desired carbamate.

Acylation of the secondary amine

Preparation of 1-t-butoxycarbonylamino-3-(1H-indol-3-yl)-2-[N-(2-((4-phenyl)piperazin-t-yl)acetyl)amino]propane

[Compound of Example 151]

A slurry of 2-((4-phenyl)piperazin-1-yl)acetic acid (2.47 g, 11.2 mmoles) and triethylamine (3.13 ml, 22.5 mmoles) in acetonitrile (1200 ml) was heated to reflux briefly with stirring. While the resulting solution was still warm carbonyldiimidazole (1.82 g, 11.2 mmoles) was added and the mixture was heated at reflux for 10 minutes. The 2-amino-1-t-butoxycarbonylamino-3-(1H-indol-3yl)propane (3.25 g, 11.2 mmoles) in 50 ml of acetonitrile was then added to the reaction. The resulting mixture was refluxed with stirring for 30 minutes and was then stirred at room temperature overnight.

The reaction mixture was then refluxed with stirring for 5 hours and the solvent was then removed in vacuo. The resulting oil was washed with a sodium carbonate solution, followed by six washes with water, which was followed by a wash with a saturated sodium chloride solution. The resulting liquid was dried over sodium sulfate and filtered. The retained residue was then dried in vacuo. The filtrate was reduced in volume and then partially purified by chromatography. The sample from the chromatograaphy was pooled with the residue retained by the filter, combining for 3.94 grams (72% yield) of the title product.

Method F

Deprotection of Primary Amine

Synthesis of 1-amino-3-(1H-indol-3-yl)-2-[N-(2-((4-phenyl)piperazin-1-yl)acetyl)amino]propane

[Compound of Example 150]

To an ice cold soution of 70% aqueous trifluoroacetic acid (2.8 ml of trifluoroacetic acid in 4.0 ml total volume) were added 1-t-butoxycarbonylamino-3-(1H-indol-3-yl)-2-[N-(2-((4-phenyl)piperazin-1-yl)acetyl)amino]propane (0.80 g, 1.63 mmoles) and anisole (0.4 ml). This mixture was stirred for 35 minutes, resulting in a clear solution. The solution was then stirred for an additional hour and then evaporated.

Ethyl acetate was then added to the resulting liquid, followed by a wash with a sodium carbonate solution. This wash was then followed by three washes with a saturated sodium chloride solution. The resulting solution was then dried over soldium sulfate, filtered and evaporated, resulting in 0.576 g (90% yield) of the title product.

Method G

Reductive Alkylation of Primary Amine

Preparation of 1-[N-(2-chlorobenzyl)amino]-3-(1H-indol-3-yl)-2-[N-(2-((4-phenyl)piperazin-1-yl)acetyl)amino]propane.

[Compound of Example 2]

2-Chlorobenzaldehyde (0.112 g, 0.8 mmole) was combined with the 1-amino-3-(1H-indol-3-yl)-2-[N-(2-((4-phenyl)piperazin-1-yl)acetyl)amino]propane (0.156 g, 0.398 mmole) in toluene. The resulting mixture was then stirred and warmed, and then evaporated. Toluene was then added to the residue and this mixture was again evaporated. Tetrahydrofuran was added to the residue and the mixture was then cooled in an ice bath.

Sodium cyanoborohydride (0.025 g, 0.4 mmole) was then added to the reaction mixture. Gaseous hydrogen chloride was periodically added above the liquid mixture. The mixture was stirred at room temperature for 16 hours and then reduced in volume in vacuo.

A dilute hydrochloric acid solution was then added to the residue and the solution was then extracted twice with ether. The acidic aqueous extract was basified by the dropwise addition of 5N sodium hydroxide. This basified solution was then extracted three times with ethyl acetate. The combined ethyl acetate washes were washed with a saturated sodium chloride solution, dried over sodium sulfate, filtered and evaporated. This process was followed by chromatography yielding 0.163 g (79% yield) of the title product.

Method H

Tritylation

Preparation of 3-(1H-indol-3-yl)-2-(N-triphenylmethylamino)propanamide.

Tryptophan amide (26.43 g, 0.130 mole) was suspended in 260 ml of methylene chloride and this mixture was flushed with nitrogen and then put under argon. Trityl chloride (38.06 g, 0.136 mole) was dissolved in 75 ml of methylene chloride. The trityl chloride solution was slowly added to the tryptophan amide solution which sat in an ice bath, the addition taking about 25 minutes. The reaction mixture was then allowed to stir overnight.

The reaction mixture was then poured into a separation funnel and was washed with 250 ml of water, followed by 250 ml of brine. As the organic layer was filtering through sodium sulfate to dry, a solid precipitated. The filtrate was collected and the solvent was evaporated.

Ethyl acetate was then added to the pooled solid and this mixture was stirred and then refrigerated overnight. The next day the resulting solid was washed several times with cold ethyl acetate and then dried in vacuo. Yield 49.76 g (85.9%).

Reduction of Carbonyl

Preparation of 1-amino-3-(1H-indol-3-yl)-2-(N-triphenylmethylamino)propane

Under argon the 3-(1H-indol-3-yl)-2-(N-triphenylmethylamino)propanamide (48.46 g, 0.108 mole) was suspended in 270 ml of tetrahydrofuran. This mixture was then heated to reflux. Borane-methyl sulfide complex (41.3 g, 0.543 mole) was then slowly added to the reaction mixture. All of the starting amide dissolved during the addition of the borane-methyl sulfide complex. This solution was then stirred overnight in an 83° C. oil bath.

After cooling a 1:1 mixture of tetrahydrofuran:water (75 ml total) was then added to the solution. Sodium hydroxide (5N, 230 ml) was then added to the mixture, which was then heated to reflux for about 30 minutes.

After partitioning the aqueous and organic layers, the organic layer was collected. The aqueous layer was then extracted with tetrahydrofuran. The organic layers were combined and the solvents were then removed by evaporation. The resulting liquid was then partitioned between ethyl acetate and brine and was washed a second time with brine. The solution was then dried over sodium sulfate and the solvents were removed in vacuo to yield 48.68 grams of the desired intermediate.

Substitution of primary amine

Preparation of 1-[N-(2-methoxybenzyl)amino]-3-(1H-indol-3-yl)-2-(N-triphenylmethylamino)propane To a mixture of 1-amino-3-(1H-indol-3-yl)-2-(N-triphenylmethylamino)propane (48.68 g, 0.109 mole) dissolved in toluene (1.13 1) was added 2-methoxybenzaldehyde (23.12 g, 0.169 mole), the 2-methoxybenzaldehyde having been previously purified by base wash. The reaction mixture was stirred overnight. The solvents were then removed in vacuo.

The recovered solid was dissolved in 376 ml of a 1:1 tetrahydrofuran:methanol mixture. To this solution was added sodium borohydride (6.83 g, 0.180 mole). This mixture was stirred on ice for about 4 hours. The solvents were removed by evaporation. The remaining liquid was partitioned between 1200 ml of ethyl acetate and 1000 ml of a 1:1 brine:20N sodium hydroxide solution. This was extracted twice with 500 ml of ethyl acetate each and then dried over sodium sulfate. The solvents were then removed by evaporation overnight, yielding 67.60 grams (>99% yield) of the desired product.

Method J

Tritylation

Preparation of 3-(1H-indol-3-yl)-2-(N-triphenylmethylamino)propanoic acid [N-trityltryptophan]

Chlorotrimethylsilane (70.0 ml, 0.527 moles) was added at a moderate rate to a stirring slurry of tryptophan (100.0 g, 0.490 mole) in anhydrous methylene chloride (800 ml) under a nitrogen atmosphere. This mixture was continuously stirred for 4.25 hours. Triethylamine (147.0 ml, 1.055 moles) was added followed by the addition of a solution of triphenylmethyl chloride (147.0 g, 0.552 mole) in methylene chloride (400 ml) using an addition funnel. The mixture was stirred at room temperature, under a nitrogen atmosphere for at least 20 hours. The reaction was quenched by the addition of methanol (500 ml).

The solution was concentrated on a rotary evaporator to near dryness and the mixture was redissolved in methylene chloride and ethyl acetate. An aqueous work-up involving a 5% citric acid solution (2×) and brine (2×) was then performed. The organic layer was dried over anhydrous sodium sulfate, filtered, and concentrated to dryness on a rotary evaporator. The solid was dissolved in hot diethyl ether followed by the addition of hexanes to promote crystallization. By this process 173.6 g (0.389 mole) of analytically pure 3-(1H-indol-3-yl)-2-(N-triphenylmethylamino) propanoic acid was isolated as a light tan solid in two crops giving a total of 79% yield.

Coupling

Preparation of 3-(1H-indol-3-yl)-N-(2-methoxybenzyl)-2-(N-triphenylmethylamino propanamide To a stirring solution of 3-(1H-indol-3-yl)-2-(N-triphenylmethylamino)propanoic acid (179.8 g, 0.403 mole), 2-methoxybenzylamine (56.0 ml, 0.429 mole), and hydroxybenzotriazole hydrate (57.97 g, 0.429 mole) in anhydrous tetrahydrofuran (1.7 L) and anhydrous N,N-dimethylformamide (500 ml) under a nitrogen atmosphere at 0° C., were added triethylamine (60.0 ml, 0.430 mole) and 1-(3-dimethylaminopropyl)-3-ethoxycarbodiimide hydrochloride (82.25 g, 0.429 mole). The mixture was allowed to warm to room temperature under a nitrogen atmosphere for at least 20 hours. The mixture was concentrated on a rotary evaporator and then redissolved in methylene chloride and an aqueous work-up of 5% citric acid solution (2×), saturated sodium bicarbonate solution (2×), and brine (2×) was performed. The organic layer was dried over anhydrous sodium sulfate, filtered, and concentrated to dryness on a rotary evaporator. The title product was then filtered as a pink solid in two lots. Isolated 215.8 g (0.381 mole) of analytically pure material (95% yield).

Reduction

Preparation of 3-(1H-indol-3-yl)-1-[N-(2-methoxybenzyl) amino]-2-(N-triphenylmethylamino)propane Red-Al®, [a 3.4M, solution of sodium bis(2-methoxyethoxy)aluminum hydride in toluene] (535 ml, 1.819 moles), dissolved in anhydrous tetrahydrofuran (400 ml) was slowly added using an addition funnel to a refluxing solution of the acylation product, 3-(1H-indol-3-yl)-N-(2-methoxybenzyl)-2-(N-triphenylmethylamino)propanamide (228.6 g, 0.404 mols) produced supra, in anhydrous tetrahydrofuran (1.0 liter) under a nitrogen atmosphere. The reaction mixture became a purple solution. The reaction was quenched after at least 20 hours by the slow addition of excess saturated Rochelle salt solution (potassium sodium tartrate tetrahydrate). The organic layer was isolated, washed with brine (2×), dried over anhydrous sodium sulfate, filtered, and concentrated to an oil on a rotary evaporator. No further purification was done and the product was used directly in the next step.

Method K

Acylation

Preparation of 3-(1H-indol-3-yl)-1-[N-(2-methoxybenzyl) acetylamino]-2-(N-triphenylmethylamino)propane To a stirring solution of 3-(1H-indol-3-yl)-1-[N-(2-methoxybenzyl)amino]-2-(N-triphenylmethylamino) propane (0.404 mole) in anhydrous tetrahydrofuran (1.2 liters) under a nitrogen atmosphere at 0° C. was added triethylamine (66.5 ml, 0.477 mole) and acetic anhydride (45.0 ml, 0.477 mole). After 4 hours, the mixture was concentrated on a rotary evaporator, redissolved in methylene chloride and ethyl acetate, washed with water (2×) and brine (2×), dried over anhydrous sodium sulfate, filtered, and concentrated to a solid on a rotary evaporator. The resulting solid was dissolved in chloroform and loaded onto silica gel 60 (230–400 mesh) and eluted with a 1:1 mixture of ethyl acetate and hexanes. The product was then crystallized from an ethyl acetate/hexanes mixture. The resulting product of 3-(1H-indol-3-yl)-1-[N-(2-methoxybenzyl)acetylamino]-2-(N-triphenylmethylamino)propane was crystallized and isolated over three crops giving 208.97 grams (87% yield) of analytically pure material.

Method L

Detritylation

Preparation of 2-amino-3-(1H-indol-3-yl)-1-[N-(2-methoxybenzyl)acetylamino]propane Formic acid (9.0 ml, 238.540 mmoles) was added to a stirring solution of 3-(1H-indol-3-yl)-1-[N-(2-methoxybenzyl)acetylamino]-2-(N-triphenylmethylamino) propane (14.11 g, 23.763 mmoles) in anhydrous methylene chloride under a nitrogen atmosphere at 0° C. After 4 hours, the reaction mixture was concentrated to an oil on a rotary evaporator and redissolved in diethyl ether and 1.0N hydrochloric acid. The aqueous layer was washed twice with diethyl ether and basified with sodium hydroxide to a pH greater than 12. The product was extracted out with methylene chloride (4×). The organic extracts were combined, dried over anhydrous sodium sulfate, filtered, and concentrated on a rotary evaporator to a white foam. The compound 2-amino-3-(1H-indol-3-yl)-1-[N-(2-methoxybenzyl) acetylamino]propane (7.52 g, 21.397 mmols) was isolated giving a 90% yield. No further purification was necessary.

Method M

Bromoacetylation

Preparation of 2-[(2-bromo)acetyl]amino-3-(1H-indol-3-yl)-1-[N-(2-methoxybenzyl)acetylamino]propane To a stirring solution of 2-amino-3-(1H-indol-3-yl)-1-[N-(2-methoxybenzyl)acetylamino]propane (7.51 g, 21.369 mmoles) in anhydrous tetrahydrofuran (100 ml) under a nitrogen atmosphere at 0° C. was added diisopropylethylamine (4.1 ml, 23.537 mmoles) and bromoacetyl bromide (2.05 ml, 23.530 mmoles). After 2 hours, ethyl acetate was added and the reaction mixture washed with water twice, 1.0N hydrochloric acid (2×), saturated sodium bicarbonate solution (2×), and brine. The organic layer was dried over anhydrous sodium sulfate, filtered, and concentrated to a tan foam on a rotary evaporator. In this manner the 2-[(2-bromo) acetyl]amino-3-(1H-indol-3-yl)-1-[N-(2-methoxybenzyl) acetylamino]propane was obtained in quantitative yield. No further purification was necessary.

Method N

Nucleophilic Displacement

Preparation of 1-[N-(2-methoxybenzyl)acetylamino]-3-(1H-indol-3-yl)-2-[N-(2-((4-cyclohexyl)piperazin-1-yl)acetyl) amino]propane

[Compound of Example 74]

1-Cyclohexylpiperazine (3.65 g, 22.492 mmoles) was added to a stirring solution of 2-[(2-bromo)acetyl]amino-3-(1H-indol-3-yl)-1-[N-(2 -methoxybenzyl)acetylamino] propane (21.369 mmoles) and powdered potassium carbonate (3.56 g, 25.758 mmols) in methylene chloride under a nitrogen atmosphere. The reaction mixture was stirred overnight at room temperature. The salts were filtered and the solution concentrated to a brown foam on a rotary evaporator. The desired product was purified on a Prep 500 column using a 10 L gradient starting with 100% methylene chloride and ending with 5% methanol/94.5% methylene chloride/ 0.5% ammonium hydroxide. Impure fractions were combined and purified further by reverse phase preparative high performance liquid chromatography (methanol/acetonitrile/ water/ammonium acetate). After combining the material from both chromatographic purifications the title compound (10.43 g, 18.663 mmoles) was isolated (87% yield).

An alternative means of acylation of the primary amine as shown in the final step of the synthesis protocol of Scheme IV is by means of reacting a compound of the formula

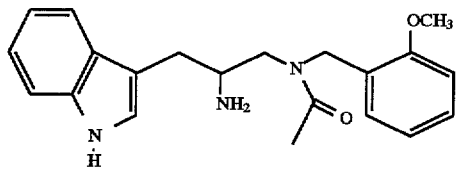

with a potassium carboxylate of the formula

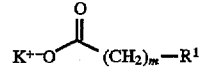

in the presence of isobutylchloroformate and N-methylmorpholine. This reaction is usually performed in the presence of a non-reactive solvent such as methylene chloride at cool temperatures, usually between −30° C. and 10° C., more preferably at temperatures between −20° C. and 0° C. In this reaction equimolar amounts of the two reactants are generally employed although other ratios are operable. An example of this preferred means of acylating the primary amine is shown in the following example.

Method P

Preparation of (R)-1-[N-(2-methoxybenzyl)acetylamino]-3-(1H-indol-3-yl)-2-[N-(2-((4-cyclohexyl)piperazin-1-yl) acetyl)amino]propane

[Compound of Example 75]

The title compound was prepared by first cooling 2-((4-cyclohexyl)piperazin-1-yl)acetic acid potassium salt to a temperature between −8° C. and −15° C. in 5 volumes of anhydrous methylene chloride. To this mixture was then added isobutylchloroformate at a rate such that the temperature did not exceed −8° C. This reaction mixture was then stirred for about 1 hour, the temperature being maintained between −8° C. and −15° C.

To this mixture was then added (R)-2-amino-3-(1H-indol-3-yl)-1-[N-(2-methoxybenzyl)acetylamino]propane dihydrochloride at such a rate that the temperature did not exceed 0° C. Next added to this mixture was N-methyl morpholine at a rate such that the temperature did not exceed 0° C. This mixture was then stirred for about 1 hour at a temperature between −15° C. and −8° C.

The reaction was quenched by the addition of 5 volumes of water. The organic layer was washed once with a saturated sodium bicarbonate solution. The organic phase was then dried over anhydrous potassium carbonate and filtered to remove the drying agent. To the filtrate was then added 2 equivalents of concentrated hydrochloric acid, followed by 1 volume of isopropyl alcohol. The methylene chloride was then exchanged with isopropyl alcohol under vacuum by distillation.

The final volume of isopropyl alcohol was then concentrated to three volumes by vacuum. The reaction mixture was cooled to 20° C. to 25° C. and the product was allowed to crystallize for at least one hour. The desired product was then recovered by filtration and washed with sufficient isopropyl alcohol to give a colorless filtrate. The crystal cake was then dried under vacuum at 50° C.

The following table illustrates many of the compounds produced using essentially the steps described in Schemes I through IV. A person of ordinary skill in the art would readily understand that a certain order of steps must be employed in many instances to avoid reactions other than the one sought. For example, as in the above methods, it is frequently necessary to employ a protecting group in order to block a reaction at a particular moiety.

The abbreviations used in the following table are commonly used in the field and would be readily understood by a practitioner in the field. For exmple, the abbreviation "PH" refers to a phenyl group, "i-Pr" refers to an isopropyl group, "Me" describes a methyl group, "Et" refers to an ethyl group, "t-Bu" describes a tert-butyl group, and the like.

In the following table, the first column gives the example number of the compound. The next columns (may be one, two, or three columns) describe the substitution patterns of the particular example. The column entitled "Mp °C." gives the melting point of the compound if it is a solid or notes the form of the substance at ambient temperature. The next column, entitled "MS", defines the mass of the compound as determined by mass spectroscopy. The following column gives the nuclear magnetic resonance profile of the example compound as synthesized. The final columns give the molecular formula of the example compound as well as its elemental analysis.

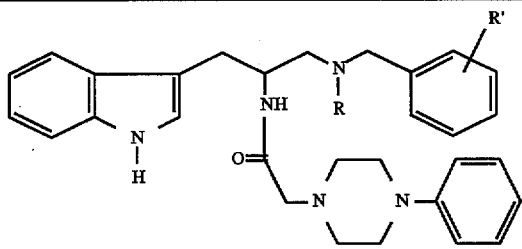

| Example No. | R | R' | Mp °C. | MS | $^1$H NMR | Formula | Analysis % Theory/Found C | H | N |
|---|---|---|---|---|---|---|---|---|---|
| 1 | H | H | foam | 481 (M$^+$) | CDCl$_3$ 2.28(m, 1H), 2.32–2.45(m, 2H), 2.45–2.61(m, 2H), 2.73(m, 1H), 2.79–3.15 (m, 8H), 3.21(m, 1H), 3.96 (ABq, J=8Hz, Δv=20Hz, 2H), 4.50(m, 1H), 6.78–6.99 (m, 3H), 7.04(m, 1H), 7.10–7.59(m, 11H), 7.66(d, J=8 Hz, 1H), 8.10(br s, 1H) | C$_{30}$H$_{35}$N$_5$O | 74.81 74.83 | 7.32 7.38 | 14.54 14.67 |
| 2 | H | 2-Cl | foam | 515, 517 (M$^+$'s for Cl isotopes) | DMSO-d$_6$ 2.33–2.50(m, 4H), 2.56–2.75(m, 2H), 2.75–3.09 (m, 8H), 3.20(m, 1H), 4.78 (s, 2H), 5.21(m, 1H), 6.78 (t, J=8Hz, 1H), 6.88(d, J=8 Hz, 2H), 6.98(t, J=8Hz, 1H), 7.06(t, J=8Hz, 1H), 7.13(m, 1H), 7.13–7.31(m, 4H), 7.34(d, J=7Hz, 1H), 7.39(dd, J=2, 6Hz, 1H), 7.50(dd, J=2, 7Hz, 1H), 7.55(d, J=8Hz, 1H), 7.61 (d, J=7Hz, 1H), 10.81(br s, 1H) | | | | |
| 3 | H | 2-CF$_3$ | foam | 549 (M$^+$) Exact Mass FAB theory: 550.2794 found: | CDCl$_3$ 2.12(m, 1H), 2.36–2.44(m, 2H), 2.44–2.60(m, 2H), 2.77–3.09(m, 10H), 4.02(s, 2H), 4.50(m, 1H), 6.73–7.00(m, 3H), 7.00–7.56 (m, 9H), 7.56–7.85(m, 3H), 8.16(br s, 1H) | C$_{31}$H$_{34}$F$_3$N$_5$O | | | |

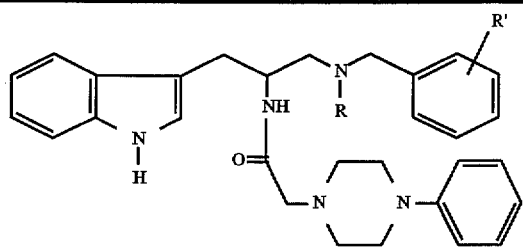

| Example No. | R | R' | Mp °C. | MS | ¹H NMR | Formula | Analysis % Theory/Found C | H | N |
|---|---|---|---|---|---|---|---|---|---|
| 4 | H | 2-OMe (RS) | foam | 550.2801 512 (M+1⁺) | CDCl₃ 2.30–2.43(m, 2H), 2.43–2.54(m, 2H), 2.70–3.10 (m, 11H), 3.82(s, 3H), 3.84 (m, 2H), 4.44(m, 1H), 6.74–6.94(m, 6H), 7.04(m, 1H), 7.07–7.36(m, 7H), 7.64(d, J=8Hz, 1H), 8.04(br s, 1H) | $C_{31}H_{37}N_5O_2$ | 72.77 72.49 | 7.29 7.33 | 13.69 13.90 |
| 5 | H | 2-OMe (R) | foam | 512 (M+1⁺) | CDCl₃ 2.30–2.43(m, 2H), 2.43–2.56(m, 2H), 2.64–3.12 (m, 11H), 3.59–3.93(m, 2H), 3.82(s, 3H), 4.43(m, 1H), 6.68–6.96(m, 6H), 7.03(m, 1H), 7.07–7.45(m, 7H), 7.66 (d, J=8Hz, 1H), 8.04(br s, 1H) | $C_{31}H_{37}N_5O_2$ | 72.77 72.58 | 7.29 7.39 | 13.69 13.65 |
| 6 | H | 2-OMe (S) | foam | 512 (M+1⁺) | CDCl₃ 2.22–2.38(m, 2H) 2.38–2.50(m, 2H), 2.50–3.27 (m, 11H), 3.84(s, 3H), 3.96 (ABq, J=13Hz, Δv=21Hz, 2H), 4.27(m, 1H), 6.75–6.97 (m, 6H), 6.99–7.39(m, 8H), 7.63(d, J=8Hz, 1H), 8.12 (br s, 1H) | $C_{31}H_{37}N_5O_2$ | 72.77 73.01 | 7.29 7.50 | 13.69 13.69 |
| 7 | H | 3-OMe | foam | 511 (M⁺) | CDCl₃ 7:3 mixture of amide rotamers 2.20–3.74(m, 14H), 3.74(m, 1H), 3.76(s, 3/10·3H), 3.80(s, 7/10·3H), 4.13 (ABq, J=14Hz, Δv=50 Hz, 7/10·2H), 4.67(m, 1H), 4.70 (ABq, J=14Hz, Δv=160 Hz, 3/10·2H), 6.82–7.00(m, 6H), 7.00–7.45(m, 8H), 7.59 (d, J=8Hz, 1H), 8.10(br s, 3/10·1H), 8.41(br s, 7/10·1H) | $C_{31}H_{37}N_5O_2$ | 72.77 73.00 | 7.29 7.19 | 13.69 13.91 |
| 8 | H | 4-OMe | foam | 511 (M⁺) | CDCl₃ 2.21–2.63(m, 4H), 2.63–2.90(m, 4H), 2.90–3.40 (m, 6H), 3.75(m, 1H), 3.77 (s, 3H), 4.04 (ABq, J=12Hz, Δv=54Hz, 2H), 4.64(m, 1H), 6.83–6.96(m, 5H), 6.95–7.48(m, 8H), 7.50–7.75(m, 2H), 8,23(br s, 1H) | $C_{31}H_{37}N_5O_2$ | 72.77 72.58 | 7.29 7.35 | 13.69 13.70 |
| 9 | Et | 2-OMe | foam | 540 (M+1⁺) | CDCl₃ 1.04(t, J=8Hz, 3H), 2.32–2.43(m, 2H), 2.43–2.66 (m, 6H), 2.83–2.91(m, 4H), 2.94(d, J=5Hz, 2H), 3.08(t, J=6Hz, 2H), 3.65 (ABq, J=14Hz, Δv=22Hz, 2H), 3.77(s, 3H), 4.41 (q, J=6Hz, 1H), 6.78–6.96(m, 6H), 7.06–7.29(m, 6H), 7.33(d, J=8 Hz, 1H), 7.40(d, J=7Hz, 1H), 7.64(d, J=8Hz, 1H), 7.99(br s, 1H) | $C_{33}H_{41}N_5O_2$ | 73.44 73.21 | 7.66 7.63 | 12.98 13.14 |
| 10 | MeO(OC)CH₂ | 2-OMe | foam | 584 (M+1⁺) | CDCl₃ 2.37–2.47(m, 2H), 2.50–2.58(m, 2H), 2.78–2.98 (m, 6H), 3.00(m, 2H), 3.12(t, J=6Hz, 2H), 3.37 (ABq, J=18Hz, Δv=26Hz, 2H), 3.65(s, 3H), 3.77(s, 3H), | $C_{34}H_{41}N_5O_4$ | 69.96 69.69 | 7.08 6.98 | 11.99 11.87 |

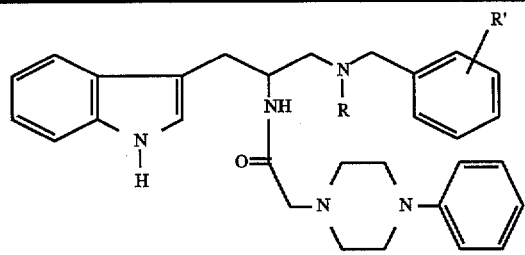

| Example No. | R | R' | Mp °C. | MS | $^1$H NMR | Formula | Analysis % Theory/Found C | H | N |
|---|---|---|---|---|---|---|---|---|---|
| | | | | | 3.83(s, 2H), 4.45(m, 1H), 6.80–6.92(m, 5H), 7.00(s, 1H), 7.10–7.40(m, 8H), 7.70 (d, J=9Hz, 1H), 8.08(s, 1H) | | | | |
| 11 | HO(OC)CH$_2$ | 2-OMe | 95–100 | 570 (M+1$^+$) | DMSO-d$_6$ 2.31–2.49(m, 4H), 2.75(d, J=8Hz, 2H), 2.81–3.05(m, 7H), 3.13–3.49 (m, 3H), 3.65–3.80(m, 2H), 3.71(s, 3H), 4.20(m, 1H), 6.78(t, J=8Hz, 1H), 6.83–6.98(m, 5H), 7.00–7.10(m, 2H), 7.21(t, J=8Hz, 3H), 7.30(t, J=9Hz, 2H), 7.56 (br d, J=8Hz, 2H), 10.81(br s, 1H) | C$_{33}$H$_{39}$N$_5$O$_4$ | 69.57<br>69.80 | 6.90<br>6.79 | 12.29<br>11.99 |
| 12 | MeCO | H | foam | 523 (M$^+$) | DMSO-d$_6$ 1:1 mixture of amide rotamers 1.99(s, 1/2·3H), 2.07(s, 1/2·3H), 2.20–2.50(m, 4H), 2.69–2.95 (m, 4H), 2.95–3.12(m, 4H), 3.12–3.52(m, 1/2·1H+1H), 3.63(m, 1/2·1H), 4.40(m, 1H), 4.51 (ABq, J=16Hz, Δv=140Hz, 1/2·2H), 4.54 (ABq, J=16Hz, Δv=30Hz, 1/2·2H), 6.78(t, J=8Hz, 1H), 6.86–6.94(m, 2H), 6.98 (m, 1H), 7.03–7.15(m, 4H), 7.15–7.38(m, 6H), 7.50–7.60 (m, 1.5H), 7.74(d, J=8Hz, 1/2·1H), 10.93(br s, 1H) | C$_{32}$H$_{37}$N$_5$O$_2$ | 73.39<br>73.67 | 7.12<br>7.23 | 13.37<br>13.60 |
| 13 | MeCO | 2-Cl | foam | 557 (M$^+$) | DMSO-d$_6$ 3:2 mixture of amide rotamers 1.93(s, 2/5·3H), 2.09(s, 3/5·3H), 2.25–2.50(m, 4H), 2.70–2.96 (m, 4H), 2.96–3.19(m, 4H), 3.20–3.64(m, 2H), 4.50(m, 1H), 4.59 (ABq, J=16Hz, Δv=70Hz, 3/5·2H), 4.64(s, 2/5·2H), 6.78(t, J=7Hz, 1H), 6.91(d, J=8Hz, 2H), 6.98(t, J=7Hz, 1H), 7.02–7.10(m, 2H), 7.12(m, 1H), 7.16–7.37(m, 5H), 7.44(m, 1H), 7.50–7.62(m, 2/5·1H+ 1H), 7.75(d, J=8Hz, 3/5·1H), 10.83(br s, 1H) | C$_{32}$H$_{36}$ClN$_5$O$_2$ | 68.86<br>69.06 | 6.50<br>6.48 | 12.55<br>12.56 |
| 14 | MeCO | 2-Me | | 538 (M+1$^+$) | CDCl$_3$ 2.06(s, 3H), 2.21(s, 3H), 2.1–2.6(m, 2H), 2.9–3.3 (m, 12H), 3.58(m, 1H), 4.4–4.6(m, 2H), 6.8–7.0(m, 5H), 7.0–7.4(m, 9H), 7.62(d, J=7 Hz, 1H), 8.15(br s, 1H) | C$_{33}$H$_{39}$N$_5$O$_2$ | 73.71<br>74.00 | 7.31<br>7.37 | 13.02<br>13.21 |
| 15 | MeCO | 2-CF$_3$ | foam | 592 (M+1$^+$) | CDCl$_3$ 2.03(s, 3H), 2.15–2.80(m, 5H), 2.80–3.73 (m. 8H), 3.88(m, 1H), 4.47–4.93 (m, 3H), 6.72–7.03(m, 4H), 7.03–7.45(m, 7H), 7.45–7.76 (m, 4H), 8.22(br s, 1H) | C$_{33}$H$_{39}$F$_3$N$_5$O$_2$ | 66.99<br>66.83 | 6.13<br>6.20 | 11.84<br>12.10 |
| 16 | MeCO | 2-NO$_2$ | foam | 569 (M+1$^+$) | CDCl$_3$ 2.05(s, 3H), 2.28(m, 1H), 2.3–2.7(m, 4H), 2.8–3.2 (m, 8H), 3.2–3.9(m, 2H), | C$_{32}$H$_{36}$N$_6$O$_4$ | 67.59<br>67.32 | 6.38<br>6.35 | 14.78<br>14.56 |

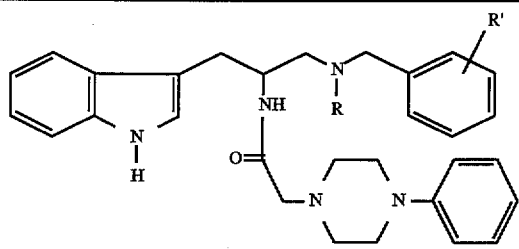

| Example No. | R | R' | Mp °C. | MS | ¹H NMR | Formula | Analysis % Theory/Found C | H | N |
|---|---|---|---|---|---|---|---|---|---|
| | | | | | 4.58(m, 1H), 4.97(m, 1H), 6.8–7.0(m, 2H), 7.0–7.5(m, 10H), 7.5–7.7(m, 2H), 8.12 (d, J=7Hz, 1H), 8.15(br s, 1H) | | | | |
| 17 | MeCO | 2-OMe (RS) | foam | 553 (M⁺) | DMSO-d₆ 3:2 mixture of amide rotamers 1.97(s, 1.8H), 2.07(s, 1.2H), 2.26 – 2.50(m, 4H), 2.70–2.96(m, 4H), 2.96–3.16(m, 4H), 3.16–3.65(m, 2H), 3.72(s, 2/5·3H), 3.74(s, 3/5·3H), 4.40(m, 1H), 4.42 (ABq, J=18Hz, Δv=30Hz, 3/5·2H), 4.46 (ABq, J=16 Hz, Δv=62Hz, 2/5·2H), 6.70–7.03(m, 7H), 7.03–7.13 (m, 2H), 7.13–7.29(m, 3H), 7.34(d, J=8Hz, 1H), 7.49–7.62(m, 3/5H+1H), 7.72(d, J=6Hz, 2/5H), 10.93(br s, 1H) | C₃₃H₃₉N₅O₃ | 71.58 71.50 | 7.10 7.18 | 12.65 12.73 |
| 18 | MeCO | 2-OMe (R) | foam | 553 (M⁺) Exact Mass FAB (M+1): calc.: 554.3131 found:. 654.3144 | CDCl₃ 2.11(s, 3H), 2.41–2.43(m, 2H), 2.50–2.55(m, 2H), 2.87–3.18(m, 9H), 3.78 (s, 3H), 4.02(dd, J=10, 14 Hz, 1H), 4.51 (ABq, J=17 Hz, Δv=42Hz, 2H), 4.59(m, 1H), 6.80–6.98(m, 6H), 7.07–7.45(m, 8H), 7.68(d, J=8 Hz, 1H), 8.14(s, 1H) | C₃₃H₃₉N₅O₃ | 71.58 72.19 | 7.10 7.25 | 12.65 12.93 |
| 19 | MeCO | 2-OMe (S) | foam | 553 (M⁺) | DMSO-d₆ 3:2 mixture of amide rotamers 1.97(s, 3/5·3), 2.07(s, 2/5·3H), 2.23–2.60(m, 4H), 2.71–2.95 (m, 4H), 2.95–3.17(m, 4H), 3.17–3.80(m, 2H), 3.71(s, 3/5·2H), 3.74(s, 3/5·3H), 4.26(m, 1H), 4.44 (ABq, J=16Hz, Δv=26Hz, 3/5·2H), 4.45 (ABq, J=16 Hz, Δv=60Hz, 2/5·2H), 6.70–7.02(m, 7H), 7.02–7.12 (m, 2H), 7.12–7.30(m, 3H) 7.34(d, J=8Hz, 1H), 7.56 (d, J=10Hz, 3/5H+1H), 7.70 (d, J=10Hz, 2/5·1H), 10.82 (br s, 1H) | C₃₃H₃₉N₅O₃ | 71.58 71.62 | 7.10 7.28 | 12.65 12.38 |
| 20 | MeCO | 3-F | 86–88 | 541 (M⁺) | CDCl₃ 2.09(s, 3H), 2.23(m, 1H), 2.3–2.7(m, 2H), 2.7–3.2 (m, 8H), 3.30(m, 1H), 3.60 (m, 1H), 4.02(m, 1H), 4.2–4.7(m, 3H), 6.7–7.0(m, 6H) 7.0–7.5(m, 8H), 7.66(d, J=7 Hz, 1H), 8.16(br s, 1H) | | | | |
| 21 | MeCO | 3-OMe | foam | 553 (M⁺) | CDCl₃ 2.08(s, 3H), 2.15–2.63(m, 4H), 2.72–3.27(m, 8H), 3.75(m, 1H), 3.78(s, 3H), 4.04(m, 1H), 4.51 (ABq, J=16Hz, Δv=46Hz, 2H), 4.56(m, 1H), 6.60–6.70 (m, 2H), 6.72–6.94(m, 5H), | C₃₃H₃₉N₅O₃ | 71.58 71.32 | 7.10 7.01 | 12.65 12.65 |

-continued

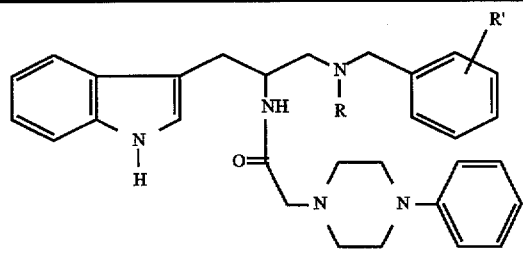

| Example No. | R | R' | Mp °C. | MS | ¹H NMR | Formula | Analysis % Theory/Found C | H | N |
|---|---|---|---|---|---|---|---|---|---|
| 22 | MeCO | 4-OMe | foam | 553 (M⁺) | 7.04–7.46(m, 7H), 7.65(d, J=8Hz, 1H), 8.04(br s, 1H) DMSO-d₆ 1:1 mixture of amide rotamers 2.01(s, 1/2·3H), 2.05(s, 1/2·3H), 2.23–2.60(m, 4H), 2.74–3.30 (m, 8H), 3.69(m, 1H), 3.72 (s, 1/2·3H), 3.74(s, 1/2·3H), 4.23 (ABq, J=16 Hz, Δν=42Hz, 1/2·2H), 4.52 (m, 1H), 4.36 (ABq, J=14 Hz, Δν=164Hz, 1/2·2H), 6.70–7.16(m, 10H), 7.24(m, 2H), 7.35(m, 1H), 7.55(m, 1/2·1H+1H), 7.73(m, 1/2·1H), 10.84(br s, 1H) | $C_{33}H_{39}N_5O_3$ | 71.58 71.85 | 7.10 7.24 | 12.65 12.65 |
| 23 | MeCO | 4-SMe | dec 138 | 569 (M⁺) | CDCl₃ 2.09(s, 3H), 2.1–2.6 (m, 3H), 2.46(s, 3H), 2.8–3.1 (m, 8H), 3.30(m, 1H), 3.55 (m, 1H), 3.98(m, 1H), 4.47 (ABq, J=12Hz, Δν=52Hz, 2H), 4.58(m, 1H), 6.8–6.9 (m, 3H), 6.95(d, J=8Hz, 2H), 7.0–7.4(m, 9H), 7.66(d, J=8Hz, 1H), 8.08(br s, 1H) | $C_{33}H_{39}N_5O_2S$ | 69.57 69.86 | 6.90 6.93 | 12.29 12.33 |
| 24 | HCO | 2-OMe | foam | 540 (M+1) | CDCl₃ 2.33–2.47(m, 2H), 2.50–2.65(m, 2H), 2.87–3.10 (m, 9H), 3.75(s, 3H), 3.77 (m, 1H), 4.40 (ABq, J=15 Hz, Δν=35Hz, 2H), 4.65(m, 1H), 6.75–6.95(m, 6H), 7.03–7.42(m, 8H), 7.67(d, J=9 Hz, 1H), 8.20(br s, 1H), 8.33(s, 1H) | $C_{32}H_{37}N_5O_3$ | 71.21 70.99 | 6.91 6.96 | 12.98 13.25 |
| 25 | BrCH₂CO | 2-OMe | foam | 631, 633 (M⁺'s for Br isotopes) Exact Mass FAB (M+1): calc.: 632.2236 found:. 632:2213 | CDCl₃ 2.37–2.47(m, 2H), 2.53–2.63(m, 2H), 2.90–3.17 (m, 8H), 3.80(s, 3H), 3.95–4.13(m, 2H), 3.98 (ABq, J=11Hz, Δν=61Hz, 2H), 4.57 (ABq, J=18Hz, Δν=80 Hz, 2H), 4.67(m, 1H), 6.78 (d, J=5Hz, 1H), 6.80–6.90 (m, 4H), 7.07(d, J=3Hz, 1H), 7.10–7.30(m, 6H), 7.37 (d, J=8Hz, 1H), 7.50(d, J=10Hz, 1H), 7.70(d, J=9 Hz, 1H), 8.07(s, 1H) | $C_{33}H_{38}BrN_5O_3$ | | | |
| 26 | EtCO | 2-OMe | oil | 568 (M+1⁺) | CDCl₃ 1.12(t, J=9Hz, 3H), 2.38 (q, J=9Hz, 2H), 2.33–2.60(m, 4H), 2.83–3.13(m, 8H), 3.22(br d, J=13Hz, 1H), 3.80(s, 3H), 4.03(br t, J=13Hz, 1H), 4.55 (ABq, J=20Hz, Δν=40Hz, 2H), 4.60(m, 1H), 6.83–6.97(m, 6H), 7.10–7.57(m, 8H), 7.68 (d, J=8Hz, 1H), 8.24(br s, 1H) | $C_{34}H_{41}N_5O_3$ | 71.93 72.17 | 7.28 7.42 | 12.34 12.10 |
| 27 | PhCO | 2-OMe | foam | 615 (M⁺) | CDCl₃ 2.28–2.57(m, 4H), 2.77–3.17(m, 9H), 3.65(s, 3H), 4.22(t, J=13Hz, 1H), 4.60 (ABq, J=15Hz, Δν=30 | $C_{38}H_{41}N_5O_3$ | 74.12 74.38 | 6.71 6.87 | 11.37 11.32 |

-continued

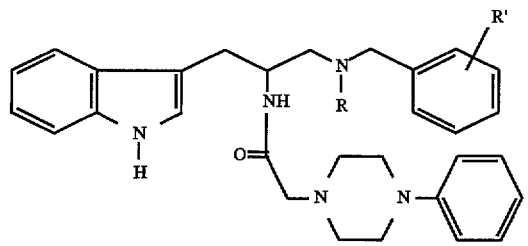

| Example No. | R | R' | Mp °C. | MS | ¹H NMR | Formula | Analysis % Theory/Found C | H | N |
|---|---|---|---|---|---|---|---|---|---|
| 28 | EtOCO | 2-OMe | foam | 584 (M+1) | Hz, 2H), 4.82(m, 1H), 6.70–6.92(m, 5H), 7.02–7.55(m, 14H), 7.98(d, J=7Hz, 1H), 8.22(br s, 1H) DMSO-d₆ 1.05(t, J=8Hz, 3H), 2.31–2.45(m, 4H), 2.73–2.90 (m 4H), 2.93–3.10 (m 4H), 3.22–3.48(m, 2H), 3.66(s, 3H), 3.87–4.03(m, 2H), 4.26–4.55(m, 3H), 6.77 (t, J=7Hz, 1H), 6.80–7.00 (m, 6H), 7.05(t, J=8Hz, 1H), 7.11(br s, 1H), 7.20(t, J=9Hz, 3H), 7.32(d, J=10 Hz, 1H), 7.52(br d, J=6Hz, 2H) | $C_{34}H_{41}N_5O_4$ | 69.96 69.85 | 7.08 7.19 | 12.00 11.98 |
| 29 | MeNHCO | 2-OMe | oil | 568 (M⁺) | DMSO-d₆ 2.32–2.46(m, 4H), 2.55(d, J=5Hz, 3H), 2.78–2.90(m, 4H), 2.96–3.10(m, 4H), 3.18(dd, J=5, 14Hz, 1H), 3.44(dd, J=8, 13Hz, 1H), 3.70(s, 3H), 4.30(m, 1H), 4.37 (ABq, J=18Hz, Δν=42Hz, 2H), 6.32(br d, J=5Hz, 1H), 6.77(t, J=7 Hz, 1H), 6.82–7.00(m, 6H), 7.05(t, J=8Hz, 1H), 7.11(d, J=3Hz, 1H), 7.16–7.25(m, 3H), 7.32(d, J=9Hz, 1H), 7.53(d, J=8Hz, 1H), 7.61 (d, J=9Hz, 1H), 10.82(br s, 1H) | $C_{33}H_{40}N_6O_3$ | 69.69 69.94 | 7.09 7.13 | 14.78 14.83 |
| 30 | MeO(OC)CH₂CO | 2-OMe | foam | 611 (M⁺) | CDCl₃ 2.37–2.47(m, 2H), 2.50–2.60(m, 2H), 2.82–3.18 (m, 9H), 3.57(s, 2H), 3.72 (s, 3H), 3.78(s, 3H), 4.02 (dd, J=10, 14Hz, 1H), 4.47 (ABq, J=20Hz, Δν=40Hz, 2H), 4.60(m, 1H), 6.77–6.92 (m, 6H), 7.03–7.30(m, 6H), 7.37(d, J=7Hz, 1H), 7.45 (d, J=10Hz, 1H), 7.68(d, J=9Hz, 1H), 8.12(s, 1H) | $C_{35}H_{41}N_5O_5$ | 68.72 68.44 | 6.76 6.76 | 11.45 11.44 |
| 31 | HO(OC)CH₂CO | 2-OMe | 103–107 | 598 (M+1⁺) Exact Mass FAB (M+1): calc.: 598.3029 found:. 598.3046 | CDCl₃ 2.68–2.90(m, 4H), 2.90–3.37(m, 9H), 3.57(br s, 2H), 3.78(s, 3H), 3.93(t, J=12Hz, 1H), 4.53 (ABq, J=17Hz, Δν=47Hz, 2H), 4.70(m, 1H), 6.77–6.97(m, 6H), 7.07–7.33(m, 7H), 7.37 (d, J=8Hz, 1H), 7.63(d, J=8 Hz, 1H) 7.85(br s, 1H), 8.33(br s, 1H) | $C_{34}H_{39}N_5O_5$ | | | |
| 32 | Me(CO)OCH₂CO | 2-OMe | foam | 612 (M+1⁺) | CDCl₃ 2.10(s, 3H), 2.35–2.43(m, 2H), 2.47–2.57(m, 2H), 2.90–3.13(m, 9H), 3.80 (s, 3H), 4.03(dd, J=10, 15 Hz, 1H), 4.40 (ABq, J=19 Hz, Δν=30Hz, 2H), 4.57(m, 1H), 4.85 (ABq, J=15Hz, Δν=19Hz, 2H), 6.75–6.90 (m, 6H), 7.03(d, J=2Hz, | $C_{35}H_{41}N_5O_5$ | 68.72 68.50 | 6.76 6.86 | 11.45 11.20 |

-continued

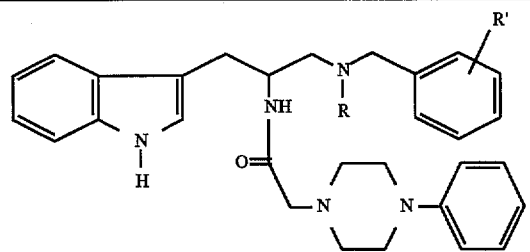

| Example No. | R | R' | Mp °C. | MS | $^1$H NMR | Formula | Analysis % Theory/Found | | |
|---|---|---|---|---|---|---|---|---|---|
| | | | | | | | C | H | N |
| | | | | | 1H), 7.10–7.30(m, 5H), 7.35–7.43(m, 2H), 7.66(d, J=9 Hz, 1H), 8.32(br s, 1H) | | | | |
| 33 | HOCH$_2$CO | 2-OMe | foam | 569 (M$^+$) | CDCl$_3$ 2.35–2.57(m, 4H), 2.80–3.17(m, 9H), 3.52(t, J=5Hz, 1H), 3.75(s, 3H), 4.08(m, 1H), 4.27(dd, J=5, 10Hz, 2H), 4.33(d, J=5Hz, 2H), 4.63(m, 1H), 6.73–6.92 (m, 6H), 7.03(d, J=3Hz, 1H), 7.12–7.32(m, 5H), 7.33–7.40(m, 2H), 7.67(d, J=10 Hz, 1H), 8.07(br s, 1H) | C$_{33}$H$_{39}$N$_5$O$_4$ · 0.5 H$_2$O | 68.49 68.51 | 6.97 6.86 | 12.10 11.91 |
| 34 | H$_2$NCH$_2$CO | 2-OMe | foam | 568 (M$^+$) | CDCl$_3$ 2.20(m, 2H), 2.35–2.45(m, 2H), 2.45–2.53(m, 2H), 2.80–3.07(m, 8H), 3.30 (dd, J=5, 15Hz, 1H), 3.47–3.57(m, 2H), 3.77(s, 3H), 3.93(dd, J=10, 15Hz, 1H), 4.42 (ABq, J=20Hz, Δν=30 Hz, 2H), 4.62(m, 1H), 6.77–6.90(m, 5H), 7.03–7.40(m, 9H), 7.65(d, J=8Hz, 1H), 8.12(br s, 1H) | C$_{33}$H$_{40}$N$_6$O$_3$ | 69.69 69.82 | 7.09 7.14 | 14.78 14.49 |
| 35 | Me$_2$NCH$_2$CO | 2-OMe | foam | 596 (M$^+$) | CDCl$_3$ 2.30(s, 6H), 2.32–2.50(m, 4H), 2.87–3.05(m, 8H), 3.20(s, 2H), 3.33(dd, J=6, 9Hz, 1H), 3.78(s, 3H), 3.85(m, 1H), 4.58(m, 1H) 4.65 (ABq, J=18Hz, Δν=42 Hz, 2H), 6.81–6.93(m, 6H), 7.10–7.40(m, 8H), 7.65(d, J=11Hz, 1H), 8.17(br s, 1H) | C$_{35}$H$_{44}$N$_6$O$_3$ | 70.44 70.15 | 7.43 7.39 | 14.08 14.02 |
| 36 | t-Bu—O(CO)NH—CH$_2$CO | 2-OMe | foam | 668 (M$^+$) | CDCl$_3$ 1.43(s, 9H), 2.33–2.57(m, 4H), 2.82–3.12(m, 8H), 3.17(dd, J=5, 15Hz, 1H), 3.77(s, 3H), 3.93–4.10 (m, 3H), 4.42 (ABq, J=18 Hz, Δν=41Hz, 2H), 4.60(m, 1H), 5.50(br s, 1H), 6.73–6.92(m, 6H), 7.05(s, 1H), 7.08–7.32(m, 5H), 7.35(d, J=10Hz, 2H), 7.65(d, J=10 Hz, 1H), 8.10(br s, 1H) | C$_{38}$H$_{48}$N$_6$O$_5$ | 68.24 68.44 | 7.23 7.50 | 12.57 12.61 |
| 37 | MeSO$_2$ | 2-OMe | foam | 589 (M$^+$) | DMSO-d$_6$ 2.28–2.46(m, 4H), 2.83(d, J=7Hz, 4H), 2.90(s, 3H), 2.98–3.04(m, 4H), 3.26–3.34(m, 2H), 3.67(s, 3H), 4.30(m, 1H), 4.36(d, J=5 Hz, 2H), 6.77(t, J=8Hz, 1H), 6.84–6.92(m, 3H), 6.92–7.00(m, 2H), 7.03–7.09(m, 2H), 7.18–7.30(m, 4H), 7.33 (d, J=8Hz, 1H), 7.46(d, J=8 Hz, 1H), 7.54(d, J=9Hz, 1H), 10.82(br s, 1H) | C$_{32}$H$_{39}$N$_5$O$_4$S | 65.17 64.88 | 6.67 6.72 | 11.88 11.60 |

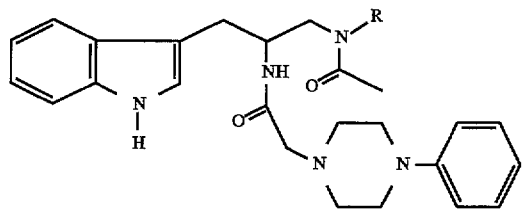

| Example No. | R | Mp °C. | MS | ¹H NMR | Formula | Analysis Theory/Found C | H | N |
|---|---|---|---|---|---|---|---|---|
| 38 | Me | 128-129 | 447 (M+) | CDCl₃ 2.07(s, 3H), 2.38-2.78(m, 3H), 2.8-3.3(m, 11H), 3.42(m, 1H), 3.67(m, 1H), 3.95(m, 1H), 4.58(m, 1H), 6.8-7.0(m, 3H), 7.1-7.4(m, 7H), 7.68(d, J=7Hz, 1H), 8.21(br s, 1H) | C₂₆H₃₃N₅O₂ | 69.77 69.59 | 7.43 7.52 | 15.65 15.65 |
| 39 | n-Bu | foam | 489 (M+) | ¹H CDCl₃ 0.88(t, J=6Hz, 3H), 1.1-1.40 (m, 2H), 1.4-1.6(m, 2H), 2.08(s, 3H), 2.2-2.4(m, 4H), 2.8-3.1(m, 8H), 3.1-3.4(m, 3H), 3.9(m, 1H), 4.5(br s, 1H), 6.8-7.0(m, 3H), 7.0-7.5(m, 7H), 7.68(d, J=6Hz, 1H), 8.31(br s, 1H). | C₂₉H₃₉N₅O₂ | 71.13 71.40 | 8.03 8.05 | 14.30 14.41 |
| 40 | n-Hex | foam | 517 (M+) | ¹H CDCl₃ 0.82-0.92(m, 3H), 1.12-1.36(m, 6H), 1.40-1.70(m, 3H), 2.05(s, 3H), 2.31-2.61(m, 3H), 2.80-3.11(m, 8H), 3.11-3.42 (m, 3H), 3.9(m, 1H), 4.5(m, 1H), 6.75-6.98(m, 3H), 7.08-7.48(m, 7H), 7.7(m, 1H), 8.1(br s, 1H). | C₃₁H₄₃N₅O₂ | 71.92 71.85 | 8.37 8.35 | 13.53 13.59 |
| 41 | (c-hexyl)CH₂ | foam | 530 (M+1+) | CDCl₃ 0.65-1.02(m, 2H), 1.02-1.36(m, 3H), 1.36-1.87(m, 9H), 2.07(s, 3H), 2.15-3.70 m, 12H), 3.95(m, 1H), 4.57(m, 1H), 6.70-7.03(m, 4H), 7.03-7.23(m, 4H), 7.31-7.44(m, 2H), 7.69(d, J=10Hz, 1H), 8.16 (br s, 1H) | C₃₂H₄₃N₅O₂ | 72.56 72.46 | 8.18 8.12 | 13.22 13.07 |
| 42 | Ph | 183-184 | 509 (M+) | ¹H DMSO 1.71(s, 3H), 2.23-2.43(m, 4H), 2.71-2.94(m, 4H), 2.94-3.10(m, 4H), 3.61 (m, 1H), 4.03(m, 1H), 4.24(m, 1H), 6.77 (t, J=8Hz, 1H), 6.92-6.99(m, 3H), 6.99-7.12(m, 2H), 7.21(t, J=8Hz, 2H), 7.24-7.35(m, 3H), 7.4(m, 1H), 7.40-7.54(m, 4H), 10.92(br s, 1H). | C₃₁H₃₅N₅O₂ | 73.04 73.30 | 6.92 7.11 | 13.74 13.73 |
| 43 | PhCH₂CH₂ | | 537 (M+) | ¹H DMSO (3:2 mixture of amide rotamers)1.69(s, 3/5·3H)2.00(s, 2/5·3H), 2.50-2.60(m, 5H, 2.70-3.05(m, 5H), 3.05-3.19(m, 4H), 3.19-3.36(m, 2H), 3.36-3.64(m, 2H), 4.32(m, 1H), 6.76(t, J=8Hz, 1H), 6.90(d, J=8Hz, 2H), 6.95-7.39(m, 11H), 7.56(m, 1H), 7.76(m, 2/5·1H), 7.92(m, 3/5·1H), 10.81(br s, 2/5·1H), 10.85(br s, 3/5·1H). | C₃₃H₃₉N₅O₂ | 73.71 73.95 | 7.31 7.45 | 13.02 13.07 |

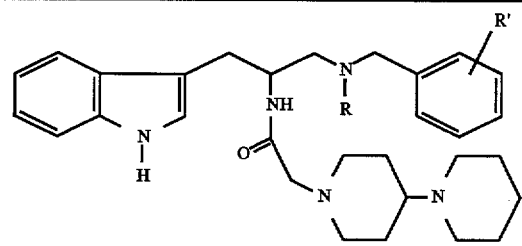

| Example No. | R | R' | Mp °C. | MS | ¹H NMR | Formula | Analysis % Theory/Found C | H | N |
|---|---|---|---|---|---|---|---|---|---|
| 44 | H | 2-OMe (R) | foam | 517 (M+) | CDCl₃ 1.10-2.18 (m, 12H), 2.18-3.18(m, 14H), 3.61-3.95(m, 2H), | C₃₁H₄₃N₅O₂ | 71.92 71.69 | 8.37 8.25 | 13.53 13.26 |

-continued

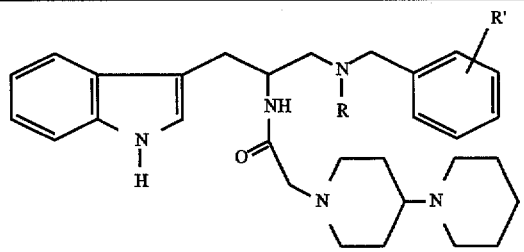

| Example No. | R | R' | Mp °C. | MS | ¹H NMR | Formula | Analysis % Theory/Found | | |
|---|---|---|---|---|---|---|---|---|---|
| | | | | | | | C | H | N |
| | | | | | 3.93(s, 3H), 4.36 (m, 1H), 6.76–6.96 (m, 3H), 7.04–7.44 (m, 5H), 7.42(d, J=8Hz, 1H), 7.65 (d, J=8Hz, 1H), 9.13(br s, 1H) | | | | |
| 45 | H | 2-OMe (S) | foam | 517 (M⁺) | CDCl₃ 1.13–2.18 (m, 12H), 2.18–3.33(m, 14H), 3.61–3.96(m, 2H), 3.85(s, 3H), 4.36 (m, 1H), 6.80–6.97 (m, 3H), 6.97–7.36 (m, 6H), 7.44(d, J=8Hz, 1H), 9.60 (br s, 1H) | $C_{31}H_{43}N_5O_2$ | 71.92 71.91 | 8.37 8.25 | 13.53 13.42 |
| 46 | MeCO | H | foam | 530 (M+1⁺) | CDCl₃ 3:1 mixture of amide rotamers 1.21–1.69(m, 10H), 1.90–2.19(m, 3H), 2.07(s, 3/4·3H), 2.10 (s, 1/4·3H), 2.37–2.55(m, 5H), 2.65–3.18(m, 6H), 4.02(dd, J=13 Hz, J=10Hz, 1H), 4.50(ABq, J=17Hz, Δv=52Hz, 3/4·2H), 4.67(ABq, J=17Hz, Δv=228Hz, 1/4·2H), 4.55 (m, 1H), 6.94–7.44(m, 10H), 7.65 (d, J=8Hz, 3/4·1H), 7.53(d, J=8 Hz, 1/4·1H), 8.08(br s, 3/4·1H), 8.22(br s, 1/4·1H). | $C_{32}H_{43}N_5O_2$ | 72.56 72.36 | 8.18 8.17 | 13.22 13.12 |
| 47 | MeCO | 2-Cl (RS) | foam | 563 (M⁺) Exact Mass FAB theory: 564.3105 found: 564.3130 (M⁺¹) | CDCl₃ 1.17–1.80(m, 10H), 190–2.27(m, 3H), 2.03(s, 3H), 2.35–2.59 (m, 5H), 2.67–3.23(m, 6H), 3.97 (dd, J=10, 15Hz, 1H), 4.53(m, 1H), 4.58(ABq, J=17Hz, Δv=21Hz, 2H), 6.95–7.29(m, 6H), 7.34(d, J=8 Hz, 2H), 7.42(d, J=9Hz, 1H), 7.63 (d, J=8Hz, 1H), 8.19(br s, 1H) | $C_{32}H_{42}ClN_5O_2$ | | | |
| 48 | MeCO | 2-Cl (R) | foam | 563 (M⁺) | ¹H CDCl₃ 1.1–1.8(m, 10H), 1.8–2.3 (m, 4H), 2.04(s, 3H), 2.4–2.6(m, 3H), 2.6–2.8(m, 2H), 2.8–2.9(m, 2H), 2.9–3.1(m, 2H), 3.2(m, 1H), 3.9(m, 1H), 4.5–4.7(m, 3H), 7.0–7.6 (m, 9H), 7.62(d, J=6Hz, 1H), 8.32 (br s, 1H). | $C_{32}H_{42}ClN_5O_2$ | 68.13 68.20 | 7.50 7.60 | 12.41 12.17 |
| 49 | MeCO | 2-Cl (S) | foam | 563 (M⁺) | ¹H CDCl₃ 1.3–1.8(m, 6H), 2.04(s, 3H), 1.8–2.1(m, 3H), 2.1–2.3(m, 3H), 2.4–2.6(m, 5H), 2.7–2.8(m, 2H), 2.86(d, J=2Hz, 2H), 2.9–3.1 (m, 2H), 3.2(m, 1H), 3.9(m, 1H), 4.5–4.7(m, 3H), 7.0–7.5(m, 9H), 7.63(d, J=7Hz, 1H), 8.38(br s, 1H) | $C_{32}H_{42}ClN_5O_2$ | 68.13 68.40 | 7.50 7.61 | 12.41 12.60 |
| 50 | MeCO | 2-OMe (RS) | foam | 559 (M⁺) | CDCl₃ 1.30–1.86(m, 10H), 1.93–2.32(m, 3H), 2.10(s, 3H), 2.45–2.67(m, 4H), 2.71–3.18(m, 5H), 2.87(s, 2H), 3.76(s, 3H), 3.99 (dd, J=14Hz, J=10Hz, 1H), 4.49, (ABq, J=17Hz, Δv=41Hz, 2H), 4.55(m, 1H), 6.79–6.93(m, 3H), 7.06–7.27(m, 4H), 7.36(d, J=8 Hz, 1H), 7.45(d, J=9Hz, 1H), 7.66(d, J=8 Hz, 1H), 8.28(br s, 1H) | $C_{33}H_{45}N_5O_3$ | 70.81 70.95 | 8.10 8.05 | 12.51 12.45 |
| 51 | MeCO | 2-OMe (R) | | 559 (M+) | DMSO-d₆ 3:2 mixture of amide rotamers, 1.25–1.70(m, 10H), 1.77–2.00(m, 2H), 1.95 (s, 3/5·3H), 2.04(s, 2/5·3H), 2.10–2.97 | $C_{33}H_{45}N_5O_3$ | 70.81 70.57 | 8.10 8.05 | 12.51 12.39 |

-continued

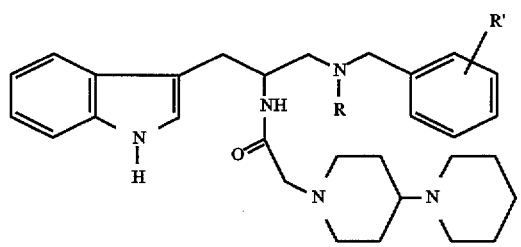

| Example No. | R | R' | Mp °C. | MS | $^1$H NMR | Formula | Analysis % Theory/Found | | |
|---|---|---|---|---|---|---|---|---|---|
| | | | | | | | C | H | N |
| | | | | | (m, 9H), 3.10–3.65(m, 3H), 3.72(s, 2/5·3H), 3.74(s, 3/5·3H), 4.26–4.58(m, 3H), 6.76–7.12(m, 6H), 7.13–7.35(m, 2H), 7.42–7.66(m, 2H), 10.80(br s, 1H) | | | | |
| 52 | MeCO | 2-OMe (S) | | 559 (M$^+$) | DMSO-d$_6$ 3:2 mist. of amide rotamers, 1.15–1.68(m, 10H), 1.68–2.20(m, 3H), 1.95(s, 3/5·3H), 2.04(s, 2/5·3H), 2.20–3.00(m, 9H), 3.00–3.65(m, 3H), 3.74(s, 2/5·3H), 3.76(s, 3/5·3H), 4.20–4.60(m, 3H), 6.75–7.15(m, 6H), 7.15–7.40(m, 2H), 7.40–7.68 (m, 2H), 10.78(br s, 1H) | C$_{33}$H$_{45}$N$_5$O$_3$ | 70.81 71.01 | 8.10 8.39 | 12.51 12.63 |

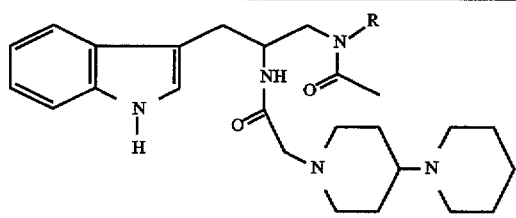

| Example No. | R | Mp °C. | MS | $^1$H NMR | Formula | Analysis % Theory/Found | | |
|---|---|---|---|---|---|---|---|---|
| | | | | | | C | H | N |
| 53 | Ph | 140–141 | 515 (M$^+$) | $^1$H DMSO 1.21–1.58(m, 10H), 1.70(s, 3H), 1.87(ABq, J=8Hz, Δv=20Hz, 2H), 2.04(m, 1H), 2.29–2.49(m, 4H), 2.45–2.64(m, 2H), 2.63–2.79(m, 2H), 2.79–2.95(m, 2H), 3.58(m, 1H), 4.02(t, J=12 Hz, 1H), 4.20(m, 1H), 6.93(t, J=8Hz, 1H), 6.98–7.11(m, 2H), 7.17–7.53(m, 8H), 10.91(br s, 1H). | C$_{31}$H$_{41}$N$_5$O$_2$ | 72.20 71.98 | 8.01 8.07 | 13.58 13.53 |
| 54 | PhCH$_2$CH$_2$ | foam | 543 (M$^+$) | $^1$H DMSO (3:2 mixture amide rotamers)1.23–1.57(m, 10H), 1.75–1.97 (m, 2H), 1.84(s, 3/5·3H), 1.93(s, 2/5·3H), 2.05(m, 1H), 2.23–2.47(m, 4H), 2.50–2.77(m, 6H), 2.77–2.95(m, 2H), 3.20–3.35(m, 1H), 3.36–3.52(m, 2H), 3.62(m, 1H), 4.39(m, 1H), 6.97(m, 1H), 7.02–7.31(m, 7H), 7.34(d, J=8Hz, 1H), 7.45(d, J=8Hz, 3/5H), 7.53–7.67 (m, 2/5·1H+1H), 10.84(br s, 1H). | C$_{33}$H$_{45}$N$_5$O$_2$ | 72.89 72.60 | 8.34 8.29 | 12.88 12.64 |

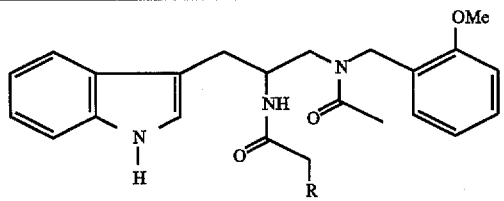

| Example No. | R | Mp, °C. | MS | ¹H NMR | Formula | Analysis, % Theory/Found C | H | N |
|---|---|---|---|---|---|---|---|---|
| 55 | Br (R) | foam | 473 (M+) | CDCl₃ 2.15(s, 3H), 2.81–2.96(m, 2H), 3.15(AB$_q$, J=4.3Hz, Δν=14.6 Hz, 1H), 3.72(s, 3H), 3.79(s, 2H), 4.06–4.15(m, 1H), 4.30(m, 1H), 4.38(AB$_q$, J=16.7Hz, Δν=49.0Hz, 2H), 6.72–6.81(m, 3H), 7.01(s, 1H), 7.13–7.30(m, 3H), 7.35–7.41 (m, 2H), 7.71(d, J=7.8Hz, 1H), 8.04.1H). | $C_{23}H_{26}N_3O_32Br$ | 58.48 58.69 | 5.55 5.66 | 8.90 8.94 |
| 56 | PhO | foam | 485 (M⁺) | CDCl₃ 2.00(s, 3H), 2.86(dd, J=8, 14Hz, 1H), 3.01(dd, J=5, 14Hz, 1H), 3.20(dd, J=5, 15Hz, 1H), 3.70 (s, 3H), 4.04(dd, J=10, 14Hz, 1H), 4.34(ABq, J=18Hz, Δν=44Hz, 2H), 4.44(ABq, J=15Hz, Δν=25Hz, 2H), 4.42(m, 1H), 6.70–6.85(m, 3H), 6.85–7.06(m, 4H), 7.06–7.45(m, 6H), 7.54(m, 1H), 7.71(d, J=8Hz, 1H), 7.97(br s, 1H) | $C_{29}H_{31}N_3O_4$ | 71.73 71.48 | 6.43 6.59 | 8.65 8.46 |
| 57 | PhS | foam | 501 (M⁺) | CDCl₃ 1.92(s, 3H), 2.76(dd, J=8, 14Hz, 1H), 2.92(dd, J=4, 14Hz, 1H), 3.06(dd, J=4, 14 Hz, 1H), 3.57(s, 2H), 3.69(s, 3H), 3.99(dd, J=8, 14Hz, 1H), 4.29(ABq, J=16Hz, Δν=44 Hz, 2H), 4.36(m, 1H), 6.65(m, 3H), 6.85(d, J=3Hz, 1H), 7.05–7.37(m, 9H), 7.42(m, 1H), 7.67(d, J=8Hz, 1H), 7.85 (br s, 1H) | $C_{29}H_{31}N_3O_3S$ | 69.44 69.55 | 6.23 6.49 | 8.38 8.10 |
| 58 | PhNHCH₂CH₂NH | foam | 528 (M + 1⁺) | CDCl₃ 2.11(s, 3H), 2.72–2.95 (m, 4H), 3.00–3.34(m, 6H), 3.72(s, 3H), 4.14(dd, J=11, 13 Hz, 1H), 4.40(ABq, J=17Hz, Δν=63Hz, 2H), 4.42(m, 1H), 4.78(br s, 1H), 6.65–6.84(m, 6H), 6.95(d, J=3Hz, 1H), 7.07–7.35(m, 6H), 7.67(d, J=8 Hz, 1H), 7.80–7.91(m, 2H). | $C_{31}H_{37}N_5O_3$ | 70.56 70.35 | 7.07 7.03 | 13.27 13.06 |
| 59 | 1-pyrrolidinyl | foam | 463 (M + 1⁺) | CDCl₃ 1.66–1.74(m, 4H), 2.11 (s, 3H), 2.47(m, J=19Hz, 4H), 2.86–3.17(m, 5H), 3.74(s, 3H), 4.00(dd, J=11, 14Hz, 1H), 4.46(ABq, J=17Hz, Δν=46 Hz, 2H), 4.52(br s, 1H), 6.76–6.83(m, 2H), 7.08–7.28(m, 3H), 7.18(s, 1H), 7.35(d, J=8 Hz, 1H), 7.52(d, J=8Hz, 1H), 7.69(d, J=8Hz, 1H), 8.38(br s, 1H) | $C_{27}H_{34}N_4O_3$ | 70.10 70.42 | 7.41 7.29 | 12.11 11.75 |
| 60 | 1-piperidinyl | foam | 476 (M⁺) | CDCl₃ 1.37–1.56(m, 6H), 2.09 (s, 3H), 2.30(br s, 4H), 280–3.19(m, 5H), 3.75(s, 3H), 3.95 (dd, J=11, 13Hz, 1H), 4.46 (ABq, J=17Hz, Δν=44Hz, 2H), 4.53(m, 1H), 6.75–6.88 (m, 3H), 7.04–7.24(m, 5H), 7.34(d, J=8Hz, 1H), 7.68(d, J=7Hz, 1H), 8.04(br s, 1H) | $C_{28}H_{36}N_4O_3$ | 70.56 70.68 | 7.61 7.70 | 11.58 11.58 |
| 61 | 1-hexamethyleneiminyl | foam | 490 (M⁺) | CDCl₃ 1.52(br s, 8H), 2.09(s, 3H), 2.54(br s, 4H), 2.87–3.10 (m, 4H), 3.21(dd, J=5, 13Hz, 1H), 3.76(s, 3H), 3.92(dd, J=10, 13Hz, 1H), 4.48(ABq, J=17Hz, Δν=41Hz, 2H), 4.53 (m, 1H), 6.73–6.89(m, 3H), | $C_{29}H_{38}N_4O_3$ | 70.99 71.27 | 7.81 7.98 | 11.42 11.39 |

-continued

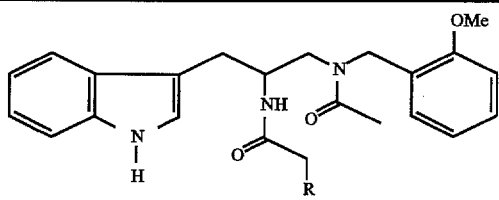

| Example No. | R | Mp, °C. | MS | ¹H NMR | Formula | Analysis, % Theory/Found C | H | N |
|---|---|---|---|---|---|---|---|---|
| 62 | 4-morpholinyl | foam | 478 (M⁺) | 7.04–7.25(m, 4H), 7.34(d, J=6 Hz, 1H), 7.58(m, 1H), 7.66(d, J=7Hz, 1H), 8.04(br s, 1H) CDCl₃ 2.07(s, 3H), 2.20–2.29 (m, 2H), 2.31–2.41(m, 2H), 2.85–2.97(m, 3H), 3.01–3.13 (m, 2H), 3.46–3.67(m, 4H), 3.77(s, 3H), 4.15(dd, J=10, 13 Hz, 1H), 4.47(ABq, J=17Hz, Δν=48Hz, 2H), 4.52(m, 1H), 6.77–6.89(m, 3H), 7.02–7.28 (m, 4H), 7.36(d, J=6Hz, 1H), 7.46(d, J=8Hz, 1H), 7.68(d, J=7Hz, 1H), 8.02(br s, 1H) | $C_{27}H_{34}N_4O_4$ | 67.76 67.54 | 7.16 7.18 | 11.71 11.58 |
| 63 | 1-indolinyl | foam | 510 (M⁺) | CDCl₃ 1.85(s, 3H), 2.85–3.41 (m, 7H), 3.60(ABq, J=17Hz, Δν=42Hz, 2H), 3.73(s, 3H), 4.00(dd, J=12, 13Hz, 1H), 4.38 (ABq, J=17Hz, Δν=48Hz, 2H), 4.43–4.48(m, 1H), 6.32(d, J=8 Hz, 1H), 6.76(m, 3H), 6.97–7.24(m, 7H), 7.35(d, J=8Hz, 1H), 7.54(d, J=8Hz, 1H), 7.70 (d, J=8Hz, 1H), 7.99(br s, 1H) | $C_{31}H_{34}N_4O_3$ | 72.92 73.21 | 6.71 6.54 | 10.97 11.03 |
| 64 | 1,2,3,4-tetrahydroisoquinolin-4-yl | foam | 524 (M⁺), 525 (M + 1⁺) | CDCl₃ 2.06(s, 3H), 2.61–3.28 (m, 9H), 3.48–3.94(m, 3H), 3.77 (s, 3H), 4.50(ABq, J=17Hz, Δν=36Hz, 2H), 4.57(m, 1H), 6.78–6.92(m, 4H), 6.98–7.26(m, 8H), 7.34(d, J=9Hz, 1H), 7.62 (d, J=8Hz, 1H), 7.98(br s, 1H) | $C_{32}H_{36}N_4O_3$ | 73.26 73.31 | 6.92 6.95 | 10.68 10.43 |
| 65 | 1-(4-Ph-piperidinyl) | foam | 552 (M⁺) | CDCl₃ 1.50–1.91(m, 4H), 2.08 (s, 3H), 2.06–2.22(m, 2H), 2.40 (m, 1H), 2.64(br d, J=11Hz, 1H), 2.80(br d, J=12Hz, 1H), 2.86–2.98 (m, 3H), 3.04–3.18(m, 2H), 3.73 (s, 3H), 4.01(dd, J=10, 14Hz, 1H), 4.46(ABq, J=17Hz, , Δν=45Hz, 2H), 4.54(m, 1H), 6.76–6.85(m, 3H), 7.02–7.36(m, 10H), 7.54(d, J=8Hz, 1H), 7.70(d, J=8Hz, 1H), 8.01(br s, 1H) | $C_{34}H_{40}N_4O_3$ | 73.89 73.69 | 7.30 7.25 | 10.14 10.31 |
| 66 | 1-(4-Me₂N-piperidinyl) | foam | 519 (M⁺) | CDCl₃ 1.26(m, 1H), 1.48–1.76 (m, 3H), 1.90–2.11(m, 3H), 2.09 (s, 3H), 2.25(s, 6H), 2.51(br d, J=13Hz, 1H), 2.73(br d, J=12Hz, 1H), 2.85(s, 2H), 2.85–3.23(m, 3H), 3.75(s, 3H), 3.94(dd, J=10, 14Hz, 1H), 4.47(ABq, J=17Hz, Δν=43Hz, 2H), 4.51(m, 1H), 6.77–6.88(m, 3H), 7.01–7.28(m, 4H), 7.35(d, J=8Hz, 1H), 7.41(d, J=9Hz, 1H), 7.66(d, J=7Hz, 1H), 8.09(br s, 1H) | $C_{30}H_{41}N_5O_3$ | 69.34 69.58 | 7.95 8.01 | 13.48 13.52 |
| 67 | 1-(4-Ph-Δ³-piperidinyl) | foam | 550 (M⁺) | CDCl₃ 2.12(s, 3H), 2.21–2.70(m, 4H), 2.90–3.25(m, 7H), 3.77(s, 3H), 3.95(dd, J=10, 14Hz, 1H), 4.52(ABq, J=17Hz, Δν=38Hz, 2H), 4.61(m, 1H), 5.95(br s, 1H), 6.85(m, 3H), 7.00–7.54(m, 11H), 7.67(d, J=8Hz, 1H), 8.08(br s, 1H) | $C_{34}H_{38}N_4O_3$ | 73.06 73.03 | 6.87 6.95 | 9.99 10.03 |
| 68 | 1-(4-AcNH-4-Ph-piperidinyl) | foam | 609 (M⁺) | ¹H CDCl₃ 1.87–2.50(m, 7H), 2.00(s, 3H), 2.07(s, 3H), 2.60(m, 1H), 2.87–3.19(m, 5H), 3.73(s, 3H), 4.06(dd, J=10, 14Hz, 1H), | $C_{36}H_{43}N_5O_4$ | 70.91 70.68 | 7.11 7.13 | 11.48 11.49 |

-continued

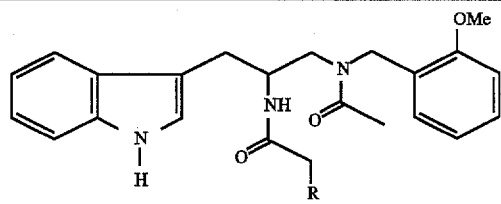

| Example No. | R | Mp, °C. | MS | ¹H NMR | Formula | C | H | N |
|---|---|---|---|---|---|---|---|---|
| 69 | 1-(4-(4-Cl—Ph)-piperazinyl) | foam | 587 (M⁺) | 4.46(ABq, J=17Hz, Δv=47Hz, 2H), 4.52(m, 1H), 5.43(br s, 1H), 6.75–6.90(m, 3H), 7.04–7.48(m, 10H), 7.56(d, J=8Hz, 1H), 7.69(d, J=8Hz, 1H), 8.10(br s, 1H). CDCl₃ 2.11(s, 3H), 2.20–2.42 (m, 2H), 2.42–2.58(m, 2H), 2.82–3.20(m, 9H), 3.76(s, 3H), 4.01(m, 1H), 4.50(ABq, J=16Hz, Δv=42Hz, 2H), 4.54(m, 1H), 6.68–6.90(m, 5H), 7.04–7.32(m, 6H), 7.35(d, J=8Hz, 1H), 7.40(m, 1H), 7.66(d, J=9Hz, 1H), 8.03(br s, 1H) | $C_{33}H_{38}N_5O_3Cl$ | 67.39<br>67.10 | 6.51<br>6.77 | 11.91<br>12.11 |
| 70 | 1-(4-(3-CF₃—Ph)-piperazinyl) | foam | 621 (M⁺) | CDCl₃ 2.10(s, 3H), 2.28–2.42 (m, 2H), 2.42–2.56(m, 2H), 2.84–3.20(m, 9H), 3.77(s, 3H), 4.01(m, 1H), 4.49(ABq, J=18Hz, Δv=42Hz, 2H), 4.56(m 1H), 6.76–6.90(m, 3H), 6.90–7.27(m, 7H), 7.28–7.46(m, 3H), 7.66(d, J=7Hz, 1H), 8.06(br s, 1H) | $C_{34}H_{38}N_5O_3F_3$ | 65.69<br>65.47 | 6.16<br>6.28 | 11.27<br>11.34 |
| 71 | 1-(4-Me-piperazinyl) | foam | 492 (M + 1⁺) | CDCl₃ 2.09(s, 3H), 2.11–2.52 (m, 11H), 2.82–2.97(m, 3H), 2.99–3.15(m, 2H), 3.75(s, 3H), 4.01(dd, J=11, 14Hz, 1H), 4.45(ABq, J=16Hz, Δv=46Hz, 2H), 4.51(m, 1H), 6.76–6.88(m, 3H), 7.02–7.24 (m, 4H), 7.34(d, J=8Hz, 1H), 7.41 (d, J=8Hz, 1H), 7.68(d, J=8Hz, 1H), 8.01(br s, 1H) | $C_{28}H_{37}N_5O_3$<br>Exact Mass Data (M + 1)<br>Calc'd: 492.2975<br>Meas: 492.2977 | | | |
| 73 | 1-(4-i-Pr-piperazinyl) | foam | 519 (M⁺) | CDCl₃ 1.07(br d, J=6Hz, 6H), 2.08 (s, 3H), 2.20–2.80(m, 9H), 2.83–3.16(m, 5H), 3.77(s, 3H), 4.00(dd, J=10, 14Hz, 1H), 4.47(ABq, J=8Hz, Δv=42Hz, 2H), 4.53(m, 1H), 6.73–6.94(m, 3H), 6.94–7.30(m, 4H), 7.30–7.42(m, 2H), 7.65(d, J=10Hz, 1H), 8.06(br s, 1H) | $C_{30}H_{41}N_5O_3$ | 69.34<br>69.60 | 7.95<br>8.09 | 13.48<br>13.49 |
| 74 | 1-(4-cyclohexyl-piperazinyl) (RS) | foam | 559 (M⁺) | CDCl₃ 1.05–1.34(m, 6H), 1.55–1.95(m, 4H), 2.09(s, 3H), 2.20–2.60(m, 9H), 2.90(s, 2H), 2.85–3.16(m, 3H), 3.77(s, 3H), 4.02(dd, J=11, 13Hz, 1H), 4.47(ABq, J=16Hz, Δv=44Hz, 2H), 4.54(m, 1H), 6.77–6.88(m, 3H), 7.05–7.25 (m, 4H), 7.31–7.42(m, 2H), 7.66 (d, J=7Hz, 1H), 8.08(br s, 1H) | $C_{33}H_{45}N_5O_3$ | 70.81<br>71.10 | 8.10<br>8.28 | 12.51<br>12.53 |
| 75 | 1-(4-cyclohexyl-piperazinyl) (R) | foam | 560 (M + 1⁺) | CDCl₃ 1.09–1.28(m, 5H), 1.64(d, J=10Hz, 1H), 1.80–1.89(m, 4H), 2.10(s, 3H), 2.24–2.52(m, 9H), 2.90(s, 2H), 2.95(d, J=7Hz, 1H), 3.02(d, J=7Hz, 1H), 3.12(dd, J=5, 14Hz, 1H), 3.77(s, 3H), 4.01(dd, J=10, 14Hz, 1H), 4.49(ABq, J=17Hz, Δv=43Hz, 2H), 4.56(m, 1H), 6.79–6.87(m, 3H), 7.05–7.24 (m, 4H), 7.34–7.41(m, 2H), 7.67 (d, J=8Hz, 1H), 8.22(s, 1H) | $C_{33}H_{45}N_5O_3$ | 70.81<br>70.71 | 8.10<br>8.21 | 12.51<br>12.42 |
| 76 | 1-(4-cyclohexyl-piperazinyl) (S) | foam | 559 (M⁺) | ¹H CDCl₃ 1.05–1.31(m, 5H), 1.64 (m, 1H), 1.75–1.90(m, 4H), 2.10(s, 3H), 2.24–2.52(m, 9H), 2.87(s, 2H), 2.95(d, J=7Hz, 1H), 3.01(d, J=7Hz, 1H), 3.12(dd, J=5, 14Hz, 1H), 3.77(s, 3H), 3.99(dd, J=10, 14Hz, 1H), 4.46(ABq, J=17Hz, | $C_{33}H_{45}N_5O_3$ | 70.81<br>70.99 | 8.10<br>8.27 | 12.51<br>12.76 |

-continued

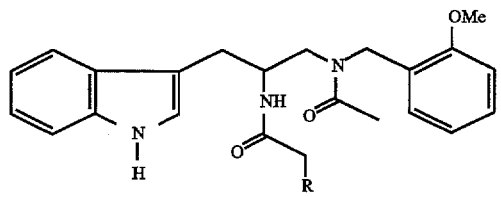

| Example No. | R | Mp, °C. | MS | $^1$H NMR | Formula | Analysis, % Theory/Found C | H | N |
|---|---|---|---|---|---|---|---|---|
| | | | | Δν=43Hz, 2H), 4.56(m, 1H), 6.75–6.90(m, 3H), 7.05–7.24(m, 4H), 7.34–7.41(m, 2H), 7.67(d, J=8Hz, 1H), 8.14(s, 1H) | | | | |
| 77 | 1-(4-PhCH$_2$-piperazinyl) | foam | 568 (M + 1$^+$) | CDCl$_3$ 2.08(s, 3H), 2.16–2.62m, 8H), 2.82–2.97(m, 3H), 2.99–3.18 (m, 2H), 3.41–3.62(m, 2H), 3.76(s, 3H), 4.02(dd, J=10, 13Hz, 1H), 4.49(ABq, J=18Hz, Δν=48Hz, 2H), 4.53(m, 1H), 6.76–6.88(m, 3H), 7.06(d, J=3Hz, 1H), 7.06–7.45(m, 10H), 7.68(d, J=8Hz, 1H), 8.06(br s, 1H) | C$_{34}$H$_{41}$N$_5$O$_3$ | 71.93 72.15 | 7.28 7.37 | 12.34 12.56 |
| 78 | 1-(4-(2-pyrimidinyl)-piperazinyl) | foam | 555 (M$^+$) | CDCl$_3$ 2.11(s, 3H), 2.28–2.55(m, 4H), 2.88–3.12(m, 5H), 3.56–3.86 (m, 4H), 3.77(s, 3H), 4.02(m, 1H), 4.47(ABq, J=17Hz, Δν=41Hz, 2H), 4.52(m, 1H), 6.50(br s, 1H), 6.76–6.86(m, 3H), 7.04–7.28(m, 4H), 7.36(d, J=7Hz, 1H), 7.61 (br s, 1H), 7.67(d, J=7Hz, 1H), 8.10(br s, 1H), 8.30(d, J=5Hz, 2H) | C$_{31}$H$_{37}$N$_7$O$_3$ | 67.01 66.90 | 6.71 6.85 | 17.64 17.43 |
| 79 | 1-(4-MeCO-piperazinyl) | foam | 519 (M$^+$), 520 (M + 1$^+$) | CDCl$_3$ 2.04(s, 3H), 2.09(s, 3H), 2.16–2.48(m, 4H), 2.86–3.11(m, 4H), 3.21–3.65(m, 5H), 3.78(s, 3H), 4.04(m, 1H), 4.46(ABq, J= 17Hz, Δν=26Hz, 2H), 4.50(m, 1H), 6.76–6.86(m, 3H), 7.02–7.28 (m, 4H), 7.36(d, J=7Hz, 1H), 7.50 (br s, 1H), 7.66(d, J=7Hz, 1H), 8.11(br s, 1H) | C$_{29}$H$_{37}$N$_5$O$_4$ | 67.03 66.81 | 7.18 7.20 | 13.48 13.30 |
| 80 | 1-(4-EtO(CO)-piperazinyl) | foam | 549 (M$^+$) | CDCl$_3$ 1.23(t, J=7Hz, 3H), 2.08 (s, 3H), 2.12–2.40(m, 4H), 2.85–2.97(m, 3H), 2.98–3.12(m, 2H), 3.22–3.49(m, 4H), 3.75(s, 3H), 4.03(m, 1H), 4.11(q, J=7Hz, 2H), 4.44(ABq, J=17Hz, Δν=45Hz, 2H), 4.48(m, 1H), 6.76–6.86(m, 3H), 7.04–7.25(m, 4H), 7.34(d, J= 8Hz, 1H), 7.46(br s, 1H), 7.66(d, J=8Hz, 1H), 8.04(br s, 1H) | C$_{30}$H$_{39}$N$_5$O$_5$ | 65.55 65.29 | 7.15 7.19 | 12.74 12.59 |
| 81 | (2-pyridyl)CH$_2$NH | foam | 499 (M$^+$) | CDCl$_3$ 2.10(s, 3H), 2.91(m, 1H), 3.00–3.16(m, 2H), 3.30(s, 2H), 3.65–3.88(m, 2H), 3.77(s, 3H), 4.01(dd, J=10, 16Hz, 1H), 4.46 (ABq, J=17Hz, Δν=53Hz, 2H), 4.54(m, 1H), 6.74–6.86(m, 2H), 7.02–7.28(m, 7H), 7.34(d, J=8Hz, 1H), 7.56–7.72(m, 3H), 8.06(br s, 1H), 8.55(d, J=6Hz, 1H) | C$_{29}$H$_{33}$N$_5$O$_3$ | 69.72 69.75 | 6.66 6.84 | 14.02 13.88 |
| 82 | (3-pyridyl)CH$_2$NH | foam | 499 (M$^+$) | CDCl$_3$ 2.08(s, 3H), 2.90(dd, J=8, 15Hz, 1H), 2.97–3.10(m, 2H), 3.24(s, 2H), 3.69(ABq, J=14Hz, Δν=25Hz, 2H), 3.74(s, 3H), 4.04 (dd, J=13, 16Hz, 1H), 4.45(ABq, J=18Hz, Δν=53Hz, 2H), 4.50(m, 1H), 6.74–6.87(m, 3H), 7.04(d, J= 4Hz, 1H), 7.08–7.30(m, 4H), 7.35 (d, J=8Hz, 1H), 7.49(d, J=8Hz, 1H), 7.60–7.70(m, 2H), 8.12(br s, 1H), 8.48–8.52(m, 2H) | C$_{29}$H$_{33}$N$_5$O$_3$ | 69.72 69.51 | 6.66 6.79 | 14.02 13.90 |
| 83 | (4-pyridyl)CH$_2$NH | foam | 499 (M$^+$) | CDCl$_3$ 2.09(s, 3H), 2.84–3.10(m, 3H), 3.20(s, 2H), 3.65(ABq, J= 14Hz, Δν=25Hz, 2H), 3.72(s, 3H), 4.08(dd, J=12, 15Hz, 1H), | C$_{29}$H$_{33}$N$_5$O$_3$ | 69.72 69.99 | 6.66 6.77 | 14.02 13.79 |

-continued

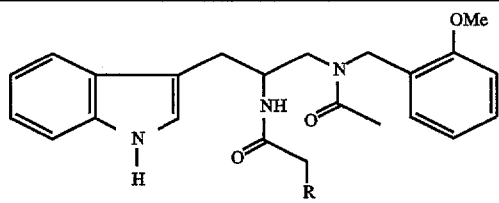

| Example No. | R | Mp, °C. | MS | ¹H NMR | Formula | Analysis, % Theory/Found | | |
|---|---|---|---|---|---|---|---|---|
| | | | | | | C | H | N |
| 84 | PhNHCOCH₂NH | foam | 541 (M+) | 4.40(ABq, J=16Hz, Δν=51Hz, 2H), 4.48(m, 1H), 6.73–6.84(m, 3H), 7.00(d, J=3Hz, 1H), 7.08–7.25(m, 5H), 7.32(d, J=8Hz, 1H), 7.45(d, J=8Hz, 1H), 7.67(d, J=8Hz, 1H), 8.01(br s, 1H), 8.51(d, J=7Hz, 2H) ¹H DMSO (3:2 mixture of amide rotamers) 1.95(s, 3/5•3H), 2.20(s, 2/5•3H), 2.75–2.93(m, 2H), 3.07–3.17(m, 2H), 3.17–3.30(m, 3H), 3.39(m, 1H), 3.53(m, 1H), 3.67(s, 2/5•3H), 3.72(s, 3/5•3H), 4.25–4.61(m, 3H), 6.77–6.87(m, 2H), 6.87–7.09(m, 4H), 7.12(m, 1H), 7.14–7.36(m, 4H), 7.55(d, J=8Hz, 1H), 7.63(t, J=8Hz, 2H), 7.91(d, J=9Hz, 3/5•1H), 8.05(d, J=9Hz, 2/5•1H), 9.92(br s, 0.4H), 9.94(br s, 0.6H), 10.78(br s, 0.6H), 10.80(br s, 0.4H). | $C_{31}H_{35}N_5O_4$ | 68.74 68.51 | 6.51 6.56 | 12.93 12.78 |

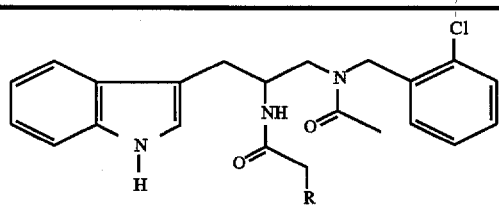

| Example No. | R | Mp, °C. | MS | ¹H NMR | Formula | Analysis % Theory/Found | | |
|---|---|---|---|---|---|---|---|---|
| | | | | | | C | H | N |
| 86 | 1-(4-i-Pr-piperazinyl) (R) | foam | 523 (M⁺) | ¹H CDCl₃ 0.9–1.1(m, 6H), 2.05(s, 3H), 2.1–2.5(m, 11H), 2.8–3.1(m, 3H), 3.2(m, 1H), 4.0(m, 1H), 4.5–4.7(m, 2H), 6.9–7.4(m, 9H), 7.63(d, J=6Hz, 1H), 8.23(br s, 1H). | $C_{29}H_{38}ClN_5O_2$ | 66.46 66.72 | 7.31 7.33 | 13.36 13.30 |
| 87 | 1-(4-cyclohexyl-piperazinyl) (R) | foam | 563 (M⁺) | ¹H CDCl₃ 1.0–1.4(m, 6H), 1.6(m, 1H), 1.7–1.9(m, 4H), 2.08(s, 3H), 2.1–2.6(m, 9H), 2.8–3.1(m, 4H), 4.0(m, 1H), 4.5–4.7(m, 3H), 7.0–7.4(m, 9H), 7.63(d, J=6Hz, 1H), 8.18(br s, 1H). | $C_{32}H_{42}ClN_5O_2$ | 68.13 67.93 | 7.50 7.53 | 12.41 12.43 |

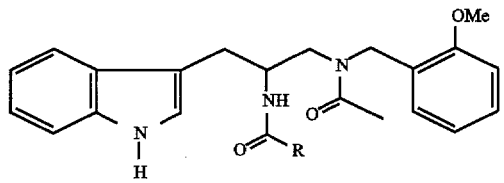

| Example No. | R | Mp, °C. | MS | ¹H NMR | Formula | Analysis % Theory/Found C | H | N |
|---|---|---|---|---|---|---|---|---|
| 88 | Ph | foam | 455 (M⁺) | CDCl₃ 2.10(s, 3H), 2.81–2.94 (m, 2H), 3.32(dd, J=5, 15 Hz, 1H), 3.66(s, 3H), 4.21 (dd, J=13, 15Hz, 1H), 4.36 (ABq, J=15Hz, Δν=43Hz, 2H), 4.46(m, 1H), 6.61–6.80 (m, 3H), 7.00(d, J=5Hz, 1H), 7.10–7.50(m, 7H), 7.70 (d, J=8Hz, 1H), 7.80(d, J=6) Hz, 1H), 7.87(d, J=6Hz, 2H), 7.96(br s, 1H) | C₂₈H₂₉N₃O₃ | 73.82 73.86 | 6.42 6.44 | 9.22 9.36 |
| 89 | Ph(CH₂)₂ (RS) | foam | 483 (M⁺) | CDCl₃ 2.05(s, 3H), 2.45(t, J=9Hz, 2H), 2.72–3.12(m, 5H), 3.71(s, 3H), 4.01(dd, J=12, 14Hz, 1H), 4.33(ABq, J=16Hz, Δν=60Hz, 2H), 4.38(m, 1H), 6.58(d, J=9 Hz, 1H), 6.66–6.81(m, 3H), 6.88(d, J=3Hz, 1H), 7.09–7.38(m, 9H), 7.68(d, J=7 Hz, 1H), 7.98(br s, 1H) | C₃₀H₃₃N₃O | 74.51 74.81 | 6.88 7.06 | 8.69 8.39 |
| 90 | Ph(CH₂)₂ (R) | foam | 283 (M⁺) | ¹H CDCl₃ 2.05(s, 3H), 2.46 (t, J=8Hz, 2H), 2.70–2.90(m, 2H), 2.96(t, J=8Hz, 2H), 3.10(m, 1H), 3.71(s, 3H), 4.03(m, 1H), 4.24(d, J=17 Hz, 1H), 4.33–4.50(m, 2H), 6.60–6.86(m, 4H), 6.89(s, 1H), 7.05–7.40(m, 9H), 7.69 (d, J=8Hz, 1H), 8.03(s, 1H) | C₃₀H₃₃N₃O₃ | 74.51 74.30 | 6.88 6.66 | 8.69 8.46 |
| 91 | Ph(CH₂)₂ (S) | foam | 483 (M⁺) | ¹H CDCl₃ 2.04(s, 3H), 2.45 (t, J=8Hz, 2H), 2.73–2.89(m, 2H), 2.96(t, J=8Hz, 2H), 3.06(dd, J=4, 10Hz, 1H), 3.71(s, 3H), 4.03(m, 1H), 4.20–4.50(m, 3H), 6.58–6.88 (m, 4H), 6.89(s, 1H), 7.07–7.40(m, 9H), 7.69(d, J=8Hz, 1H), 8.03(s, 1H) | C₃₀H₃₃N₃O₃ | 74.51 74.60 | 6.88 6.96 | 8.69 8.70 |
| 92 | PhCH₂O (R) | foam | 485 (M⁺) | ¹H CDCl₃ 2.09(s, 3H), 2.83 (dd, J=7, 15Hz, 1H), 2.95 (dd, J=3, 14Hz, 1H), 3.10 (dd, J=3, 14Hz, 1H), 3.70(s, 3H, 3.96(m, 1H), 4.22(m, 1H), 4.26(m, 1H), 4.72(s, 1H), 5.12(s, 2H), 5.68(m, 1H), 6.88–6.83(m, 2H), 6.97 (m, 1H), 7.07–7.46(m, 10H), 7.66(d, J=8Hz, 1H), 8.02(s, 1H) | C₂₉H₃₁N₃O₄ | 71.73 71.61 | 6.43 6.21 | 8.65 8.67 |
| 93 | PhCH₂O (S) | oil | 485 (M+) | ¹H CDCl₃ 1.70–2.10(m, 3H), 2.75–3.00(m, 2H, 3.10(m, 1H), 3.70(s, 3H), 3.95(m, 1H), 4.10(m, 1H), 4.45(m, 1H), 4.61(s, 1H), 5.13(s, 2H), 5.73(m, 1H), 6.66–6.85 (m, 2H), 6.95(m, 1H), 7.03–7.50(m, 10H), 7.66(d, J=8 Hz, 1H), 8.02(br s, 1H). | C₂₉H₃₁N₃O₄ | 71.73 71.90 | 6.43 6.60 | 8.65 8.51 |
| 94 | Ph(CH₂)₃ | foam | 497 (M⁺) | CDCl₃ 1.88–2.00(m, 2H), 2.09(s, 3H), 2.13–2.23(m, 2H), 2.61(t, J=8Hz, 2H), 2.78–2.92(m, 2H), 3.12(dd, J=4, 9Hz, 1H), 3.69(s, 3H), 4.10(dd, J=7, 9Hz, 1H), 4.40 | C₃₁H₃₅N₃O₃ | 74.82 74.58 | 7.09 7.13 | 8.44 8.32 |

-continued

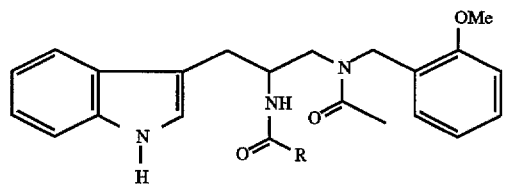

| Example No. | R | Mp, °C. | MS | $^1$H NMR | Formula | Analysis % Theory/Found C | H | N |
|---|---|---|---|---|---|---|---|---|
| | | | | (ABq, J=17Hz, Δν=56Hz, 2H), 4.40(m, 1H), 6.61(br s, 1H), 6.67–6.81(m, 3H), 6.99 (s, 1H), 7.04–7.36(m, 9H), 7.70(d, J=8Hz, 1H), 7.98(br s, 1H) | | | | |
| 95 | PhCO(CH$_2$)$_2$ (RS) | foam | 511 (M$^+$) | CDCl$_3$ 2.17(s, 3H), 2.57(t, J=7Hz, 2H), 2.79–2.89(m, 2H), 3.11(dd, J=6, 14Hz, 1H), 3.21–3.45(m, 2H), 3.68 (s, 3H), 4.09(dd, J=12, 14 Hz, 1H), 4.38(ABq, J=16Hz, Δν=75Hz, 2H), 4.40(m, 1H), 6.71–6.79(m, 4H), 7.01(d, J=3Hz, 1H), 7.09–7.22(m, 3H), 7.34(d, J=7Hz, 1H), 7.46(t, J=8Hz, 2H), 7.56(m, 1H), 7.70(d, J=8Hz, 1H), 8.00(d, J=8Hz, 3H) | C$_{31}$H$_{33}$N$_3$O$_4$ | 72.78  72.71 | 6.50  6.38 | 8.21  7.95 |
| 96 | PhCO(CH$_2$)$_2$ (R) | oil | 511 (M$^+$) | $^1$H CDCl$_3$ 2.19(s, 3H), 2.58(t, J=4Hz, 1H), 2.80–2.93(m, 2H), 3.05(m, 1H), 3.20–3.46(m, 3H), 3.70(s, 3H), 4.05(m, 1H), 4.26(m, 1H), 4.33–4.60(m, 2H), 6.66–6.86(m, 4H), 7.00(s, 1H), 7.06–7.23(m, 3H), 7.30(d, J=8Hz, 1H), 7.43–7.53(m, 2H), 7.58(d, J=8Hz, 1H), 7.70(d, J=8Hz, 1H), 7.97(d, J=8Hz, 2H), 8.12(s, 1H). | C$_{31}$H$_{33}$N$_3$O$_4$ | 72.78  72.84 | 6.50  6.61 | 8.21  8.22 |
| 97 | PhCO(CH$_2$)$_2$ (S) | oil | 511 (M$^+$) | $^1$H DMSO (4:3 mixture of amide rotamers)1.70 (s, 4/7·1H), 1.77(s, 3/7·1H), 1.92(s, 4/7·3H), 200(s, 3/7·3H), 2.40(m, 1H), 2.60–2.80(m, 2H), 3.10–3.25(m, 3H), 3.50(m, 1H), 3.65(s, 3/7·3H), 3.72(s, 4/7·3H), 4.25–4.60(m, 3H), 6.75–7.35(m, 8H), 7.45–7.70(m, 4H), 7.74(d, J=8Hz, 1H), 7.80–8.00(m, 2H), 10.77(m, 1H). | C$_{31}$H$_{33}$N$_3$O$_4$ | 72.78  72.86 | 6.50  6.50 | 8.21  8.17 |
| 98 | PhCO(CH$_2$)$_3$ | foam | 525 (M$^+$) | CDCl$_3$ 2.00–2.11(m, 2H), 2.11(s, 3H), 2.25(t, J=7Hz, 2H), 2.76–2.91(m, 2H), 2.98–3.16(m, 3H), 3.71(s, 3H), 4.04(dd, J=11, 13Hz, 1H), 4.38(ABq, J=17Hz, Δν=54Hz, 2H), 4.39(m, 1H), 6.60–6.81(m, 4H), 6.98(s, 1H), 7.08–7.24 (m, 3H), 7.34(d, J=9Hz, 1H), 7.45(t, J=9 Hz, 2H), 7.55(m, 1H), 7.70(d, J=9Hz, 1H), 7.96(d, J=8Hz, 2H), 8.01(br s, 1H) | C$_{32}$H$_{35}$N$_3$O$_4$ | 73.12  72.86 | 6.71  6.66 | 7.99  7.73 |

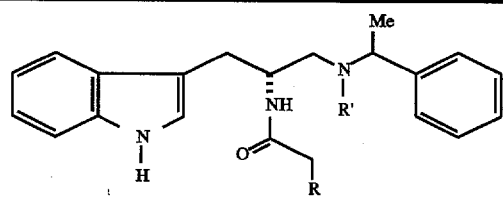

| Example No. | R | R' | Mp °C. | MS | $^1$H NMR | Formula | Analysis % Theory/Found C | H | N |
|---|---|---|---|---|---|---|---|---|---|
| 99 | H (RS) | MeCO | foam | 377 (M$^+$) | CDCl$_3$1.42(d, J=8Hz, 3H), 1.92(s, 3H), 2.23(s, 3H), 2.53(dd, J=8, 14Hz, 1H), 2.85–3.05(m, 2H), 3.28(m, 1H), 3.81(dd, J=10, 14Hz, 1H), 4.94(q, J=8Hz, 1H), | C$_{23}$H$_{27}$N$_3$O$_2$ | 73.18  73.35 | 7.21  7.46 | 11.13  10.90 |

-continued

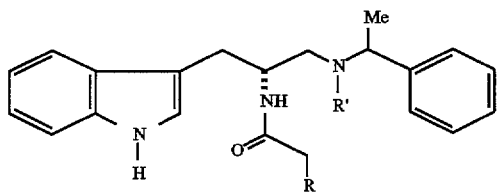

| Example No. | R | R' | Mp °C. | MS | ¹H NMR | Formula | Analysis % Theory/Found C | H | N |
|---|---|---|---|---|---|---|---|---|---|
| 100 | H (RR) | MeCO | foam | 377 (M⁺) | 6.82(m, 1H), 6.82–7.27(m, 7H), 7.27–7.45(m, 2H), 7.54 (d, J=8Hz, 1H), 8.01(br s, 1H) CDCl₃ 1.38(d, J=8Hz, 3H), 1.93(s, 3H), 2.17(s, 3H), 2.68(dd, J=8, 14Hz, 1H), 2.74(dd, J=4, 14Hz, 1H), 3.20(dd, J=4, 14Hz, 1H), 3.91(dd, J=10, 14Hz, 1H), 4.37(m, 1H), 4.92(m, 1H), 6.78–7.27(mHz, 9H), 7.37 (d, J=8Hz, 1H), 7.75(d, J=8 Hz, 1H), 7.98(br s, 1H) | C₂₃H₂₇N₃O₂ | 73.18 73.39 | 7.21 7.33 | 11.13 10.96 |
| 101 | 1-(4-(1-piperidinyl)-piperidinyl) (RS) | H | foam | 501 (M⁺) | CDCl₃ 1.32 (d, J=7Hz, 3H), 1.15–1.91(m, 11H), 1.91–2.23(m, 3H), 2.30–2.60(m, 6H), 2.65(dd, J=6, 14Hz, 1H), 2.72–2.94(m, 4H), 3.01 (dd, J=6, 14Hz, 1H), 3.72 (q, J=7Hz, 1H), 4.35(m, 1H), 6.95(d, J=2Hz, 1H), 7.03–7.42(m, 9H), 7.64(d, J=8Hz, 1H), 8.08(br s, 1H) | C₃₁H₄₃N₅O | 74.21 74.50 | 8.64 8.49 | 13.96 13.94 |
| 102 | 1-(4-(1-piperidinyl)-piperidinyl) (RR) | H | foam | 501 (M⁺) | DMSOd₆ 1.23(d, J=6 Hz, 3H), 1.12–1.70(m, 11H), 1.89–2.01(m, 2H), 2.01–2.17 (m, 2H), 2.23–2.43(m, 5H), 2.52(m, 1H), 2.72(m, 1H), 2.75(ABq, J=15Hz, Δv=30 Hz, 2H), 2.83(dd, J=8, 14 Hz, 1H), 2.95(dd, J=6, 14 Hz, 1H), 3.66(q, J=6 Hz, 1H), 4.06(m, 1H), 6.95(t, J=8Hz, 1H), 6.99–7.10(m, 2H), 7.10–7.41(m, 6H), 7.49 (d, J=9Hz, 1H), 7.56(d, J=8 Hz, 1H), 10.78(br s, 1H) | C₃₁H₄₃N₅O | 74.21 73.93 | 8.64 8.65 | 13.96 13.89 |
| 103 | 1-(4-(1-piperidinyl)-piperidinyl) (RS) | MeCO | foam | 543 (M⁺) | CDCl₃ 1.29–1.88(m, 12H), 1.88–2.08(m, 2H), 2.15(s, 3H), 2.21(m, 1H), 2.36–2.62 (m, 6H), 2.62–2.88(m, 4H), 2.96(dd, J=6, 14Hz, 1H), 3.28(dd, J=6, 14Hz, 1H), 3.65(dd, J=10, 14Hz, 1H), 3.82(m, 1H), 4.98(m, 1H), 6.85–7.45(m, 9H), 7.48–7.59 (m, 2H), 8.10(br s, 1H) | C₃₃H₄₅N₅O₂ | 72.89 73.13 | 8.34 8.27 | 12.88 12.91 |
| 104 | 1-(4-(1-piperidinyl)-piperidinyl) (RR) | MeCO | foam | 543 (M⁺) | DMSO-d₆ 2:1 mixture of amide rotamers 1.19–1.84 (m, 12H), 1.84–2.16(m, 3H), 2.06(s, 3H), 2.32–2.52(m, 5H), 2.57–3.00(m, 6H), 3.20 (m, 1H), 3.79(dd, J=11, 14Hz, 1H), 4.28(m, 1H), 5.04 (m, 2/3·1H), 5.49(m, 1/3·1H), 6.89–7.15(m, 5H), 7.15–7.28(m, 3H), 7.32(d, J=8Hz, 1H), 7.47(m, 1H), 8.41(m, 1H), 10.77(br s, 1H) | C₃₃H₄₅N₅O₂ | 72.89 72.65 | 8.34 8.14 | 12.88 12.71 |

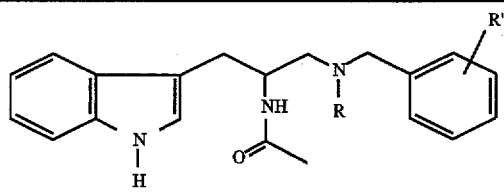

| Example No. | R | R' | Mp °C. | MS | ¹H NMR | Formula | Analysis % Theory/Found C | H | N |
|---|---|---|---|---|---|---|---|---|---|
| 105 | H | 2-OMe | foam | 351 (M⁺) | CDCl₃ 1.97(s, 3H), 2.38(m, 1H), 2.73(dd, J=6, 12Hz, 1H), 2.82 (dd, J=6, 12Hz, 1H), 2.97(dd, J=8, 14Hz, 1H), 3.10(dd, J=6, 14Hz, 1H), 3.75–3.94(m, 2H), 3.82(s, 3H), 4.42(m, 1H), 6.34 (brd, J=8Hz, 1H), 6.77–6.95(m, 2H), 7.01(d, J=2Hz, 1H), 7.07–7.33(m, 4H), 7.37(d, J=8Hz, 1H), 7.68(d, J=8Hz, 1H), 8.13 (br s, 1H) | C₂₁H₂₅N₃O₂ | 71.77 71.48 | 7.17 6.90 | 11.96 12.09 |
| 106 | MeCO | 2-OMe | 147–148 | 393 (M⁺) | CDCl₃/DMSOd₆ 1.95(s, 3H), 2.13(s, 3H), 2.81(dd, J=8, 16Hz, 1H), 2.89(dd, J=4, 14Hz, 1H), 3.72(s, 3H), 3.99(t, J=10Hz, 1H), 4.35(m, 1H), 4.37 (ABq, J=16Hz, Δv=58Hz, 2H), 7.65–7.82(m, 4H), 6.99(s, 1H), 7.01–7.22(m, 3H), 7.37(d, J=7Hz, 1H), 7.66(d, J=8Hz, 1H), 9.19(br s, 1H) | C₂₃H₂₇N₃O₃ | 70.21 69.93 | 6.92 7.06 | 10.68 10.58 |
| 107 | 1-(4-Ph-piperazinyl) CH₂CO | 2-OMe | foam | 553 (M⁺) | CDCl₃ 1.93(s, 3H), 2.72–2.98(m, 6H), 3.08(dd, J=6, 15Hz, 1H), 3.18–3.52(m, 6H), 3.73(s, 3H), 4.02(t, J=13Hz, 1H), 4.33(d, J=16Hz, 1H), 4.42(m, 1H), 4.64 (d, J=16Hz, 1H), 6.45(d, J=8Hz, 1H), 6.66–6.95(m, 6H), 7.00 (d, J=3Hz, 1H), 7.04–7.30(m, 5H), 7.36(d, J=9Hz, 1H), 7.67 (d, J=8Hz, 1H), 8.07(br s, 1H) | C₃₃H₃₉N₅O₃ | 71.58 71.33 | 7.10 7.09 | 12.65 12.61 |
| 108 | 1-(4-(1-piperidinyl)-piperidinyl) CH₂CO | H | foam | 530 (M+1) | CDCl₃ 2:1 mixture of amide rotamers 1.24–1.89(m, 10H), 1.90(s, 2/3·3H), 1.96(s, 1/3·3H), 1.92–2.10(m, 2H), 2.23 (m, 1H), 2.34(m, 1H), 2.42–2.53 (m, 2H), 2.62–2.94(m, 5H), 3.01–3.23(m, 3H), 3.57(dd, J=12, 14Hz, 1/3·1H), 4.06(dd, J=12, 15Hz, 2/3·1H), 4.43(br s, 2/3·1H), 4.57(ABq, J=16Hz, Δv=169Hz, 2/3·2H), 4.58(ABq, J=16Hz, Δv=273Hz, 1/3·2H), 4.63(br s, 1/3·1H), 6.38(d, J=8Hz, 2/3·1H), 6.73(d, J=8Hz, 1/3·1H), 6.84–6.98(m, 2H), 7.05–7.30(m, 6H), 7.34(d, J=7Hz, 1H), 7.53(d, J=8Hz, 1/3·1H), 7.66(d, J=8Hz, 2/3·1H), 7.99 (br s, 2/3·1H), 8.13(br s, 1/3·1H) | C₃₂H₄₃N₅O₂ | 72.56 72.29 | 8.18 8.04 | 13.22 13.21 |
| 109 | 1-(4-(1-piperidinyl)-piperidinyl) CH₂CO | 2-Cl | foam | 563 (M+1) | CDCl₃ 3:1 mixture of amide rotamers 1.38–1.86(m, 11H), 1.93(s, 3/4·3H), 1.98(s, 1/4·3H), 1.86–2.12(m, 2H), 2.18–2.73(m, 5H), 2.77–2.98(m, 3H), 2.99–3.19(m, 3H), 3.67(dd, J=12, 14Hz, 1/4·1H), 4.10(dd, J=12, 14Hz, 3/4·1H), 4.41(m, 3/4·1H), 4.65(m, 1/4·1H), 4.66(ABq, J=18Hz, Δv=107Hz, 3/4·2H), 4.72(ABq, J=15Hz, Δv=157Hz, 1/4·2H), 6.40(br d, J=7Hz, 1H), 6.90(d, J=7Hz, 1H), 7.02(br s, 1H), 7.06–7.40 | C₃₂H₄₂ClN₅O₂ | 68.13 66.92 | 7.50 7.48 | 12.41 12.32 |

-continued

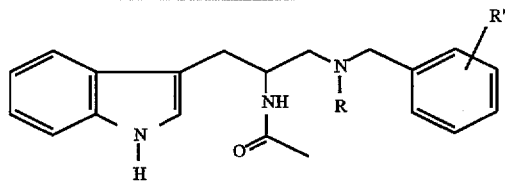

| Example No. | R | R' | Mp °C. | MS | ¹H NMR | Formula | Analysis % Theory/Found C | H | N |
|---|---|---|---|---|---|---|---|---|---|
| | | | | | (m, 6H), 7.55(d, J=8Hz, 1/4·1H), 7.64(d, J=8Hz, 3/4·1H), 8.04(br s, 1H) | | | | |

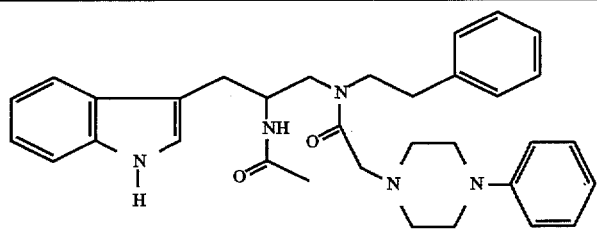

| Example No. | Mp °C. | MS | ¹H NMR | Formula | Analysis, Theory/Found C | H | N |
|---|---|---|---|---|---|---|---|
| 110 | foam | 537 (M+) | ¹H DMSO(3:2 mixture of amide rotomers)1.79(s, 3/5.3H), 1.81(s, 2/5.3H), 2.25–2.46(m, 4H), 2.59–3.21 (m, 10H), 3.23–3.67(m, 4H), 4.46(m, 1H), 6.76(t, J=8Hz, 1H), 6.91(d, J=8Hz, 2H), 6.94–7.40(m, 11H), 7.60(m, 1H), 7.81–8.05(m, 1H), 10.81(br s, 2/5.1H), 10.84(br s, 3/5.1H). | $C_{33}H_{39}N_5O_2$ | 73.71 73.64 | 7.31 7.33 | 13.02 13.08 |

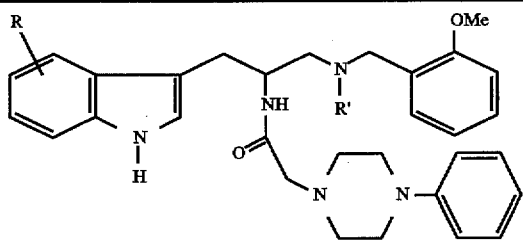

| Example No. | R | R' | Mp °C. | MS | ¹H NMR | Formula | Analysis, Theory/Found C | H | N |
|---|---|---|---|---|---|---|---|---|---|
| 111 | 5-Br | H | oil | 590, 592 (M+1) for Br isotopes) | CDCl₃ 2.33–2.45(m, 2H), 2.45–2.53 (m, 2H), 2.80–3.10(m, 11H), 3.75(s, 1H), 3.88(s, 3H), 3.94(d, J=4Hz, 2H), 6.80–6.96(m, 6H), 7.10(s, 1H), 7.20–7.36(m, 5H), 7.40(m, 1H), 7.75 (s, 1H), 8.20(s, 1H) | $C_{31}H_{36}N_5O_2Br$ | 63.05 63.21 | 6.14 6.21 | 11.86 11.59 |
| 112 | 5-OCH₂Ph | H | oil | 617 (M⁺) | DMSO-d6 2.30–2.65(m, 8H), 2.80–3.15(m, 8H), 3.31(s, 1H), 3.64(s, 2H), 3.72(s, 3H), 4.15(m, 1H), 6.65–6.95(m, 6H), 7.05(s, 1H), 7.10–7.25 (m, 5H), 7.25–7.40(m, 4H), 7.43(d, J=9Hz, 2H), 7.50(d, J=9Hz, 1H), 10.70(s, 1H) | $C_{38}H_{43}N_5O_3$ | 73.88 74.09 | 7.02 7.03 | 11.34 11.31 |

-continued

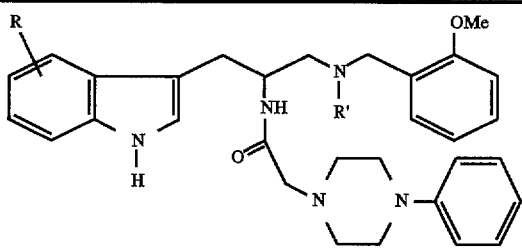

| Example No. | R | R' | Mp °C. | MS | ¹H NMR | Formula | Analysis, Theory/Found C | H | N |
|---|---|---|---|---|---|---|---|---|---|
| 113 | 1-Me | MeCO | oil | 567 (M⁺) | CDCl₃ 2.11(s, 3H), 2.36–2.60(m, 3H), 2.85–3.20(m, 10H), 3.71(s, 3H), 3.77(s, 3H), 3.97(br s, 1H), 4.36–4.60(m, 3H), 6.78–7.00(m, 7H), 7.10 (s, 1H), 7.20–7.35(m, 6H), 7.66(d, J=8Hz, 1H) | C₃₄H₄₁N₅O₃ | 71.93 71.69 | 7.28 7.36 | 12.34 12.28 |
| 114 | 6-Me | MeCO | oil | FD-MS 567(M⁺) | ¹H CDCl₃ 2.10(s, 3H), 2.10(m, 1H), 2.40–2.70(m, 7H), 2.90–3.10(m, 7H), 3.16(dd, J=4, 13Hz, 1H), 3.78(s, 3H), 3.97(m, 1H), 4.40–4.70(m, 3H), 6.80–7.10(m, 8H), 7.16(s, 1H), 7.20–7.40(m, 3H), 7.45(m, 1H), 7.54(d, J=8Hz, 1H), 7.94(m, 1H). | C₃₄H₄₁N₅O₃ | 71.93 71.72 | 7.28 6.99 | 12.34 12.10 |
| 115 | 7-Me | MeCO | foam | 567(M⁺) | ¹H CDCl₃ 2.08(s, 3H), 2.35–2.53(m, 7H), 2.88–3.15(m, 10H), 3.76(s, 3H), 4.48(ABq, J=17.1Hz, Δv=41.2Hz, 2H), 4.55(m, 1H), 6.78–6.90(m, 6H), 6.96–7.08(m, 3H), 7.22(m, 3H), 7.40(m, 1H), 7.50(d, J=8.0Hz, 1H), 7.95(s, 1H). | C₃₄H₄₁N₅O₃ | 71.93 71.82 | 7.28 7.31 | 12.34 12.32 |
| 116 | 5-Br | MeCO | 124–126 | 631, 633 (M⁺'s for Br isotopes) | CDCl₃ 2.12(s, 3H), 2.40–2.66(m, 4H), 2.83–3.20(m, 9H), 3.80(s, 3H), 3.96(m, 1H), 4.43–4.60(m, 3H), 6.83–6.96(m, 6H), 7.10(s, 1H), 7.20–7.33(m, 5H), 7.46(br s, 1H), 7.75(s, 1H), 8.44(s, 1H) | C₃₃H₃₈N₅O₃Br | 62.66 62.92 | 6.05 6.04 | 11.07 11.25 |
| 117 | 5-OMe | MeCO | oil | 583(M⁺) Exact Mass FAB (M+1) theory: 584.3237 found: 584.3214 | DMSO-d6 1:1 mixture of amide rotamers 1.86(s, 1/2.3H), 1.94(s, 1/2.3H), 2.23–2.43(m, 4H), 2.73–2.93(m, 4H), 2.93–3.10(m, 4H), 3.16(m, 1H), 3.56(m, 1H), 3.66(s, 1/2.3H), 3.69(s, 1/2.3H), 3.71(s, 1/2.3H), 3.72(s, 1/2.3H), 4.23–4.60(m, 3H), 6.66–7.00(m, 7H), 7.08(s, 2H), 7.15–7.26(m, 4H), 7.59(d, J=8Hz, 1/2.1H), 7.77(d, J=8Hz, 1/2.1H), 10.65(s, 1H) | C₃₄H₄₁N₅O₄ | | | |
| 118 | 5-OCH₂Ph | MeCO | oil | 660 (M+1⁺) | DMSO-d6 3:2 mixture of amide rotamers 1.94(s, 3/5.3H), 2.04(s, 2/5.3H), 2.23–2.56(m, 5H), 2.66–2.93(m, 4H), 2.93–3.13(m, 3H), 3.30–3.50(m, 3H), 3.58(m, 1H), 3.68(s, 2/5.3H), 3.70(s, 3/5.3H), 4.24–4.60(m, 3H), 6.70–7.00(m, 7H), 7.06(s, 1H), 7.13–7.50(m, 10H), 7.55(d, J=8Hz, 3/5.1H), 7.66(d, J=8Hz, 2/5.1H), 10.70(s, 1H) | C₄₀H₄₅N₅O₄ | 72.81 72.58 | 6.87 6.85 | 10.61 10.37 |

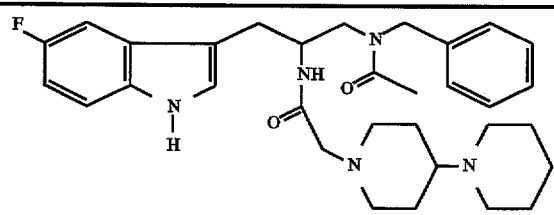

| Example No. | Mp °C. | MS | ¹H NMR | Formula | Analysis, % Theory/Found C | H | N |
|---|---|---|---|---|---|---|---|
| 119 | foam | 548 (M+) | ¹H CDCl₃ 1.30–1.72(m, 10H), 1.96–2.24(m, 6H), 2.41–2.56(m, 5H), 2.70–2.77(m, 1H), 2.85(s, 2H), 2.87–3.00(m, 2H), 3.16(dd, J=4.7, 13.8Hz, 1H), 4.00(dd, J=10.1, 13.8Hz, 1H), 4.48–4.57 (m, 1H), 4.55(ABq, J=17.0Hz, | C₃₂H₄₂FN₅O₂ | 70.17 69.94 | 7.73 7.80 | 12.79 12.74 |

-continued

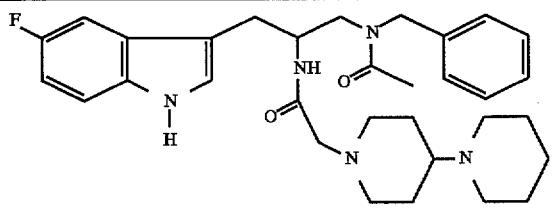

| Example No. | Mp °C. | MS | ¹H NMR | Formula | Analysis, % Theory/Found | | |
|---|---|---|---|---|---|---|---|
| | | | | | C | H | N |
| | | | Δν=4.77Hz, 2H), 6.93(m, 1H), 7.08–7.16(m, 3H), 7.21–7.41(m, 6H), 8.27(s, 1H). | | | | |

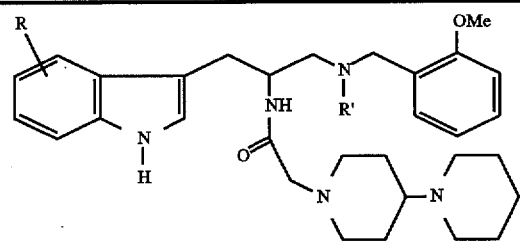

| Example No. | R | R' | Mp °C. | MS | ¹H NMR | Formula | Analysis, Theory/Found | | |
|---|---|---|---|---|---|---|---|---|---|
| | | | | | | | C | H | N |
| 120 | 5-Br | H | oil | 596, 598 (M+1) for Br isotopes) | DMSO-d6 1.20–1.56(m, 12H), 1.75–2.00(m, 2H), 2.20–2.40(m, 7H), 2.60–2.80(m, 3H), 2.85(d, J=6Hz, 2H), 3.63(br s, 2H), 3.74 (s, 3H), 4.10(m, 1H), 6.83–6.93(m, 2H), 7.10–7.23(m, 3H), 7.23–7.30 (m, 2H), 7.45(d, J=8Hz, 1H), 7.55 (s, 1H), 11.10(s, 1H) | C₃₁H₄₂BrN₅O₂ | 62.41 62.63 | 7.10 6.96 | 11.74 12.01 |
| 121 | 5-OMe | H | oil | 547 (M⁺) | DMSO-d6 1.20–1.70(m, 11H), 1.66–2.20(m, 4H), 2.20–2.43(m, 4H), 2.43–2.65(m, 3H), 2.65–2.90 (m, 4H), 3.61(s, 2H), 3.77(s, 3H), 3.80(s, 3H), 4.13(m, 1H), 6.70(m, 1H), 6.80–7.00(m, 2H), 7.02(s, 1H), 7.08(s, 1H), 7.10–7.40(m, 3H), 7.45(d, J=8Hz, 1H), 10.65(s, 1H) | C₃₂H₄₅N₅O₃ | 70.17 70.29 | 8.28 8.09 | 12.79 12.56 |
| 122 | 5-OCH₂Ph | H | oil | 624 (M+1⁺) | DMSO-d6 1.20–1.33(m, 11H), 1.80–2.10(m, 4H), 2.25–2.40(m, 5H), 2.50–2.60(m, 3H), 2.65–2.90 (m, 5H), 3.63(s, 2H), 3.74(5, 3H), 4.08(m, 1H), 6.77(d, J=2Hz, 1H), 6.80–7.00(m, 2H), 7.03(s, 1H), 7.13–7.25(m, 3H), 7.25–7.50(m, 7H), 10.70(s, 1H) | C₃₈H₄₉N₅O₃ | 73.16 73.45 | 7.92 7.92 | 11.23 11.14 |
| 123 | 6-F | H | foam | 536 (M+1) | ¹H CDCl₃ 1.22–1.78(m, 12H), 1.95–2.15(m, 3H), 2.43–2.57(m, 4H), 2.69–3.08(m, 7H), 3.74–3.88 (m, 5H), 4.39(m, 1H), 6.85–7.13 (m, 5H), 7.21–7.27(m, 2H), 7.33(d, J=4.9Hz, 1H), 7.58(m, 1H), 8.25 (s, 1H). | C₃₁H₄₂FN₅O₂ | 71.17 70.89 | 8.26 8.26 | 12.21 11.91 |
| 124 | 1-Me | MeCO | oil | 573 (M⁺) | DMSO-d₆ 3:2 mixture of amide rotamers 1.30–1.60(m, 11H), 1.80–1.95(m, 2H), 1.93(s, ⅗.3H), 2.03 (s, ⅖.3H), 2.05(m, 1H), 2.40(br s, 3H), 2.50–2.86(m, 6H), 3.14(m, 1H), 3.67(m, 1H), 3.68(s, ⅗.6H), 3.71(s, ⅖.6H), 4.23–4.56(m, 3H), 6.79(m, 1H), 6.86–7.28(m, 5H), 7.34(d, J=8Hz, 1H), 7.53(m, | C₃₄H₄₇N₅O₃ | 71.17 71.30 | 8.25 7.97 | 12.21 12.09 |

-continued

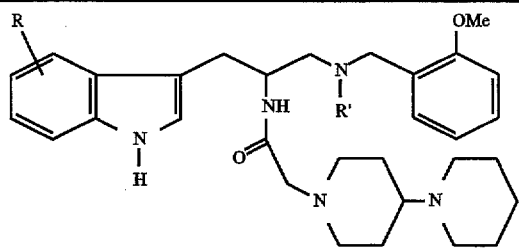

| Example No. | R | R' | Mp °C. | MS | ¹H NMR | Formula | Analysis, Theory/Found C | H | N |
|---|---|---|---|---|---|---|---|---|---|
| | | | | | ⅗.2H), 7.63(m, ⅔.2H), 8.30(s, 1H) | | | | |
| 125 | 4-Me | MeCO | foam | 573 (M⁺) | ¹H CDCl₃ 1.46(m, 3H), 1.51–1.81 (m, 7H), 2.01–2.26(m, 6H), 2.43–2.68(m, 5H), 2.70–2.84(m, 4H), 2.87(s, 2H), 3.07–3.24(m, 3H), 3.78(s, 3H), 3.98(dd, J=9.8, 13.6 Hz, 1H), 4.45–4.61(m, 3H), 6.84 (m, 3H), 6.88–6.94(m, 1H), 7.03–7.10(m, 2H), 7.16–7.39(m, 3H), 8.07(s, 1H). | C₃₄H₄₇N₅O₃ | 71.17 70.84 | 8.26 8.26 | 12.21 11.91 |
| 126 | 5-Me | MeCO | foam | 573 (M⁺) | ¹H CDCl₃ 1.25–1.72(m, 11H), 1.99–2.17(m, 6H), 2.46(m, 7H), 2.75(dd, J=1.4, 9.7Hz, 1H), 2.86 (s, 2H), 2.91(d, J=7.0Hz, 1H), 2.99(d, J=6.3Hz, 1H), 3.14(dd, J=4.7, 13.8Hz, 1H), 3.77(s, 3H), 3.96(dd, J=10.1, 13.8Hz, 1H), 4.49(ABq, J=17.0Hz, Δν=40.3Hz, 2H), 4.54(m, 1H), 6.82–6.89(m, 3 H), 7.02(m, 2H), 7.23(d, H=8.1 Hz, 2H), 7.42(m, 2H), 7.95(s, 1H) | C₃₄H₄₇N₅O₃ | 71.17 71.45 | 8.26 8.33 | 12.21 11.96 |
| 127 | 6-Me | MeCO | oil | 573(M⁺) | ¹H CDCl₃ 1.25–1.40(m, 2H), 1.40–1.52(m, 3H), 1.52–1.80(m, 6H), 2.02(d, J=12Hz, 2H), 2.09(s, 3H), 2.46 (s, 3H), 2.46–2.60(m, 5H), 2.75(m, 1H), 2.86(s, 2H), 2.90(d, J=15Hz, 1H), 2.95(d, J=15Hz, 1H), 3.15 (dd, J=9, 18Hz, 1H), 3.70(s, 3H), 3.95(m, 1H), 4.44 (s, 1H), 4.50–4.60(m, 2H), 6.80–6.93(m, 3H), 6.93–7.00(m, 2H), 7.14(s, 1H), 7.25(s, 1H), 7.42(d, J=9 Hz, 1H), 7.53(d, J=8Hz, 1H), 8.03(brs, 1H) | C₃₄H₄₇N₅O₃ | 71.17 70.99 | 8.26 8.05 | 12.21 12.41 |
| 128 | 7-Me | MeCO | foam | 573(M⁺) | ¹H CDCl₃ 1.32–1.41(m, 4H), 1.45–1.66(m, 6H), 1.96–2.07(m, 2H), 2.09(s, 3H), 2.19(m, 1H), 2.48–2.58(m, 8H), 2.74(m, 1H), 2.81–3.07(m, 4H), 3.14 (dd, J=4.6, 13.8Hz, 1H), 3.76(s, 3H), 3.97(dd, J=10.2, 13.8Hz, 1H), 4.47(ABq, J=17.1Hz, Δν=42.3 Hz, 2H), 4.55(m, 1H), 6.78–6.87(m, 3H), 6.96–7.07 (m, 3H), 7.23(m, 1H), 7.45(d, J=8.6Hz, 1H), 7.51 (d, J=7.6Hz, 1H), 8.18(s, 1H). | C₃₄H₄₇N₅O₃ | 71.17 71.33 | 8.26 8.20 | 12.21 12.29 |
| 129 | 5-Br | MeCO | oil | 638, 640 (M+1⁺'s for Br isotopes) Exact Mass FAB (M+1): theory 638.2706 found: 638.2729 | DMSO-d6 2:1 mixture of amide rotamers 1.20–1.60 (m, 3H), 1.60–1.90(m, 6H), 1.95(s, ⅔.3H), 2.07(s, ⅓.3H), 1.90–2.07(m, 3H), 2.55–2.90(m, 6H), 2.90–3.20(m, 4H), 3.20–3.50(m, 3H), 3.62(m, 1H), 3.73(s, 3H), 4.20–4.42(m, 3H), 6.85(m, 1H), 6.90–7.00(m, 2H), 7.10–7.30(m, 4H), 7.50(m, 1H), 7.70(s, ⅔.1H), 7.75(s, ⅓.1H), 11.10(s, 1H) | C₃₃H₄₄BrN₅O₃ | | | |
| 130 | 5-OMe | MeCO | oil | 590 (M+1⁺) | DMSO-d6 3:2 mixture of amide rotamers 1.20–1.60 (m, 12H), 1.73–1.96(m, 2H), 1.93(s, ⅗.3H), 2.02(s, ⅖.3H), 2.33–2.43(m, 4H), 2.60–2.90(m, 6H), 3.57 (m, 1H), 3.70(s, 3H), 3.71(s, 3H), 4.26–4.56(m, 3H), 6.66(d, J=6Hz, 1H), 6.82(m, 1H), 6.93(m, 2H), 7.03 (s, 2H), 7.20(m, 2H), 7.44(d, J=6Hz, ⅗.1H), 7.68 (d, J=6Hz, ⅖.1H), 10.65(s, 1H) | C₃₄H₄₇N₅O₄ | 69.24 69.52 | 8.03 8.14 | 11.87 11.92 |
| 131 | 5-OCH₂Ph | MeCO | oil | 666 (M+1⁺) | DMSO-d₆ 1.16–1.80(m, 12H), 1.90(m, 6H), 2.20–2.43 (m, 3H), 2.53–2.90(m, 6H), 3.16(m, 1H), 3.43(m, 1H), 3.60(m, 1H), 3.70(d, J=6Hz, 3H), 4.20–4.60(m, 3H), 6.73–6.88(m, 3H), 6.88–7.00(m, 2H), 7.04(s, 1H), 7.15–7.26(m, 3H), 7.26–7.40(m, 3H), 7.40–7.53 (m, 2H), 10.70(s, 1H) | C₄₀H₅₁N₅O₄ | 72.15 71.95 | 7.72 7.66 | 10.52 10.31 |
| 131a | 6-F | MeCO | foam | 577 (M⁺) | CDCl₃ δ 1.32–1.46(m, 4H), 1.58–1.66(m, 6H), 1.97–2.08(m, 2H), 2.11(s, 3H), 2.19(m, 1H), 2.49(m, 5H), | C₃₃H₄₄FN₅O₃ | 68.61 68.76 | 7.68 7.86 | 12.12 12.28 |

-continued

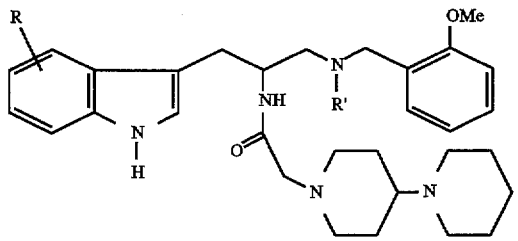

| Example No. | R | R' | Mp °C. | MS | ¹H NMR | Formula | Analysis, Theory/Found | | |
|---|---|---|---|---|---|---|---|---|---|
| | | | | | | | C | H | N |
| | | | | | 2.72–3.04(m, 5H), 3.13(dd, J=4.5Hz, Δυ=13.9Hz, 1H), 3.76(s, 3H), 3.97(dd, J=10.3Hz, Δυ=13.7Hz, 1H), 4.47(ABq, J=17.0Hz, Δυ=42.7Hz, 2H), 4.49(m, 1H), 6.78–6.90(m, 1H), 7.00(s, 1H), 7.04(d, 2.2Hz, 1H), 7.23(m, 1H), 7.47(d, J=8.5Hz, 1H), 7.57(dd, J=5.3Hz, Δυ=8.7Hz, 1H), 8.62(s, 1H) | | | | |

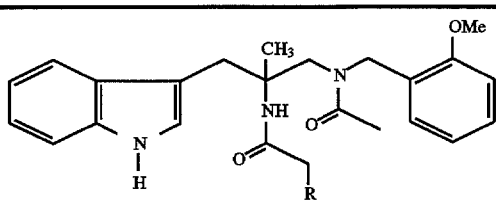

| Example No. | R | Mp °C. | MS | ¹H NMR | Formula | Analysis, % Theory/Found | | |
|---|---|---|---|---|---|---|---|---|
| | | | | | | C | H | N |
| 132 | 1-(4-(1-piperidinyl)-piperidinyl) | foam | 574 (M+1⁺) | ¹H CDCl₃ 1.44(s, 3H), 1.40–2.00(m, 13H), 2.08(s, 3H), 2.20–2.40(m, 2H), 2.45–2.80(m, 6H), 3.16–3.35(m, 2H), 3.66(d, J=14Hz, 1H), 3.81(s, 3H), 4.23 (d, J=14Hz, 1H), 4.60(ABq, J=14Hz, Δυ=28Hz, 2H), 6.86 (d, J=8Hz, 1H), 6.96(d, J=8 Hz, 1H), 7.03–7.20(m, 4H), 7.27(s, 2H), 7.40(d, J=8Hz, 1H), 7.60(d, J=6Hz, 2H) | $C_{34}H_{47}N_5O_3$ | 71.17 70.94 | 8.26 8.38 | 12.21 12.28 |
| 133 | 1-(4-phenyl)-piperazinyl | foam | 568 (M+1⁺) | ¹H CDCl₃ 1.56(s, 3H), 2.09(s, 3H), 2.43–2.85(m, 3H), 2.85–3.20(m, 7H), 3.20–3.50(m, 3H), 3.81(s, 3H), 4.20(d, J=14Hz, 1H), 4.60(ABq, J=18Hz, Δυ=56Hz, 2H), 6.80–7.00(m, 6H), 7.00–7.20(m, 3H), 7.20–7.36(m, 5H), 7.59(d, J=7Hz, 1H), 8.24(s, 1H). | $C_{34}H_{41}N_5O_3$ | 71.93 71.68 | 7.28 7.49 | 12.34 12.29 |

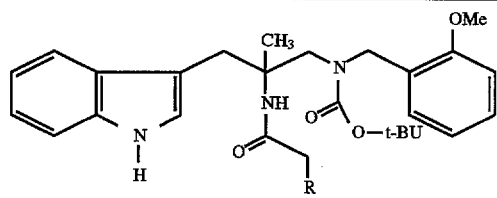

| Example No. | R | Mp °C. | MS | $^1$H NMR | Formula | Analysis, % Theory/Found | | |
|---|---|---|---|---|---|---|---|---|
| | | | | | | C | H | N |
| 134 | Br | foam | 543, 545 (M+'s for Br isotopes) | $^1$H CDCl$_3$ 1.31(s, 12H), 3.07 (d, J=14Hz, 1H), 3.25(d, J=14 Hz, 1H), 3.40(d, J=14Hz, 1H), 3.66(s, 3H), 3.68(d, J=14Hz, 1H), 3.80–3.95(m, 2H), 4.23(d, J=16Hz, 1H), 4.64(d, J=16Hz, 1H), 6.82(d, J=8Hz, 1H), 6.90 (m, 1H), 7.00–7.15(m, 2H), 7.15–7.30(m, 3H), 7.30–7.40(m, 2H), 7.55(d, J=8Hz, 1H), 8.07 (brs, 1H). | C$_{27}$H$_{34}$BrN$_3$O$_4$ | 59.56 58.80 | 6.29 6.21 | 7.72 7.47 |

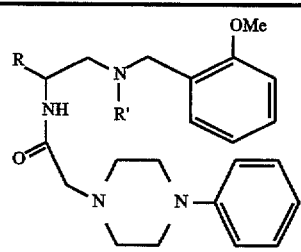

| Example No. | R | R' | Mp °C. | MS | $^1$H NMR | Formula | Analysis, % Theory/Found | | |
|---|---|---|---|---|---|---|---|---|---|
| | | | | | | | C | H | N |
| 135 | 1-naphthyl-CH$_2$ | H | foam | 523 (M+1$^+$) | CDCl$_3$ 2.32–2.45(m, 2H), 2.40 (m, 1H), 2.45–2.57(m, 2H), 2.75–3.10(m, 8H), 3.36(m, 2H), 3.84(s, 3H), 3.92(ABq, J=12 Hz, Δν=22Hz, 2H), 4.48(m, 1H), 6.75–7.00(m, 5H), 7.15–7.42(m, 6H), 7.42–7.64(m, 3H), 7.74(d, J=8Hz, 1H), 7.83(d, J=8Hz, 1H), 8.28(d, J=8Hz, 1H) | C$_{33}$H$_{38}$N$_4$O$_2$ | 75.83 75.55 | 7.33 7.26 | 10.72 10.60 |
| 136 | 2-naphthyl-CH$_2$ | H | foam | 522 (M$^+$) | CDCl$_3$ 2.03(m, 1H), 2.26–2.35 (m, 2H), 2.35–2.55(m, 2H), 2.65–2.95(m, 7H), 2.95–3.10(m, 2H), 3.18(dd, J=8, 14Hz, 1H), 3.74–4.03(m, 2H), 3.85(s, 3H), 4.45(m, 1H), 6.75(d, J=9Hz, 2H), 6.78–6.97(m, 3H), 7.03–7.40(m, 6H), 7.40–7.52(m, 2H), 7.63(s, 1H), 7.66–7.83(m, 3H) | C$_{33}$H$_{38}$N$_4$O$_2$ | 75.83 76.07 | 7.33 7.25 | 10.72 10.66 |
| 137 | 3-indolinyl-CH$_2$ | H | foam | 514 (M+1$^+$) | DMSO-d$_6$ 1:1 mixture of diastereomers 1.54–1.70(m, 1H), 1.86–1.98(m, 1H), 2.52–2.64(m, 6H), 2.84–3.18(m, 8H) 3.32(br s, 1H), 3.54(m, 1H), 3.64–3.70(m, 2H), 3.76(s, 1/2.3H), 3.78(s, 1/2.3H), 4.03 (m, 1H), 5.40(br s, 1H), 6.44–6.56(m, 2H), 6.77(t, J=7Hz, 1H), 6.82–6.98(m, 6H), 7.10–7.24(m, 3H), 7.30(br d, J=8 Hz, 1H), 7.65(t, J=9Hz, 1H) | C$_{31}$H$_{39}$N$_5$O$_2$ | 72.48 72.57 | 7.65 7.50 | 13.63 13.70 |
| 138 | Ph | MeCO | oil | 500 (M$^+$) | CDCl$_3$ 2.14(s, 3H), 2.60–2.80 (m, 4H), 3.00–3.20(m, 2H), | C$_{30}$H$_{36}$N$_4$O$_3$ | 71.97 71.67 | 7.25 7.29 | 11.19 11.18 |

-continued

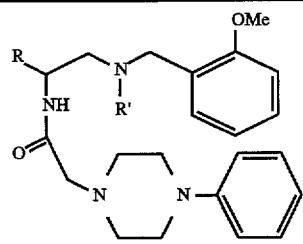

| Example No. | R | R' | Mp °C. | MS | ¹H NMR | Formula | Analysis, % Theory/Found C | H | N |
|---|---|---|---|---|---|---|---|---|---|
| 139 | 3,4-diCl Ph | MeCO | oil | 568 (M⁺) | 3.20–3.43(m, 5H), 3.82(s, 3H), 4.30(m, 1H), 4.40–4.63(m, 2H), 5.18(m, 1H), 6.80–7.06(m, 6H), 7.03–7.40(m, 8H), 8.24(br s, 1H) ¹H CDCl₃ 2.19(s, 3H), 2.63–2.83(m, 2H), 2.93–3.20(m, 4H), 3.20–3.50(m, 3H), 3.50–3.70(m, 2H), 3.85(s, 3H), 4.23(m, 1H), 4.30–4.60(m, 2H), 5.00(m, 1H), 6.85–7.06(m, 5H), 7.13(m, 1H), 7.20–7.45(m, 6H), 8.41(br s, 1H). | $C_{30}H_{34}Cl_2N_4O_3$ | 63.27 63.12 | 6.02 5.82 | 9.84 9.55 |
| 140 | PhCH₂ | MeCO | oil | 514 (M⁺) | DMSO-d₆ 3:2 mixture of amide rotamers 1.93(s, 3/5.3H), 2.09 (s, 2/5.3H), 2.23–2.46(m, 4H), 2.60–2.90(m, 4H), 3.00–3.20(m, 2H), 3.30–3.53(m, 4H), 3.75(s, 3H), 4.20–4.60(m, 3H), 6.70–7.04(m, 7H), 7.04–7.30(m, 7H), 7.57(d, J=9Hz, 3/5.1H), 7.71 (d, J=9Hz, 2/5.1H) | $C_{31}H_{38}N_4O_3$ | 72.35 72.57 | 7.44 7.47 | 10.89 10.69 |
| 141 | 1-naphthyl-CH₂ | MeCO | foam | 564 (M⁺) | CDCl₃ 2.13(s, 3H), 2.38–2.70(m, 4H), 2.82–3.07 (m, 4H), 3.07–3.30(m, 4H), 3.56(dd, J=7, 14Hz, 1H), 3.66(s, 3H), 4.14(m, 1H), 4.34(ABq, J=16 Hz, Δv=58Hz, 2H), 4.47(m, 1H), 6.52–6.67(m, 2H), 6.73(d, J=8Hz, 1H), 6.77–7.00(m, 3H), 7.09–7.20(m, 1H), 7.20–7.40(m, 4H), 7.43–7.70 (m, 3H), 7.73(d, J=8Hz, 1H), 7.86(d, J=8Hz, 1H), 8.34(d, J=8Hz, 1H) | $C_{35}H_{40}N_4O_3$ | 74.44 74.50 | 7.14 7.25 | 9.92 9.94 |
| 142 | 2-naphthyl-CH₂ | MeCO | foam | 564 (M⁺) | CDCl₃ 2.12(s, 3H), 2.26–2.50(m, 4H), 2.59–3.30 (m, 9H), 3.78(s, 3H), 3.98(m, 1H), 4.51(ABq, J=17Hz, Δv=30Hz, 2H), 4.53(m, 1H), 6.55–7.03(m, 6H), 7.05–7.39(m, 5H), 7.39–7.53(m, 2H), 7.60(m, 1H), 7.71–7.85(m, 3H) | $C_{35}H_{40}N_4O_3$ | 74.44 74.46 | 7.14 7.31 | 9.92 9.94 |
| 143 | 3-benzo[b]thienyl-CH₂ | MeCO | foam | 571 (M+1⁺) | ¹H CDCl₃ 2.15(s, 3H), 2.44–2.60(m, 4H), 2.89–3.26(m, 9H), 3.73(s, 3H), 4.07(dd, J=10.4, 13.9 Hz, 1H), 4.43(ABq, J=16.5Hz, Δv=45.4Hz, 2H), 4.50(m, 1H), 6.74–6.92(m, 6H), 7.15(s, 1H), 7.18–7.30(m, 3H), 7.39(m, 2H), 7.57(d, J=8.1Hz, 1H), 7.87(d, J=7.4Hz, 1H), 7.98(d, J=7.6Hz, 1H). | $C_{33}H_{38}N_4O_3S$ | 69.45 69.23 | 6.71 6.71 | 9.82 9.77 |
| 144 | 3-indolinyl-CH₂ | MeCO | 102–105 | 556 (M+1⁺)Exact Mass FAB (M+1): calc.: 556.3287 found: 556.3280 | CDCl₃ 1:1 mixture of diastereomers 1.57–2.08 (m, 2H), 2.15(s, 1/2.3H), 2.17(s, 1/2.3H), 2.75–3.60(m, 13H), 3.65–4.00(m, 2H), 3.82(s, 1/2.3H), 3.85(s, 1/2.3H), 4.18–4.48(m, 2H), 4.58(s, 2H), 6.70–7.40(m, 13H), 7.67(m, 1H) | $C_{33}H_{41}N_5O_3$ | | | |
| 145 | N-Ac-3-indolinyl-CH₂ | MeCO | 80–84 | 597(M⁺) Exact Mass FAB (M+1): calc.: 598.3393 found: 598.3397 | CDCl₃ 1:1 mixture of diastereomers 1.70–2.00 (m, 2H), 2.13(s, 1/2.3H), 2.17(s, 1/2.3H), 2.23 (s, 1/2.3H), 2.27(s, 1/2.3H), 2.57–3.53(m, 12H), 3.63–4.03(m, 2H), 3.82(s, 1/2.3H), 3.85 (s, 1/2.3H), 4.03–4.33(m, 2H), 4.52(s, 1/2.1H), 4.54(s, 1/2.1H), 6.80–7.40(m, 12H), 7.57(m, 1H), 8.19(m, 1H) | $C_{35}H_{43}N_5O_4$ | | | |

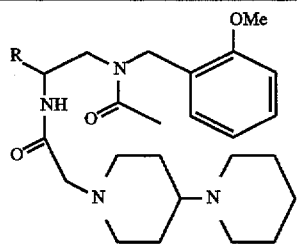

| Example No. | R | Mp °C. | MS | $^1$H NMR | Formula | Analysis, % Theory/Found C | H | N |
|---|---|---|---|---|---|---|---|---|
| 146 | Ph | oil | 506(M$^+$) | DMSO-d6 2:1 mixture of amide rotamers 1.30–1.76 (m, 11H), 1.90–2.20(m, 4H), 1.96(s, 2/3 .3H), 2.00(s, 1/3 .3H), 2.35–2.55(m, 4H), 2.60–2.95(m, 4H), 3.78(s, 3H), 4.43(s, 2/3 .2H), 4.43(ABq, J=15Hz, Δv=49Hz, 1/3 .2H), 4.96(m, 2/3 .1H), 5.24(m, 1/3 .1H), 6.80–7.05 (m, 3H), 7.15–7.40(m, 6H), 8.26(d, J=9Hz, 1H) | $C_{30}H_{42}N_4O_3$ | 71.11 / 71.38 | 8.35 / 8.25 | 11.06 / 11.07 |
| 147 | 3,4-diCl-Ph | oil | FD 574(M$^+$) FAB Exact Mass Theory: 575.2555 Found: 575.2595 (M+1$^+$) | $^1$H CDCl$_3$ 1.40–1.60(m, 2H), 1.60–1.80(m, 4H), 1.80–2.05(m, 5H), 2.17(s, 3H), 2.18(m, 1H), 2.40–2.80(m, 5H), 2.80–3.05(m, 5H), 3.85(s, 3H), 4.23(ABq, J=11 Hz, Δv=14Hz, 1H), 4.48(ABq, J=17Hz, Δv=33Hz, 2H), 4.93(m, 1H), 6.85–7.10(m, 4H), 7.20–7.40(m, 3H), 8.35(m, 1H) | $C_{30}H_{40}Cl_2N_4O_3$ | 62.60 / 63.05 | 7.01 / 6.91 | 9.73 / 9.78 |
| 148 | PhCH$_2$ | oil | 520(M$^+$) | DMSO 3:2 mixture of amide rotamers 1.30–1.63 (m10H), 1.73–2.00(m, 3H), 1.88(s, 3/5.3H), 2.07(s, 2/5.3H), 2.40(m, 3H), 2.55–2.80(m, 4H), 3.15–3.50(m, 5H), 3.76(s, 3H), 4.20–4.60(m, 3H), 6.80–7.00(m, 3H), 7.05–7.30(m, 6H), 7.49(d, J=9Hz, 3/5.1H), 7.62(d, J=9Hz, 2/5.1H) | $C_{31}H_{44}N_4O_3$ | 71.51 / 71.50 | 8.52 / 8.25 | 10.76 / 10.51 |
| 149 | 3-benzo[b]thienyl CH$_2$ | foam | 576 (M$^+$) | $^1$H CDCl$_3$ 1.41–1.73(m, 9H), 2.00–2.21(m, 7H), 2.41–2.48(m, 4H), 2.59(d, J=11.4Hz, 1H), 2.74(d, J=12.6 Hz, 1H), 2.88(s, 3H), 3.04(dd, J=4.3, 13.9Hz, 1H), 3.20(dd, J=6.1, 14.5Hz, 1H), 3.70(s, 3H), 4.04(dd, J=10.5, 13.9Hz, 1H), 4.40(ABq, J=16.5Hz, Δv=46.1 Hz, 2H), 4.50(m, 1H), 6.73(m, 2H), 6.78(d, J=8.2Hz, 1H), 7.13(s, 1H), 7.19(m, 1H), 7.27(m, 2H), 7.57(d, J=8.1Hz, 1H), 7.84(d, J=7.5Hz, 1H), 7.96(d, J=7.6 Hz, 1H) | $C_{33}H_{44}N_4O_3S$ | 68.72 / 68.47 | 7.69 / 7.79 | 9.71 / 9.77 |

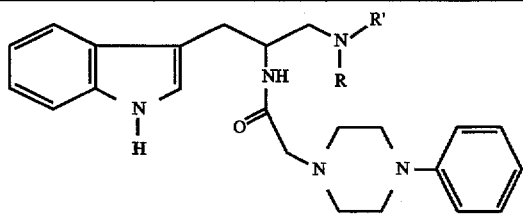

| Example No. | R | R' | Mp °C. | MS | $^1$H NMR | Formula | Analysis % Theory/Found C | H | N |
|---|---|---|---|---|---|---|---|---|---|
| 150 | H | H | 144–145 | 391 (M$^+$) | CDCl$_3$ 2.18–2.42(m, 2H), 2.42–2.77 (m, 4H), 2.77–3.50(m, 10H), 4.43 (m, 1H), 6.73–7.00(m, 3H), 7.07–7.59(m, 7H), 7.64(d, J=8Hz, 1H), 8.24(br s, 1H) | $C_{23}H_{29}N_5O$ | 70.56 / 70.51 | 7.47 / 7.60 | 17.89 / 17.91 |
| 151 | t-Bu-O(CO) | H | 121–122 | 491 (M$^+$) | CDCl$_3$ 1.63(s, 9H), 2.22–2.67(m, 4H), 2.75–3.23(m, 8H), 3.30(m, 1H), 3.40(m, 1H), 4.41(m, 1H), 5.03(m, 1H), 6.75–7.00(m, 4H), 7.07–7.70(m, 6H), 7.65(d, J=8Hz, 1H), 8.18(br s, 1H) | $C_{28}H_{37}N_5O_3$ | 68.40 / 68.16 | 7.59 / 7.56 | 14.25 / 14.05 |
| 152 | PhCO | H | 188–189 | 495 (M$^+$) | CDCl$_3$/DMSOd$_6$ 1.90–2.74(m, 6H), 2.74–3.40(m, 4H), 3.11(d, | $C_{30}H_{33}N_5O_2$ | 72..70 / 72.46 | 6.71 / 6.71 | 14.13 / 13.84 |

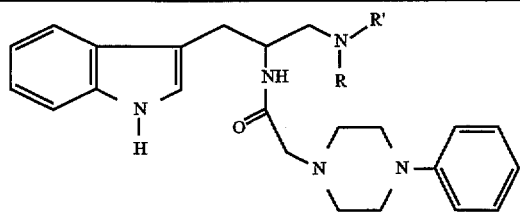

| Example No. | R | R' | Purification | Yield % | Mp °C. | MS | ¹H NMR | Formula | Analysis % Theory/Found C | H | N |
|---|---|---|---|---|---|---|---|---|---|---|---|
| 153 | H | (c-hexyl)CH₂ | | | foam | 487 (M⁺) | J=7Hz, 2H), 3.58–3.82(m, 2H), 4.55(m, 1H), 6.63–6.96(m, 3H), 7.00–7.53(m, 10H), 7.68(d, J=8 Hz, 1H), 7.60–8.00(m, 3H), 9.28 (br s, 1H) CDCl₃ 0.73–1.41(m, 6H), 1.41–2.08 (m, 8H), 2.10–3.38(m, 14H), 4.56 (m, 1H), 6.81(d, J=8Hz, 1H), 6.81–6.97(m, 4H), 7.02–7.40(m, 4H), 7.57–7.73(m, 2H), 8.10(br s, 1H) | C₃₀H₄₁N₅O | 73.88 73.60 | 8.47 8.36 | 14.36 14.24 |
| 154 | t-Bu-O(CO)NH—CH₂CO | (c-hexyl)CH₂ | chrom (EtOH/ EtOAc) | 84 mg 43% | foam | 644 (M⁺) | CDCl₃ 0.75–1.00(m, 2H), 1.00–1.94 (m, 10H), 1.44(s, 9H), 2.40–2.65 (m, 3H), 2.65–3.66(m, 11H), 3.76–4.20(m, 3H), 4.60(m, 1H), 5.54 (m, 1H), 6.75–7.05(m, 3H), 7.05–7.46(m, 7H), 7.67(d, J=8Hz, 1H), 8.13(br s, 1H) | C₃₇H₅₂N₆O₄ | 68.92 68.93 | 8.13 8.28 | 13.03 13.11 |

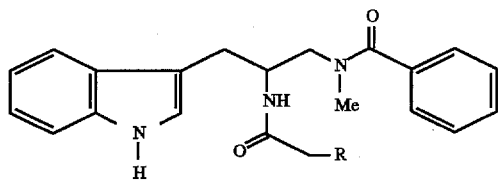

| Example No. | R | Mp °C. | MS | ¹H NMR | Formula | Analysis % Theory/Found C | H | N |
|---|---|---|---|---|---|---|---|---|
| 155 | 1-(4-1-piperidinyl)-piperidinyl | foam | 515 (M⁺) | CDCl₃ 1.3–2.1(m, 11H), 2.30(m, 1H), 2.4–3.3(m, 12H), 3.00(s, 3H), 4.28(m, 1H), 4.74(m, 1H), 7.1–7.5 (m, 10H), 7.68(d, J=8Hz, 1H), 8.83(br s, 1H) | C₃₁H₄₁N₅O₂ | 72.20 72.12 | 8.01 8.22 | 13.58 13.82 |
| 156 | 1-(4-AcNH-4-Ph-piperidinyl) | 168–9 | 565 (M⁺) | CDCl₃ 1.97(s, 3H), 2.0–2.6(m, 8H), 2.8–3.3(m, 4H), 2.99(s, 3H), 3.52(m, 1H), 4.30(m, 1H), 4.72 (m, 1H), 5.48(d, 1H), 7.0–7.7(m, 15H), 7.68(m, 1H), 8.41(br s, 1H) | C₃₄H₃₉N₅O₃ | 72.19 72.47 | 6.95 7.08 | 12.38 12.63 |
| 157 | 1-(4-Ph-piperazinyl) | foam | 509 (M⁺) | CDCl₃ 2.3–2.7(m, 3H), 2.7–3.7(m, 10H), 3.02(s, 3H), 4.30(m, 1H), 4.78(m, 1H), 6.7–6.9(m, 3H), 7.1–7.5(m, 12H), 7.70(d, J=7Hz, 1H), 8.22(br s, 1H) | C₃₁H₃₅N₅O₂ | 73.06 72.91 | 6.92 6.96 | 13.74 13.70 |
| 158 | 1-(4-cyclohexyl-piperazinyl) | foam | 515 (M⁺) | CDCl₃ 1.0–1.3(m, 6H), 1.6–2.0(m, 4H), 2.2–2.6(m, 9H), 2.9–3.2(m, 5H), 2.99(s, 3H), 4.38(m, 1H), 4.75(m, 1H), 7.1–7.5(m, 10H), 7.69(d, J=6Hz, 1H), 8.23(br s, 1H) | C₃₁H₄₁N₅O₂ | 72.40 72.20 | 8.00 8.01 | 13.66 13.58 |

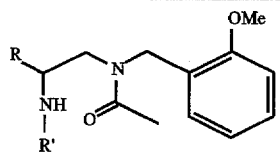

| Example No. | R | R' | Mp °C. | MS | ¹H NMR | Formula | C | H | N |
|---|---|---|---|---|---|---|---|---|---|
| 159 | PhCH₂ | H | oil | 312(M⁺) | CDCl₃ 3:1 mixture of amide rotamers 1.90–2.15(m, 2H), 2.17 (s, ¾.3H), 2.23(s, ¼.3H), 2.62 (dd, J=8, 13Hz, 1H), 2.83(dd, J=5, 13Hz, 1H), 3.26–3.55(m, 3H), 3.84 (s, 3H), 4.55(d, J=14Hz, ¾.2H), 4.63(d, J=11Hz, ¼.2H), 6.80–7.03(m, 3H), 7.13–7.36(m, 6H) | C₁₉H₂₄N₂O₂ | 73.05<br>72.82 | 7.74<br>7.68 | 8.97<br>8.80 |
| 160 | 1-Me-3-indolyl-CH₂ | H | oil | 365(M⁺) | CDCl₃ 2.00–2.30(m, 4H), 2.78(dd, J=7, 15Hz, 1H), 2.93(m, 1H), 3.30–3.60(m, 4H), 3.75(s, 3H), 3.82(s, 3H), 4.60(ABq, J=16 Hz, Δν=30, 2H), 6.83–7.00(m, 4H), 7.10(m, 1H), 7.16–7.33(m, 3H), 7.55(m, 1H) | C₂₂H₂₇N₃O₂ | 72.30<br>72.02 | 7.45<br>7.43 | 11.50<br>11.24 |
| 161 | Ph | BrCH₂CO | oil | 418, 420 (M⁺'s for Br isotopes) | CDCl₃ 2.22(s, 3H), 3.06(dd, J=3, 14Hz, 1H), 3.83(s, 2H), 3.87(s, 3H), 4.26(dd, J=11, 15Hz, 1H), 4.45(ABq, J=17Hz, Δν=62Hz, 2H), 4.93(m, 1H), 6.88–7.06(m, 3H), 7.23–7.36(m, 6H), 8.23(d, J=6Hz, 1H) | C₂₀H₂₃BrN₂O₃ | 57.29<br>57.24 | 5.53<br>5.48 | 6.68<br>6.49 |
| 161a | PhCH₂ | BrCH₂CO | oil | 432, 434 (M⁺'s for Br isotopes) | CDCl₃ 2.17(s, 3H), 2.66(dd, J=8, 14Hz, 1H), 2.84(dd, J=9, 14Hz, 1H), 2.97(dd, J=5, 14Hz, 1H), 3.73–3.85(m, 5H), 4.05(m, 1H), 4.18(m, 1H), 4.40(ABq, J=16Hz, Δν=39Hz, 2H), 6.79–6.90(m, 3H), 7.16–7.40(m, 7H) | C₂₁H₂₅BrN₂O₃ | 58.21<br>58.28 | 5.81<br>5.80 | 6.46<br>6.32 |
| 162 | 1-Me-3-indolylCH₂ | BrCH₂CO | foam | 485, 487 (M⁺'s for Br isotopes), | ¹H CDCl₃ 2.15(s, 3H), 2.90(dd, J=8, 14Hz, 1H), 2.92(dd, J=6, 14 Hz, 1H), 3.10(dd, J=4, 14Hz, 1H), 3.72(s, 3H), 3.74(s, 3H), 3.80(s, 2H), 4.07(m, 1H), 4.23–4.40(m, 2H), 4.46(m, 1H), 6.70–6.90(m, 4H), 7.13(d, J=8Hz, 1H), 7.20–7.33(m, 3H), 7.33(d, J=12Hz, 1H), 7.68(d, J=8Hz, 1H). | C₂₄H₂₈BrN₃O₃ | 59.26<br>59.50 | 5.80<br>5.76 | 8.64<br>8.52 |

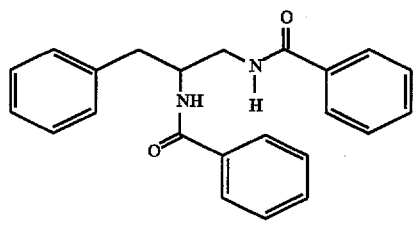

| Example No. | Mp, °C. | MS | ¹H NMR | Formula | C | H | N |
|---|---|---|---|---|---|---|---|
| 163 | 203–205 | 358(M⁺) | CDCl₃ 2.89(dd, J=9, 14Hz, 1H), 3.19(dd, J=6, 14Hz, 1H), 3.54(dt, J=4, 14Hz, 1H), 3.75(m, 1H), 4.54(m, 1H), 7.01(m, 1H), 7.15(m, 1H), 7.18–7.35(m, 4H), 7.35–7.55(m, 7H), 8.65–8.79(m, 4H) | C₂₃H₂₂N₂O₂ | 77.07<br>76.83 | 6.19<br>6.21 | 7.81<br>7.88 |

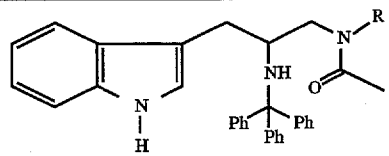

| Example No. | R | Mp, °C. | MS | ¹H NMR | Formula | Analysis % Theory/Found | | |
|---|---|---|---|---|---|---|---|---|
| | | | | | | C | H | N |
| 164 | Me | 183–184 | 488 (M+1⁺) | CDCl₃ 1.56(s, 3H), 1.90(m, 1H), 2.10(m, 1H), 2.35(m, 1H), 2.5–2.6(br s, 3H), 2.75 (m, 1H), 2.95(m, 1H), 3.20(m, 1H), 6.9–7.1(m, 2H), 7.1–7.6(m, 17H), 7.85(m, 1H), 7.96(br s, 1H) | C₃₃H₃₃N₃O | 81.28 81.26 | 6.82 6.91 | 8.62 8.71 |
| 165 | n-Bu | foam | 530 (M+1⁺) | ¹H CDCl₃ 0.51–0.81(m, 3H), 0.85–1.31 (m, 3H), 1.58(s, 1H), 1.88(s, 2H), 1.98(s, 1H), 2.00–2.10(m, 1H), 2.40–2.78(m, 3H), 2.86–3.00(m, 2H), 3.20–3.40(m, 2H), 6.88 (s, 1H), 6.89–7.08(m, 2H), 7.09–7.38(m, 11H), 7.40–7.60(m, 5H), 7.80–8.00(m, 2H). | C₃₆H₃₉N₃O | 81.63 81.90 | 7.42 7.44 | 7.93 8.03 |
| 166 | n-Hex | foam | 558 (M+1⁺) | ¹H CDCl₃ 0.80–0.88(m, 6H), 0.88–1.30(m, 7H), 1.92(s, 2H), 1.98(s, 1H), 2.20–2.72 (m, 3H), 2.85–3.02(m, 1H), 3.06–3.38(m, 2H), 6.92(s, 1H), 6.97–7.06(m, 2H), 7.11–7.38((m, 12H), 7.38–7.58(m, 5H), 7.85–7.98(m, 1H) | C₃₈H₄₃N₃O | 81.83 82.10 | 7.77 7.74 | 7.53 7.24 |
| 167 | Ph | 182–183 | 550 (M+1⁺) | ¹H DMSO 1.64(s, 3H), 2.55(m, 1H), 2.59–2.82(m, 3H), 3.30(m, 1H), 3.63(dd, J=7, 14Hz, 1H), 6.72(d, J=2Hz, 1H), 6.74–6.82 (m, 2H), 6.84(t, J=8Hz, 1H), 6.99(t, J=8 Hz, 1H), 7.05–7.21(m, 10H), 7.21–7.64(m, 10H), 10.67(br s, 1H). | C₃₈H₃₅N₃O | 83.03 82.80 | 6.42 6.65 | 7.64 7.39. |
| 168 | PhCH₂CH₂ | 174–175 | 577(M⁺) | ¹H DMSO(3:2 mixture of amide rotamers)1.77(s, ⅗.3H), 1.97(s, ⅖.3H), 2.06–2.44(m, 4H), 2.64–3.04(m, 4H), 3.18(m, 1H), 3.38–3.61(m, 1H), 6.61–6.71(m, 2H), 6.88(m, 1H), 6.96–7.08(m, 2H), 7.08–7.34(m, 14H), 7.41–7.56(m, 6H), 10.78(br s, 1H). | C₄₀H₃₉N₃O | 83.15 82.92 | 6.80 6.83 | 7.27 7.57 |

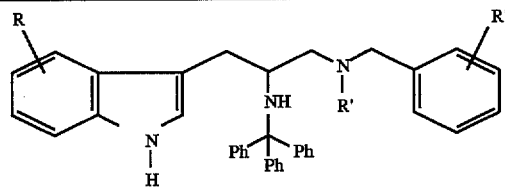

| Example No. | R | R' | R" | Mp, °C. | MS | ¹H NMR | Formula | Analysis % Theory/Found | | |
|---|---|---|---|---|---|---|---|---|---|---|
| | | | | | | | | C | H | N |
| 169 | 6-Me | H | 2-OMe | oil | 566 (M+1⁺) | CDCl₃ 1.90(m, 1H), 2.18–2.33(m, 2H), 2.44(s, 3H), 2.60(m, 1H), 2.68–2.96(m, 2H), 3.48–3.68(m, 3H), 3.80(s, 3H), 6.86(d, J=8Hz, 3H), 6.99–7.46(m, 15H), 7.46–7.73(m, 5H), 7.76(s, 1H) | C₃₉H₃₉N₃O | 82.80 82.81 | 6.95 7.02 | 7.43 7.32 |
| 170 | H | MeCO | 2-Cl | foam | 598 (M+1) | CDCl₃ 3:2 mixture of amide rotamers 1.80(s, ⅗.3H), 2.05(s, ⅖.3H), 2.30–2.53(m, 2H), 2.65(m, 1H), 3.00–3.33(m, 3H), 3.91(ABq, J=20Hz, Δv=30Hz, ⅗.2H), 4.61(ABq, J=18Hz, Δv=77Hz, ⅖.2H), 6.58–6.67(m, ⅗.1H), 6.80–6.89(m, ⅖.1H), 6.94–7.33(m, 18H), 7.42–7.56(m, 5H), 7.86(br s, 1H) | C₃₉H₃₆ClN₃O | 78.37 78.10 | 6.07 6.25 | 7.02 6.78 |
| 171 | 6-Me | MeCO | 2-OMe | oil | 608 (M+1⁺) | CDCl₃ 3:1 mixture of amide rotamers 1.92(s, ¾.3H), 1.97(s, ¼.3H), 2.44(s, 3H), 2.56–2.76(m, 2H), 3.04–3.36(m, 4H), 3.62(s, 1H), 3.72(s, 3H), 4.03(d, J=18 Hz, 1H), 6.43(d, J=9Hz, 1H), 6.58–7.00(m, 4H), 7.00–7.28(m, 11H), 7.40–7.60(m, 7H), 7.74(br s, 1H) | C₄₁H₄₁N₃O₂ | 81.02 80.90 | 6.80 6.66 | 6.91 7.16 |

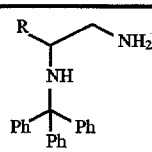

| Example No. | R | Mp, °C. | MS | ¹H NMR | Formula | Analysis % Theory/Found | | |
|---|---|---|---|---|---|---|---|---|
| | | | | | | C | H | N |
| 172 | 3,4-diCl-Ph | oil | 447 (M+1⁺) | ¹H CDCl₃ 1.50–1.95(m, 2H), 2.04 (dd, J=6, 13Hz, 1H), 2.52(dd, J=4, 12Hz, 1H), 2.90(m, 1H), 3.67(m, 1H), 7.03(m, 1H), 7.06–7.36(m, 12H), 7.40–7.55(m, 5H). | $C_{27}H_{24}Cl_2N_2$ | 72.48 72.45 | 5.41 5.38 | 6.26 6.02 |

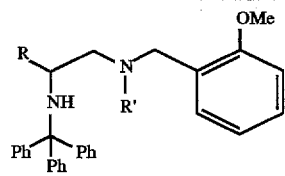

| Example No. | R | R' | Mp, °C. | MS | ¹H NMR | Formula | Analysis % Theory/Found | | |
|---|---|---|---|---|---|---|---|---|---|
| | | | | | | | C | H | N |
| 173 | Ph | H | oil | 499 (M+1⁺) | CDCl₃ 2.25–2.36(m, 2H), 3.06(m, 1H), 3.40–3.50(m, 2H), 3.54(s, 3H), 3.75–3.90 (m, 2H), 6.74(d, J=8Hz, 1H), 6.85(m, 1H), 6.98(m, 1H), 7.03–7.40(m, 15H), 7.45–7.60(m, 6H) | $C_{35}H_{34}N_2O$ | 84.30 84.47 | 6.87 6.87 | 5.62 5.74 |
| 174 | PhCH₂ | H | oil | 513 (M+1⁺) | CDCl₃ 1.93–2.10(m, 2H), 2.20(m, 1H), 2.23–2.40(m, 2H), 2.60(m, 1H), 2.75(m, 1H), 2.55–3.65(m, 2H), 3.82(s, 3H), 6.83–6.98(m, 4H), 7.03–7.40(m, 14H), 7.53–7.66(m, 6H) | $C_{36}H_{36}N_2O$ | 84.34 84.41 | 7.08 6.95 | 5.46 5.76 |
| 175 | Ph | MeCO | foam | 540(M⁺) | CDCl₃ 2:1 mixture of amide rotamers 1.9 (s, ⅔3H), 1.96(s, ⅓3H), 2.93(m, 1H), 3.05(m, 1H), 3.67(s, ⅔3H), 3.75(s, ⅓3H), 3.75(m, 1H), 3.93(d, J=18Hz, 2H), 4.21(ABq J=14Hz, Δv=21Hz, 1H), 6.66–6.90(m, 3H), 6.90–7.35(m, 15H), 7.35–7.55(m, 6H) | $C_{37}H_{36}N_2O_2$ | 82.19 82.37 | 6.71 6.69 | 5.18 5.03 |
| 176 | 3,4-diCl-Ph | MeCO | 181–182.5 | 608(M⁺) for Cl isotope), Exact M.S. Theory: 609.2075, Found: 609.2053 | ¹H CDCl₃ 1.99(s, 3H), 2.96(dd, J=6, 14 Hz, 1H), 3.12(m, 1H), 3.60(dd, J=8, 14 Hz, 1H), 3.81(s, 3H), 3.90–4.16(m, 3H), 6.73–6.96(m, 4H), 6.96–7.30(m, 12H), 7.30–7.49(m, 6H) | $C_{37}H_{34}Cl_2N_2O_2$ | 72.90 73.56 | 5.62 5.70 | 4.59 4.66 |
| 177 | PhCH₂ | MeCO | foam | 554(M⁺) | CDCl₃ 2:1 mixture of amide rotamers 1.90 (s, ⅔3H), 1.95(s, ⅓3H), 2.36–2.53(m, 2H), 2.63(dd, J=4, 13Hz, 1H), 3.00(m, 1H), 3.06–3.23(m, 2H), 3.66(s, ⅓3H), 3.76(s, ⅔3H), 3.85(ABq, J=17Hz, Δv=110Hz, ⅔2H), 4.59(ABq, J=17Hz, Δv=100Hz, ⅓2H), 6.42(d, J=7Hz, 1H), 6.68–6.85(m, 3H), 6.92–7.05(m, 2H), 7.05–7.43(m, 12H), 7.50–7.63(m, 6H) | $C_{38}H_{38}N_2O_2$ | 82.28 82.01 | 6.90 6.96 | 5.05 5.25 |

The biological activity of the compounds of the present invention was evaluated employing an initial screening assay which rapidly and accurately measured the binding of the tested compound to known NK-1 and NK-2 receptor sites. Assays useful for evaluating tachykinin receptor antagonists are well known in the art. See, e.g., J. Jukic, et al., *Life Sciences*, 49:1463–1469 (1991); N. Kucharczyk, et al., *Journal of Medicinal Chemistry*, 36:1654–1661 (1993); N. Rouissi, et al., *Biochemical and Biophysical Research Communications*, 176:894–901 (1991).

NK-1 Receptor Binding Assay

Radioreceptor binding assays were performed using a derivative of a previously published protocol. D. G. Payan, et al., *Journal of Immunology*, 133:3260–3265 (1984). In this assay an aliquot of IM9 cells ($1\times10^6$ cells/tube in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well-characterized and readily available human cell line. See, e.g., *Annals of the New York Academy of Science*, 190:221–234 (1972); *Nature* (London), 251:443–444 (1974); *Proceedings of the National Academy of Sciences* (USA), 71:84–88 (1974). These cells were routinely cultured in RPMI 1640 supplemented with 50 µg/ml gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

NK-2 Receptor Binding Assay

The CHO—hNK-2R cells, a CHO-derived cell line transformed with the human NK-2 receptor, expressing about 400,000 such receptors per cell, were grown in 75 cm² flasks or roller bottles in minimal essential medium (alpha modification) with 10% fetal bovine serum. The gene sequence of the human NK-2 receptor is given in N. P. Gerard, et al,, *Journal of Biological Chemistry*, 265:20455–20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets were washed once using the above procedure, and the final pellets were resuspended in 100–120 ml 50 mM Tris buffer, pH 7.4, and 4 ml aliquots stored frozen at –70° C. The protein concentration of this preparation was 2 mg/ml.

For the receptor binding assay, one 4-ml aliquot of the CHO-hNK-2R membrane preparation was suspended in 40 ml of assay buffer containing 50 mM Tris, pH 7.4, 3 mM manganese chloride, 0.02% bovine serum albumin (BSA) and 4 µg/ml chymostatin. A 200 µl volume of the homogenate (40 µg protein) was used per sample. The radioactive ligand was [$^{125}$I]iodohistidyl-neurokinin A (New England Nuclear, NEX-252), 2200 Ci/mmol. The ligand was prepared in assay buffer at 20 nCi per 100 µl; the final concentration in the assay was 20 pM. Non-specific binding was determined using 1 µM eledoisin. Ten concentrations of eledoisin from 0.1 to 1000 nM were used for a standard concentration-response curve.

All samples and standards were added to the incubation in 10 µl dimethylsulfoxide (DMSO) for screening (single dose) or in 5 µl DMSO for IC$_{50}$ determinations. The order of additions for incubation was 190 or 195 µl assay buffer, 200 µl homogenate, 10 or 5 µl sample in DMSO, 100 µl radioactive ligand. The samples were incubated 1 hr at room temperature and then filtered on a 48 well Brandel cell harvester through GF/B filters which had been presoaked for two hours in 50 mM Tris buffer, pH 7.7, containing 0.5% BSA. The filter was washed 3 times with approximately 3 ml of cold 50 mM Tris buffer, pH 7.7. The filter circles were then punched into 12×75 mm polystyrene tubes and counted in a gamma counter.

Table II, infra, depicts the results of several such neurokinin binding assays. Column 1 provides the example number of the test antagonist compound as detailed in Table 1, supra. The next colums define the the concentration of the test compound (in nanomolar quantities) which inhibits fifty percent of the binding of the appropriate neurokinin, as defined in the column heading, or the percent inhibition of such binding at the concentration noted. Certain values represent the average of more than one experiment.

TABLE II

| Example No. | NK-1 IC$_{50}$ nM | NK-2 IC$_{50}$ nM |
|---|---|---|
| 1 | 53 | 1700 |
| 2 | 36 | |
| 3 | 29 | |
| 4 | 40 | 1500 |
| 5 | 62 | |
| 6 | 62% @ 1 µM | |
| 7 | 230 | |
| 8 | 130 | |
| 9 | 84 | 640 |
| 10 | 19 | 820 |
| 11 | 65 | 2400 |
| 12 | 1.6 | 1600 |
| 13 | 1.3 | |
| 14 | 3.1 | 1000 |
| 15 | 2.1 | |
| 16 | 4.2 | 1200 |
| 17 | 0.85 | 1600 |
| 18 | 1.1 | |
| 19 | 434 | |
| 20 | 6.0 | 870 |
| 21 | 4.6 | 1200 |
| 22 | 2.1 | 3300 |
| 23 | 13 | 810 |
| 24 | 1.2 | 640 |
| 25 | 4.4 | 480 |
| 26 | 0.75 | 650 |
| 27 | 1.6 | 710 |
| 28 | 1.7 | 1000 |
| 29 | 1.5 | 1500 |
| 30 | 1.0 | 680 |
| 31 | 9.2 | 6200 |
| 32 | 0.98 | 1100 |
| 33 | 1.9 | 670 |
| 34 | 6.2 | 590 |
| 35 | 0.89 | 600 |
| 36 | 10 | 120 |
| 37 | 4.2 | 600 |
| 38 | 30% @ 5 µM | 8000 |
| 39 | 139 | |
| 40 | 21.3 | 910 |
| 41 | 7.7 | 930 |
| 42 | 16% @ 1 µM | 1200 |
| 43 | 179 | 39 |
| 44 | 25 | 54% at 10 µM |
| 45 | 65 | 5300 |
| 46 | 2.2 | 2400 |
| 47 | 0.25 | 1800 |
| 48 | 0.24 | |

TABLE II-continued

| Example No. | NK-1 IC$_{50}$ nM | NK-2 IC$_{50}$ nM |
|---|---|---|
| 49 | 135 | |
| 50 | 0.25 | 3400 |
| 51 | 0.37 | |
| 52 | 250 | |
| 53 | 58% @ 5 μM | 5200 |
| 54 | 30.1 | 2100 |
| 55 | 71 | |
| 56 | | |
| 57 | 150 | |
| 58 | 14 | 340 |
| 59 | 7.3 | 3700 |
| 60 | 24 | 3900 |
| 61 | 7.2 | 940 |
| 62 | 43 | 5900 |
| 63 | 74 | 490 |
| 64 | 30 | 240 |
| 65 | 72 | 600 |
| 66 | 4.6 | 7200 |
| 67 | 3.8 | 750 |
| 68 | 0.41 | 2400 |
| 69 | 5.4 | 830 |
| 70 | 13 | 1000 |
| 71 | 7.5 | 8900 |
| 73 | 0.99 | |
| 74 | 0.36 | 1000 |
| 75 | 0.18 | 850 |
| 76 | 69 | 1400 |
| 77 | 0.88 | 630 |
| 78 | 10 | 2100 |
| 79 | 38 | 6100 |
| 80 | 19 | 3400 |
| 81 | 13 | 1100 |
| 82 | 13 | 1200 |
| 83 | 8.4 | 5200 |
| 84 | 41.1 | 510 |
| 86 | 0.36 | |
| 87 | 0.77 | |
| 88 | 120 | 5600 |
| 89 | 170 | 1200 |
| 90 | 65 | |
| 91 | 3000 | |
| 92 | 97.2 | |
| 93 | 16% @ 1 μM | |
| 94 | 85 | 760 |
| 95 | 9.6 | 1000 |
| 96 | 34.4 | |
| 97 | 1300 | |
| 98 | 21 | 600 |
| 99 | 15% @ 1 μM | 54% @ 10 μM |
| 100 | 77% @ 1 μM | 40% @ 10 μM |
| 101 | 97 | 6000 |
| 102 | 210 | 59% @ 10 μM |
| 103 | 82 | 3700 |
| 104 | 0.62 | 1600 |
| 105 | 630 | 15200 |
| 106 | 68 | 33% @ 10 μM |
| 107 | 74% @ 1 μM | 420 |
| 108 | 76% @ 1 μM | 3500 |
| 109 | 190 | 2000 |
| 110 | 148 | 120 |
| 111 | 1200 | 490 |
| 112 | 270 | |
| 113 | 7.8 | 1200 |
| 114 | 29.2 | 940 |
| 115 | 15.4 | |
| 116 | 58 | 930 |
| 117 | 33 | |
| 118 | 310 | |
| 119 | 9.5 | 2700 |
| 120 | 2500 | |
| 121 | 850 | |
| 122 | 550 | |
| 123 | 27 | 2500 |
| 124 | 0.93 | 1400 |
| 125 | 0.66 | 2100 |
| 126 | 28 | 3400 |
| 127 | 7.3 | 3000 |
| 128 | 1.1 | |
| 129 | 8.5 | |
| 130 | 19 | |
| 131 | 67 | |
| 131a | 0.7 | |
| 132 | 4.2 | |
| 133 | 11.6 | |
| 134 | 14% @ 1 μM | |
| 135 | 75% @ 1 μM | 430 |
| 136 | 47% @ 1 μM | 710 |
| 137 | 220 | 2700 |
| 138 | 770 | 2500 |
| 139 | 396 | 580 |
| 140 | 3.1 | 3000 |
| 141 | 11 | 260 |
| 142 | 8.6 | 830 |
| 143 | 7.9 | |
| 144 | 52 | 1200 |
| 145 | 76 | 1900 |
| 146 | 420 | 3900 |
| 147 | 196 | 430 |
| 148 | 24 | 8500 |
| 149 | 1.2 | |
| 150 | 45% @ 1 μM | |
| 151 | 1400 | 1700 |
| 152 | 1200 | 2000 |
| 153 | 650 | 540 |
| 154 | 76% @ 1 μM | 210 |
| 155 | 63% @ 5 μM | 12200 |
| 156 | 78% @ 5 μM | 9500 |
| 157 | 88% @ 5 μM | 2900 |
| 158 | 450 | 3800 |
| 159 | 54% @ 5 μM | 11 @ 10 μM |
| 160 | 0% @ 5 μM | 19000 |
| 161 | 24% @ 5 μM | 0% @ 10 μM |
| 161a | 77% @ 5 μM | 17600 |
| 162 | 375 | 0% @ 10 μM |
| 163 | | 44% @ 10 μM |
| 164 | 0% @ 5 μM | 6200 |
| 165 | 3% @ 5 μM | 10450 |
| 166 | 0% @ 5 μM | 10000 |
| 167 | 0% @ 5 μM | 21000 |
| 168 | 13% @ 5 μM | >100000 |
| 169 | 8% @ 5 μM | 13900 |
| 170 | 67 | 2% @ 10 μM |
| 171 | 0% @ 5 μM | 6% @ 10 μM |
| 172 | 46% @ 5 μM | |
| 173 | 74 | 2000 |

TABLE II-continued

| Example No. | NK-1 IC$_{50}$ nM | NK-2 IC$_{50}$ nM |
| --- | --- | --- |
| 174 | 0 % @ 5 μM | 6400 |
| 175 | 28% @ 5 μM | 9% @ 10 μM |
| 176 | 9% @ 5 μM | 0% @ 10 μM |
| 177 | 0% @ 10 μM | 12% @ 10 μM |

Since the compounds of Formula I are effective tachykinin receptor antagonists, these compounds are of value in the treatment of a wide variety of clinical conditions which are characterized by the presence of an excess of tachykinin. Thus, the invention provides methods for the treatment or prevention of a physiological disorder associated with an excess of tachykinins, which method comprises administering to a mammal in need of said treatment an effective amount of a compound of Formula I or a pharmaceutically acceptable salt thereof. The term "physiological disorder associated with an excess of tachykinins" encompasses those disorders associated with an inappropriate stimulation of tachykinin receptors, regardless of the actual amount of tachykinin present in the locale.

These physiological disorders may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease and irritable bowel syndrome; disorders of bladder function such as bladder detrusor hyper-reflexia and incontinence; artherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Reynaud's disease; and pain or nociception, for example, that attributable to or associated with any of the foregoing conditions, especially the transmission of pain in migraine. For example the compounds of Formula I may suitably be used in the treatment of disorders of the central nervous system such as anxiety, psychosis, and schizophrenia; neurodegenerative disorders such as Alzheimer's disease and Down's syndrome; respiratory diseases such as bronchospasm and asthma; inflammatory diseases such as inflammatory bowel disease, osteoarthritis and rheumatoid arthritis; adverse immunological disorders such as rejection of transplanted tissues; gastrointestinal disorders and diseases such as disorders associated with the neuronal control of viscera such as ulcerative colitis, Crohn's disease and irritable bowel syndrome; incontinence; disorders of blood flow caused by vasodilation; and pain or nociception, for example, that attributable to or associated with any of the foregoing conditions or the transmission of pain in migraine.

The results of several experiments demonstrate that many of the compounds of Formula I are selective tachykinin receptor antagonists. These compounds preferentially bind one tachykinin receptor subtype compared to other such receptors. Such compounds are especially preferred.

For example, NK-1 antagonists are most especially preferred in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, neuropathic pain, opiod-resistant pain, visceral pain, surgical pain, bone injury pain, pain during labor and delivery, pain resulting from burns, post partum pain, angina pain, and genitourinary tract-related pain including cystitis.

In addition to pain, NK-1 antagonists are especially preferred in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; artherosclerosis; inflammatory conditions, such as inflammatory bowel disease, ulcerative colitis, Crohn's disease, rheumatoid arthritis, osteoarthritis, neurogenic inflammation, allergies, rhinitis, cough, dermatitis, urticaria, psoriasis, conjunctivitis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

NK-2 antagonists are especially preferred in the treatment of urinary incontinence, bronchospasm, asthma, adult respiratory distress syndrome, motility disorders of the gastrointestinal tract, such as irritable bowel syndrome, and pain.

In addition to the in vitro binding assays described supra, many of the compounds of this invention have also been tested in in vivo model systems for conditions associated with an excess of tachykinins. Of these compounds tested in vivo many have shown efficacy against said conditions.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes pharmaceutical compositions which contain, as the active ingredient, the compounds of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid cmoposiions such as tablets the principal active ingredient is mixed with a pharmaceutical excipient to form a solid preformulation composition containing a homogeneous mixture of a compound of the present invention. When referring to these preformulation compositions as homogeneous, it is meant that the active ingredient is dipsersed evenly throughout the composition so that the composition may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask, tent, or intermittent positive pressure breathing machine. Solution, suspension, or powder compsoitions may be administered, preferably orally or nasally, from devices which deliver the formulation in an appropriate manner.

The following examples illustrate the pharmaceutical compositions of the present invention.

Formulation Example 1

Hard gelatin capsules containing the following ingredients are prepared:

| Ingredient | Quantity (mg/capsule) |
|---|---|
| Compound of Example 51 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Compound of Example 66 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Compound of Example 17 | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Compound of Example 14 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
|---|---|
| Compound of Example 13 | 40.0 mg |
| Starch | 109.0 mg |
| magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Compound of Example 18 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Compound of Example 43 | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Compound of Example 58 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
|---|---|
| Compound of Example 91 | 250.0 mg |
| Isotonic saline | 1000 ml |

Formulation Example 10

A topical formulation may be prepared as follows:

| Ingredient | Quantity |
|---|---|
| Compound of Example 67 | 1–10 g |
| Emulsifying Wax | 30 g |
| Liquid Paraffin | 20 g |
| White Soft Paraffin | to 100 g |

The white soft paraffin is heated until molten. The liquid praffin and emulsifying wax are incorporated and stirred until dissolved. The compound of Example 67 is added and stirring is continued until dispersed. The mixture is then cooled until solid.

Another preferred formulation employed in the methods of the present invention is the use of transdermal patches. Such transdermal patches may be used to provide continuous or discontinuous infusion of the compounds of the present invention in controlled amounts. The construction and use of transdermal patches for the delivery of pharmaceutical agents is well known in the art. Such patches may be constructed for continous, pulsatile, or on demand delivery of pharmaceutical agents.

---

We claim:

1. A compound of the formula

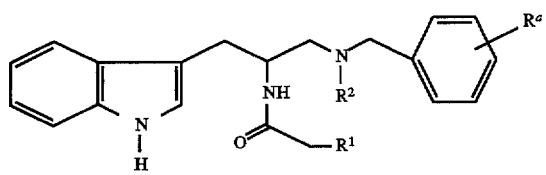

wherein $R^a$ is halo, $C_1$–$C_3$ alkoxy, $C_1$–$C_3$ alkylthio, nitro, trifluoromethyl, or $C_1$–$C_3$ alkyl;

$R^1$ is pyrrolidinyl, morpholinyl, indolinyl, indolyl, benzothienyl, benzofuranyl, quinolinyl, tetrahydropyridinyl, isoquinolinyl, reduced quinolinyl, or reduced isoquinolinyl, which may be substituted with halo, $C_1$–$C_4$ alkyl, $C_1$–$C_4$ alkoxy, trifluoromethyl, amino, $C_1$–$C_4$ alkylamino, or di($Cl_1$–$C_4$ alkyl)amino;

or which may be substituted with phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrolidinyl, $C_2$–$C_6$ alkanoyl, or $C_1$–$C_4$ alkoxycarbonyl;

any one of which phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrolidinyl, $C_2$–$C_6$ alkanoyl, or $C_1$–$C_4$ alkoxycarbonyl groups may be substituted with halo, $C_1$–$C_4$ alkyl, $C_1$–$C_4$ alkoxy, trifluoromethyl, amino, $C_1$–$C_4$ alkylamino, di($C_1$–$C_4$ alkyl)amino, or $C_2$–$C_4$ alkanoylamino;

$R^2$ is hydrogen, acetyl or methylsulfonyl;

or a pharmaceutically acceptable salt or solvate thereof.

2. A compound as claimed in claim 1 wherein $R^a$ is $C_1$–$C_3$ alkoxy, chloro, fluoro, trifluoromethyl or $C_1$–$C_3$ alkylthio.

3. A compound as claimed in claim 2 wherein $R^a$ is methoxy, ethoxy, chloro, trifluoromethyl, or methylthio.

4. A method of treating a condition associated with an excess of tachykinins which comprises administering to a mammal in need thereof an effective amount of a compound of the formula

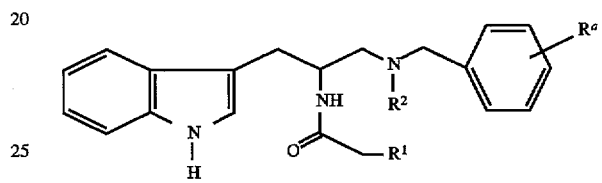

wherein $R^a$ is halo, $C_1$–$C_3$ alkoxy, $C_1$–$C_3$ alkylthio, nitro, trifluoromethyl, or $C_1$–$C_3$ alkyl;

$R^1$ is pyrrolidinyl, morpholinyl, indolinyl, indolyl, benzothienyl, benzofuranyl, quinolinyl, tetrahydropyridinyl, isoquinolinyl, reduced quinolinyl, or reduced isoquinolinyl, which may be substituted with halo, $C_1$–$C_4$ alkyl, $C_1$–$C_4$ alkoxy, trifluoromethyl, amino, $C_1$–$C_4$ alkylamino, or di($C_1$–$C_4$ alkyl)amino;

or which may be substituted with phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl;

any one of which phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl groups may be substituted with halo, $C_1$–$C_4$ alkyl, $C_1$–$C_4$ alkoxy, trifluoromethyl, amino, $C_1$–$C_4$ alkylamino, di($C_1$–$C_4$ alkyl)amino, or $C_2$–$C_4$ alkanoylamino;

$R^2$ is hydrogen, acetyl or methylsulfonyl;

or a pharmaceutically acceptable salt or solvate thereof.

5. A method as claimed in claim 4 employing a compound wherein $R^a$ is $C_1$–$C_3$ alkoxy, chloro, fluoro, trifluoromethyl or $C_1$–$C_3$ alkylthio.

6. A method as claimed in claim 5 employing a compound wherein $R^a$ is methoxy, ethoxy, chloro, trifluoromethyl, or methylthio.

7. A pharmaceutical formulation comprising an effective amount of a compound of the formula

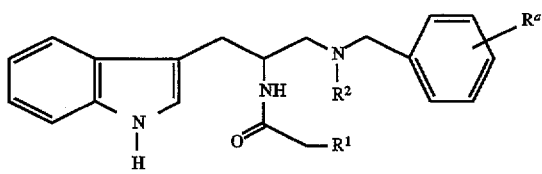

wherein $R^a$ is halo, $C_1$–$C_3$ alkoxy, $C_1$–$C_3$ alkylthio, nitro, trifluoromethyl, or $C_1$–$C_3$ alkyl;

$R^1$ is pyrrolidinyl, morpholinyl, indolinyl, indolyl, benzothienyl, benzofuranyl, quinolinyl, tetrahydropyridinyl, isoquinolinyl, reduced quinolinyl, or reduced isoquinolinyl, which may be substituted with halo, $C_1$–$C_4$ alkyl, $C_1$–$C_4$ alkoxy trifluoromethyl, amino, $C_1$–$C_4$ alkylamino, or di($C_1$–$C_4$ alkyl)amino;

or which may be substituted with phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl;

any one of which phenyl, piperazinyl, $C_3$–$C_8$ cycloalkyl, benzyl, $C_1$–$C_4$ alkyl, piperidinyl, pyridinyl, pyrimidinyl, $C_2$–$C_6$ alkanoylamino, pyrrolidinyl, $C_2$–$C_6$ alkanoyl, or $C_1$–$C_4$ alkoxycarbonyl groups may be substituted with halo, $C_{1-C4}$ alkyl, $C_1$–$C_4$ alkoxy, trifluoromethyl, amino, $C_1$–$C_4$ alkylamino, di($C_1$–$C_4$ alkyl)amino, or $C_2$–$C_4$ alkanoylamino;

$R^2$ is hydrogen, acetyl or methylsulfonyl;

or a pharmaceutically acceptable salt or solvate thereof, in combination with one or ore pharmaceutically acceptable carriers, diluents, or excipients therefor.

8. A formulation as claimed in claim 7 employing a compound wherein $R^a$ is $C_1$–$C_3$ alkoxy, chloro, fluoro, trifluoromethyl or $C_1$–$C_3$ alkylthio.

9. A formulation as claimed in claim 8 employing a compound wherein $R^a$ is methoxy, ethoxy, chloro, trifluoromethyl, or methylthio.

\* \* \* \* \*